(12) United States Patent
Ganapathy et al.

(10) Patent No.: US 8,436,039 B2
(45) Date of Patent: May 7, 2013

(54) INHIBITORS OF THE ATB(0,+) TRANSPORTER AND USES THEREOF

(75) Inventors: Vadivel Ganapathy, Martinez, GA (US); Muthusamy Thangaraju, Evans, GA (US); Puttur Prasad, Martinez, GA (US)

(73) Assignee: Georgia Health Sciences University Research Institute, Inc., Augusta, GA (US)

( * ) Notice: Subject to any disclaimer, the term of this patent is extended or adjusted under 35 U.S.C. 154(b) by 239 days.

(21) Appl. No.: 12/744,863

(22) PCT Filed: Oct. 8, 2009

(86) PCT No.: PCT/US2009/059946
§ 371 (c)(1),
(2), (4) Date: May 26, 2010

(87) PCT Pub. No.: WO2010/042685
PCT Pub. Date: Apr. 15, 2010

(65) Prior Publication Data
US 2010/0305184 A1   Dec. 2, 2010

Related U.S. Application Data

(60) Provisional application No. 61/195,567, filed on Oct. 8, 2008.

(51) Int. Cl.
*A01N 43/38* (2006.01)
*A61K 31/40* (2006.01)

(52) U.S. Cl.
USPC ......................................................... 514/419

(58) Field of Classification Search ............... 514/419
See application file for complete search history.

(56) References Cited

U.S. PATENT DOCUMENTS

| | | | |
|---|---|---|---|
| 2004/0142317 A1 | 7/2004 | Ganapathy et al. | |
| 2005/0095240 A1 | 5/2005 | Ganapathy et al. | |
| 2006/0019241 A1 | 1/2006 | Ganapathy et al. | |
| 2006/0100280 A1* | 5/2006 | Hatanaka et al. | 514/561 |
| 2007/0099844 A1 | 5/2007 | Prendergast et al. | |
| 2009/0123388 A1 | 5/2009 | Ganapathy et al. | |
| 2010/0137236 A1 | 6/2010 | Ganapathy et al. | |
| 2011/0245339 A1 | 10/2011 | Ganapathy et al. | |

FOREIGN PATENT DOCUMENTS

| | | |
|---|---|---|
| WO | WO 02/083060 A2 | 10/2002 |
| WO | WO 02/083060 A3 | 7/2003 |
| WO | WO 2004/048925 A2 | 6/2004 |
| WO | WO 2004/048925 A3 | 1/2005 |
| WO | WO 2005/114217 A2 | 12/2005 |
| WO | WO 2005/114217 A3 | 6/2006 |
| WO | WO 2006/076734 A2 | 7/2006 |
| WO | WO 2006/076734 A3 | 2/2007 |
| WO | WO 2010/042685 A2 | 4/2010 |
| WO | WO 2010/042685 A3 | 8/2010 |

OTHER PUBLICATIONS

Shoaf et al. (The Journal of Pharmacology and Experimental Therapeutics, 1996, 277, 219-224).*
Gupta et al. (Biochemica et Biophysica Acta 2005: 1741, 215-223).*
Fuchs and Bode, "Amino acid transporters ASCT2 and LAT1 in cancer: partners in crime?" Aug. 2005 *Semin. Cancer Biol.* 15:254-266.
Ganapathy et al., "Chapter four—Cellular uptake of amino acids: system and regulation," in *Metabolic and Therapeutic Aspects of Amino Acids in Clinical Nutrition, 2nd Edition* (Cynober, L. A., Ed.). CRC Press, Boca Raton, FL; 2004. Cover page, publisher's page, and pp. 63-78.
Ganapathy and Ganapathy, "Amino Acid Transporter $ATB^{0,+}$ as a delivery system for drugs and prodrugs," Dec. 2005 *Curr. Drug Targets Immune Endocr. Metab. Disord.* 5:357-364.
Glew et al., "Plasma and urinary free amino acid concentrations in preeclamptic women in northern Nigeria," Apr. 2004 *Clin. Chim. Acta* 342:179-185.
Gupta et al., "Upregulation of the amino acid transporter $ATB^{0,+}$ (SLC6A14) in colorectal cancer and metastasis in humans," Jun. 30, 2005 *Biochim. Biophys. Acta* 1741:215-223.
Gupta et al., "Up-regulation of the amino acid transporter $ATB^{0,+}$ (SLC6A14) in carcinoma of the cervix," Jan. 2006 *Gynecol. Oncol.* 100:8-13. Available online on Sep. 15, 2005.
Hatanaka et al., "Transport of D-serine via the amino acid transporter $ATB^{0,+}$ expressed in the colon," Feb. 2002 *Biochem. Biophys. Res. Commun.* 291:291-295.
Kanai and Endou, "Heterodimeric amino acid transporters: molecular biology and pathological and pharmacological relevance," Dec. 2001 *Curr. Drug Metab.* 2:339-354.
Karunakaran et al., "SLC6A14 (ATB0,+) protein, a highly concentrative and broad specific amino acid transporter, is a novel and effective drug target for treatment of estrogen receptor-positive breast cancer," Sep. 9, 2011 *J. Biol. Chem.* 286:31830-31838. Available online on Jul. 19, 2011.
Prasad et al., "Human LAT1, a subunit of system L amino acid transporter: molecular cloning and transport function," Feb. 16, 1999 *Biochem. Biophys. Res. Commun.* 255:283-288.
Thangaraju et al., "Sodium-coupled transport of the short chain fatty acid butyrate by SLC5A8 and its relevance to colon cancer," Oct. 2008 *J. Gastrointest. Surg.* 12:1773-1781; discussion on pp. 1181-1182. Available online on Jul. 16, 2008.
Uchiyama et al., "Functional characterization and cloning of amino acid transporter $B^{0,+}$ ($ATB^{0,+}$) in primary cultured rat pneumocytes," Mar. 2008 *J. Cell. Physiol.* 214:645-654.
Umapathy et al., "Transport of amino acid esters and the amino-acid-based prodrug valganciclovir by the amino acid transporter $ATB^{0,+}$," Jul. 2004 *Pharm. Res.* 21:1303-1310.

(Continued)

*Primary Examiner* — Jeffrey S. Lundgren
*Assistant Examiner* — Michael Schmitt
(74) *Attorney, Agent, or Firm* — Mueting Raasch & Gebhardt, P.A.

(57) ABSTRACT

The present invention includes inhibitors of the amino acid transporter $ATB^{0,+}$ and methods of uses thereof.

22 Claims, 17 Drawing Sheets

OTHER PUBLICATIONS

Anderson et al., "Human solute carrier SLC6A14 is the β-alanine carrier," Sep. 1, 2008 *J. Physiol.* 586:4061-4067. Available online on Jul. 3, 2008.

Anderson et al., "Taurine uptake across the human intestinal brush-border membrane is via two transporters: $H^+$ coupled PAT1 (SLC36A1) and $Na^+$- and $Cl^-$-dependant TauT (SLC6A6)," Feb. 15, 2009 587:731-744. Available online on Dec. 15, 2008.

Eastin, "The U.S. National Toxicology Program evaluation of transgenic mice as predictive models for identifying carcinogens," Feb. 1998 *Environ. Health Perspect.* 106(Suppl. 1):81-84.

Eisenberg-Lerner and Kimchi, "The paradox of autophagy and its implication in cancer etiology and therapy," Apr. 2009 *Apoptosis* 14:376-391.

Flach et al., "Detection of elafin as a candidate biomarker for ulcerative colitis by whole-genome microarray screening," Sep. 2006 *Inflamm. Bowel Dis.* 12:837-842.

Frank et al., "Lactaturia and loss of sodium-dependent lactate uptake in the colon of SLC5A8-deficient mice," Sep. 2008 *J.Biol. Chem.* 283:24729-24737. Available online on Jun. 17, 2008.

Ganapathy, Malliga, "Amino Acid Transporter B: Pharmacology & Therapeutic Use," Grant Abstract, Grant No. GM065344 [online]. National Institute of General Medical Sciences, National Institutes of Health; project dates Apr. 1, 2002 to May 31, 2006 [retrieved on May 30, 2012]. Retrieved from the Internet: <http://projectreporter.nih.gov/pr_Prj_info_desc_dtls.cfm?aid=6463499&icde=12658387&ddparam=&ddvalue=&ddsub=&cr=4&csb=default&cs=ASC&print=yes>; 1 pg.

Ganapathy et al., "Nutrient transporters in cancer: relevance to Warburg hypothesis and beyond," 2009 *Pharmacol. Ther.* 121:29-40.

Hatanaka et al., "$Na^+$- and $Cl^-$-coupled active transport of nitric oxide synthase inhibitors via amino acid transport system $B^{0,+}$," Apr. 2001 *J. Clin. Invest.* 107:1035-1043.

Hatanaka et al., "Transport of Amino Acid-Based Prodrugs by the $Na^+$- and $Cl^-$-Coupled Amino Acid Transporter $ATB^{0,+}$ and Expression of the Transporter in Tissues Amenable for Drug Delivery," Mar. 2004 *J. Pharmacol. Exp. Ther.* 308:1138-1147.

Hou et al., "Inhibition of indoleamine 2,3-dioxygenase in dendritic cells by stereoisomers of 1-methyl-tryptophan correlates with anti-tumor responses," Jan. 2007 *Cancer Res.* 67:792-801.

Humble et al., "Biological, cellular, and molecular characteristics of an inducible transgenic skin tumor model: a review," Dec. 2005 *Oncogene* 24:8217-8228.

Karunakaran et al., "Interaction of tryptophan derivatives with SLC6A14 ($ATB^{0,+}$) reveals the potential of the transporter as a drug target for cancer chemotherapy," Sep. 15, 2008 *Biochem. J.* 414:343-355.

Kwon et al., "Expression of cyclic guanosine monophosphate-dependent protein kinase in metastatic colon carcinoma cells blocks tumor angiogenesis," Apr. 1, 2008 *Cancer* 112:1462-1470.

Miyauchi et al., "Functional identification of SLC5A8, a tumor suppressor down-regulated in colon cancer, as a $Na^+$-coupled transporter for short-chain fatty acids," Apr. 2, 2004 *J. Biol. Chem.* 279:13293-13296. Available online on Feb. 13, 2004.

Nakanishi et al., "$Na^+$- and $Cl^-$-coupled active transport of carnitine by the amino acid transporter $ATB^{0,+}$ from mouse colon expressed in HRPE cells and Xenopus oocytes," Apr. 15, 2001 *J. Physiol.* 532:297-304.

Rotoli et al., "The transport of cationic amino acids in human airway cells: expression of system $y^+L$ activity and transepithelial delivery of NOS inhibitors," May 2005 *FASEB J.* 19:810-812. Available online on Mary 3, 2005.

Sharma et al., "Plasmacytoid dendritic cells from mouse tumor-draining lymph nodes directly activate mature Tregs via indoleamine 2,3-dioxygenase," Sep. 2007 *J. Clin. Invest.* 117:2570-2582.

Shoaf and Schmall, "Pharmacokinetics of α-methyl-L-tryptophan in Rhesus monkeys and calculation of the lumped constant for estimating the rate of serotonin synthesis," 1996 *J. Pharm. Exp. Ther.* 277:219-224.

Shoaf et al., "Brain serotonin synthesis rates in Rhesus monkeys determined by [$^{11}C$]α-methyl-L-tryptophan and positron emission tomography compared to CSF 5-hydroxyindole-3-acetic acid concentrations," 1998 *Neuropsychopharm.* 19:345-353.

Shoaf et al., "The suitability of [$^{11}C$]-α-methyl-L-tryptophan as a tracer for serotonin synthesis: studies with dual administration of [$^{11}C$] and [$^{14}C$] labeled tracer," 2000 *J. Cerebr. Blood Flow Metab.* 20:244-252.

Sloan and Mager, "Cloning and functional expression of a human $Na^+$ and $Cl^-$-dependent neutral and cationic amino acid transporter $B^{0,+}$," Aug. 20, 1999 *J. Biol. Chem.* 274:23740-23745.

Srinivas et al., "Transport of butyryl-L-carnitine, a potential prodrug, via the carnitine transporter OCTN2 and the amino acid transporter $ATB^{0,+}$," Nov. 2007 *Am. J. Physiol. Gastrointest. Liver Physiol.* 293:G1046-G1053. Available online on Sep. 13, 2007.

Suviolahti et al., "The *SLC6A14* gene shows evidence of association with obesity," Dec. 2003 *J. Clin. Invest.* 112:1762-1772.

Tennant et al., "Identifying chemical carcinogens and assessing potential risk in short-term bioassays using transgenic mouse models," Oct. 1995 *Environ. Health Perspect.* 103:942-950.

Tennant et al., "The Tg.AC (v-Ha-ras) transgenic mouse: nature of the model," 2001 *Toxicol. Pathol.* 29(Suppl.):51-59.

Thangaraju et al., "SLC5A8 triggers tumor cell apoptosis through pyruvate-dependent inhibition of histone deacetylases," Dec. 15, 2006 *Cancer Res.* 66:11560-11564.

Tiwari and Allison, "Do allelic variants of *SLC6A14* predispose to obesity?" Dec. 2003 *J. Clin. Invest.* 112:1633-1636.

Wang and Proud, "The mTOR pathway in the control of protein synthesis," Oct. 2006 *Physiology (Bethesda)* 21:362-369.

International Preliminary Report on Patentability issued Apr. 12, 2011, in connection with International Patent Application No. PCT/US2009/059946, filed Oct. 8, 2009; 5 pages.

International Search Report mailed Jun. 18, 2010, in connection with International Patent Application No. PCT/US2009/059946, filed Oct. 8, 2009; 5 pages.

Written Opinion mailed Jun. 18, 2010, in connection with International Patent Application No. PCT/US2009/059946, filed Oct. 8, 2009; 4 pages.

\* cited by examiner

SEQUENCE LISTING

```
<160> NUMBER OF SEQ ID NOS: 14

<210> SEQ ID NO 1
<211> LENGTH: 22
<212> TYPE: DNA
<213> ORGANISM: artificial
<220> FEATURE:
<223> OTHER INFORMATION: Synthetic Oligonucleotide Primer

<400> SEQUENCE: 1
gaaggagaaa gtgtcggctt ca                                           22

<210> SEQ ID NO 2
<211> LENGTH: 22
<212> TYPE: DNA
<213> ORGANISM: artificial
<220> FEATURE:
<223> OTHER INFORMATION: Synthetic Oligonucleotide Primer

<400> SEQUENCE: 2
taccaccttg ccagacgatt tg                                           22

<210> SEQ ID NO 3
<211> LENGTH: 21
<212> TYPE: DNA
<213> ORGANISM: artificial
<220> FEATURE:
<223> OTHER INFORMATION: Synthetic Oligonucleotide Primer

<400> SEQUENCE: 3
gcaaatgcaa gaacgggaca c                                            21

<210> SEQ ID NO 4
<211> LENGTH: 24
<212> TYPE: DNA
<213> ORGANISM: artificial
<220> FEATURE:
<223> OTHER INFORMATION: Synthetic Oligonucleotide Primer

<400> SEQUENCE: 4
tcagggagac cagagctttc acac                                         24

<210> SEQ ID NO 5
<211> LENGTH: 24
<212> TYPE: DNA
<213> ORGANISM: artificial
<220> FEATURE:
<223> OTHER INFORMATION: Synthetic Oligonucleotide Primer

<400> SEQUENCE: 5
acaggaccac ttgctgacag ctta                                         24

<210> SEQ ID NO 6
<211> LENGTH: 24
```

```
<212> TYPE: DNA
<213> ORGANISM: artificial
<220> FEATURE:
<223> OTHER INFORMATION: Synthetic Oligonucleotide Primer

<400> SEQUENCE: 6
acgtgggtga aggattgact ccaa                                          24

<210> SEQ ID NO 7
<211> LENGTH: 24
<212> TYPE: DNA
<213> ORGANISM: artificial
<220> FEATURE:
<223> OTHER INFORMATION: Synthetic Oligonucleotide Primer

<400> SEQUENCE: 7
aaacctccgt gcttctcaga cagt                                          24

<210> SEQ ID NO 8
<211> LENGTH: 24
<212> TYPE: DNA
<213> ORGANISM: artificial
<220> FEATURE:
<223> OTHER INFORMATION: Synthetic Oligonucleotide Primer

<400> SEQUENCE: 8
tgaagtccaa ggctgtcatc gtct                                          24

<210> SEQ ID NO 9
<211> LENGTH: 21
<212> TYPE: DNA
<213> ORGANISM: artificial
<220> FEATURE:
<223> OTHER INFORMATION: Synthetic Oligonucleotide Primer

<400> SEQUENCE: 9
gtgtgatgac gctgctctac g                                             21

<210> SEQ ID NO 10
<211> LENGTH: 20
<212> TYPE: DNA
<213> ORGANISM: artificial
<220> FEATURE:
<223> OTHER INFORMATION: Synthetic Oligonucleotide Primer

<400> SEQUENCE: 10
gatgatggtg aagccgatgc                                               20

<210> SEQ ID NO 11
<211> LENGTH: 21
<212> TYPE: DNA
<213> ORGANISM: artificial
<220> FEATURE:
<223> OTHER INFORMATION: Synthetic Oligonucleotide Primer

<400> SEQUENCE: 11
caactgtgcc accagcgtct a                                             21

<210> SEQ ID NO 12
<211> LENGTH: 22
<212> TYPE: DNA
<213> ORGANISM: artificial
<220> FEATURE:
<223> OTHER INFORMATION: Synthetic Oligonucleotide Primer

<400> SEQUENCE: 12
acgcccaagg tcacataggt ct                                            22
```

```
<210> SEQ ID NO 13
<211> LENGTH: 22
<212> TYPE: DNA
<213> ORGANISM: artificial
<220> FEATURE:
<223> OTHER INFORMATION: Synthetic Oligonucleotide Primer

<400> SEQUENCE: 13
gacgagtttc ccaagtacct ac                                              22

<210> SEQ ID NO 14
<211> LENGTH: 22
<212> TYPE: DNA
<213> ORGANISM: artificial
<220> FEATURE:
<223> OTHER INFORMATION: Synthetic Oligonucleotide Primer

<400> SEQUENCE: 14
cagttaggat agcggtaaga gc                                              22
```

US 8,436,039 B2

INHIBITORS OF THE ATB(0,+) TRANSPORTER AND USES THEREOF

CONTINUING APPLICATION DATA

This application is the §371 U.S. National Stage of International Application No. PCT/US2009/059946, filed 8 Oct. 2009, which claims the benefit of U.S. Provisional Application Ser. No. 61/195,567, filed Oct. 8, 2008, each of which are incorporated by reference herein in their entireties.

GOVERNMENT FUNDING

The present invention was made with government support under Grant No. GM065344, awarded by the National Institutes for Health, Institute of General Medical Sciences. The Government has certain rights in this invention.

BACKGROUND

Cancer is a widespread and deadly disease. Although a variety of therapeutic strategies are currently used for treatment of cancer, for many cancers these treatments do not offer a permanent cure for the disease. Significant improvements in the treatment of cancer have proven difficult to develop. Currently, the standard to measure the success of a new anticancer drug is often an increase in the survival of cancer patients in terms of months, not in years. There is a need for improved agents for the treatment of cancer.

SUMMARY OF THE INVENTION

The present invention includes compositions having alpha methyl tryptophan, wherein the alpha methyl tryptophan includes the L isomer and does not include the D isomer of alpha methyl tryptophan. In some aspects, the composition may further include a pharmaceutically acceptable carrier.

The present invention includes methods of treating cancer in a subject, the method including administering to the subject a composition including an inhibitor of the $ATB^{0,+}$ amino acid transporter. In some aspects, the inhibitor of the $ATB^{0,+}$ amino acid transporter is administered in an amount effective to inhibit amino acid transport into cancer cells. In some aspects, the cancer cells demonstrate enhanced expression of the $ATB^{0,+}$ amino acid transporter. In some aspects, the composition includes the L isomer of alpha methyl tryptophan and does not includes the D isomer of alpha methyl tryptophan.

The present invention includes methods of killing a cancer cell, the method including contacting the cancer cell with an inhibitor of the $ATB^{0,+}$ amino acid transporter. In some aspects, the inhibitor of the $ATB^{0,+}$ amino acid transporter is administered in an amount effective to inhibit amino acid transport into cancer cells. In some aspects, the cancer cells demonstrate enhanced expression of the $ATB^{0,+}$ amino acid transporter. In some aspects, the cancer is colon cancer, is cervical cancer, or breast cancer. In some aspects, the cancer is metastatic.

The present invention includes methods of treating cancer in a subject, the method including determining that the cancer cells demonstrate enhanced expression of the $ATB^{0,+}$ amino acid transporter and administering to the subject a composition including an inhibitor of the $ATB^{0,+}$ amino acid transporter. In some aspects, the inhibitor of the $ATB^{0,+}$ amino acid transporter is administered in an amount effective to inhibit amino acid transport into cancer cells. In some aspects, the cancer cells demonstrate enhanced expression of the $ATB^{0,+}$ amino acid transporter. In some aspects, the cancer is colon cancer, is cervical cancer, or breast cancer. In some aspects, the cancer is metastatic.

The present invention includes methods of treating an inflammatory condition in a subject, the method including administering to the subject a composition including an inhibitor of the $ATB^{0,+}$ amino acid transporter. In some aspects, the inhibitor of the $ATB^{0,+}$ amino acid transporter is administered in an amount effective to inhibit amino acid transport into cells.

The present invention includes methods of treating ulcerative colitis, the method including administering to the subject a composition including an inhibitor of the $ATB^{0,+}$ amino acid transporter. In some aspects, the inhibitor of the $ATB^{0,+}$ amino acid transporter is administered in an amount effective to inhibit amino acid transport into cells.

The present invention includes methods of inhibiting amino acid transport into a cell, the method including contacting the cell with a composition including an inhibitor of the $ATB^{0,+}$ amino acid transporter.

In some aspects any of the compositions and methods of the present invention, the inhibitor of the $ATB^{0,+}$ amino acid transporter includes a tryptophan derivative.

In some aspects any of the compositions and methods of the present invention, the inhibitor of the $ATB^{0,+}$ amino acid transporter includes alpha methyl tryptophan.

In some aspects any of the compositions and methods of the present invention, the composition includes the L isomer of alpha methyl tryptophan and does not includes the D isomer of alpha methyl tryptophan.

In some aspects any of the compositions and methods of the present invention, the inhibitor of the $ATB^{0,+}$ amino acid transporter includes an alpha methyl tryptophan derivative.

In some aspects any of the compositions and methods of the present invention, the composition is formulated for parenteral delivery.

In some aspects any of the compositions and methods of the present invention, the composition is formulated for enteral delivery.

The terms "comprises" and variations thereof do not have a limiting meaning where these terms appear in the description and claims.

Unless otherwise specified, "a," "an," "the," and "at least one" are used interchangeably and mean one or more than one.

BRIEF DESCRIPTION OF THE FIGURES

In FIG. 1A mouse $ATB^{0,+}$ cDNA was expressed heterologously in HRPE cells and the transport function was monitored by measuring the uptake of glycine (10 μM) for 30 min in the presence of NaCl. Tryptophan and its derivatives were present at 1 mM. Uptake values measured in the absence of any competing substrate were taken as 100%. Results represent means±S.E.M. for six measurements from two independent experiments. In FIG. 1B mouse $ATB^{0,+}$ was expressed in *X. laevis* oocytes by injection of cRNA and the transport function was monitored by measuring inward currents induced by tryptophan derivatives (2.5 mM) under voltage-clamp conditions. Results represent means±S.E.M. for five independent measurements in five different oocytes.

FIG. 3A represents $Na^+$-activation kinetics. Inward currents induced by 1-methyl-L-tryptophan were measured in the presence of increasing concentrations of $Na^+$, with $Cl^-$ concentration kept constant at 100 mM. Inset: Hill plot. FIG. 3B represents $Cl^-$-activation kinetics. Inward currents induced by 1-methyl-L-tryptophan were measured in the presence of increasing concentrations of $Cl^-$, with $Na^+$ concentration kept constant at 100 mM. Inset: Hill plot. Since expression levels varied from oocyte to oocyte, data were normalized by taking the current induced by maximal $Na^+$ or $Cl^-$ concentration in each oocyte as 1, and then calculating the currents induced at other concentrations as a fraction of this value. Results represent means±S.E.M. for three independent experiments in three different oocytes.

In FIG. 4A currents induced by 20 μM L-tryptophan were monitored in the absence or presence of 1 mM α-methyl-DL-tryptophan (α-MT) or 1 mM 1-methyl-DL-tryptophan (1-MT). Data are from a representative oocyte; similar results were obtained in three different oocytes. In FIG. 4B currents induced by an amino acid mixture simulating the plasma concentrations of 18 different amino acids were monitored in the absence and presence of increasing concentrations of α-methyl-DL-tryptophan. The composition of the amino acid mixture is given in Table 1. The inhibition of currents observed at each concentration of α-methyl-DL-tryptophan was calculated and used for the plot. Results (means±S.E.M.) are from three different oocytes.

In FIG. 5A expression of IDO1, IDO2, TDO and $ATB^{0,+}$ was monitored by RT-PCR with gene-specific primers. HPRT was used as an internal control. In FIG. 5B expression of $ATB^{0,+}$ protein was monitored by Western blotting. β-Actin was used an internal control. In FIG. 5C transport function of $ATB^{0,+}$ was monitored in MCF7 cells by measuring glycine uptake (10 μM; 15 min incubation) in the presence of NaCl (i.e. presence of $Na^+$ and $Cl^-$), NMDG chloride (i.e. presence of $Cl^-$ but absence of $Na^+$), sodium gluconate (i.e. presence of $Na^+$ but absence of $Cl^-$) or NaCl plus arginine (5 mM). In FIG. 5D transport function of $ATB^{0,+}$ was monitored in MCF10A cells by measuring glycine uptake (10 μM; 15 min incubation) in the presence of NaCl (i.e. presence of $Na^+$ and $Cl^-$), NMDG chloride (i.e. presence of $Cl^-$ but absence of $Na^+$), sodium gluconate (i.e. presence of $Na^+$ but absence of $Cl^-$) or NaCl plus arginine (5 mM). In FIG. 5E arginine-sensitive uptake in the presence of $Na^+$ and $Cl^-$ was taken as uptake via $ATB^{0,+}$. Results represent $ATB^{0,+}$-specific transport activity in MCF7 and MCF10A cells (means±S.E.M. for nine determinations from three independent experiments).

FIG. 6A represents a time course of D-serine uptake (5 μM) in MCF7 cells in the presence of NaCl, NMDG chloride or sodium gluconate. FIG. 6B represents $Na^+$-activation kinetics of D-serine uptake. Inset: Hill plot. FIG. 6C represents $Cl^-$-activation kinetics of D-serine uptake. Inset: Hill plot. Results represent means±S.E.M. for six determinations from two independent experiments.

In FIG. 7A uptake of D-serine (5 μM) was measured for 15 min in the presence of NaCl and in the absence and presence of competing amino acids (5 mM). Uptake values measured in the absence of any competing amino acid substrate were taken as 100%. Results represent means±S.E.M. for six determinations from two independent experiments. FIG. 7B presents dose-response relationship for the inhibition of D-serine uptake by lysine and arginine. FIG. 7C presents kinetics of inhibition of D-serine uptake by α-methyl-DL-tryptophan. Uptake of D-serine was measured at increasing concentrations of D-serine in the presence and absence of α-methyl-DL-tryptophan (100 μM). Results are given in the form of Eadie-Hofstee plots (V versus V/S; V, D-serine uptake in nmol/mg of protein per 15 min; S, D-serine concentration in μM). Results represent means±S.E.M. for six determinations from two independent experiments.

DETAILED DESCRIPTION OF ILLUSTRATIVE EMBODIMENTS OF THE PREFERRED INVENTION

Figure 1:
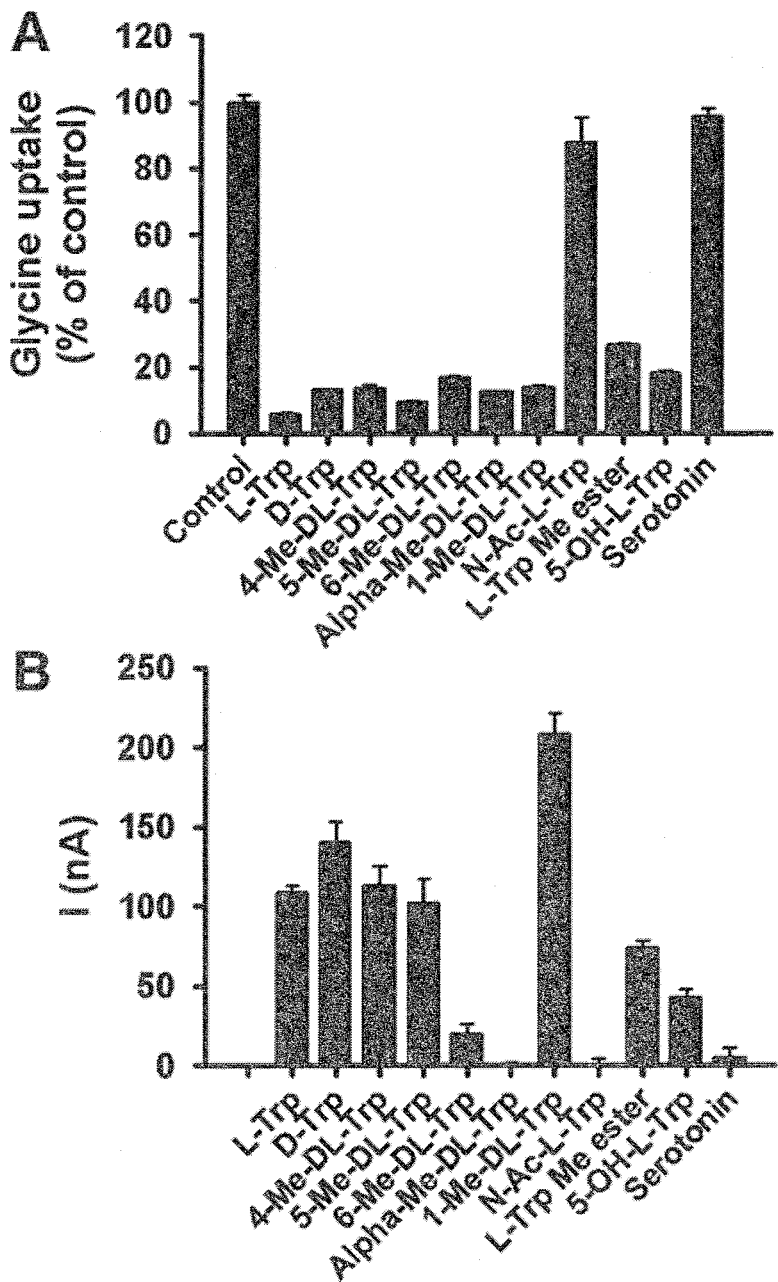
FIG. 1 shows an interaction of tryptophan and its derivatives with $ATB^{0,+}$.

With the present invention, inhibitors of the amino acid transporter ATB$^{0,+}$ have been identified. These inhibitors have been shown to be effective in inhibiting the growth and viability of cancer cells. The amino acid transporter ATB$^{0,+}$ (also referred to herein as "ATB$^{0,+}$ transporter," "the ATB$^{0,+}$ transporter," "ATB0,+," "'ATB 0,+," "ATB (0,+)," "ATB (0,+)," and "SLC6A14") is an amino acid transporter with special functional features (Ganapathy and Ganapathy, 2005, Curr. Drug Targets Immune Endocr. Metab. Disord. 5, 357-364). It has broad substrate selectivity, transporting 18 of the 20 proteinogenic amino acids. The only amino acids that are not substrates for this transporter are glutamate and aspartate, amino acids that are non-essential.

The transport function of ATB$^{0,+}$ is energized by three different driving forces, namely an Na$^+$ gradient, a Cl$^−$ gradient and membrane potential. Theoretically, this transporter has the ability to concentrate its substrates inside the cells more than 1000-fold. ATB$^{0,+}$ has been cloned from human and rodent tissues, and the function of the cloned transporter has been characterized in heterologous expression systems (Sloan and Mager, 1999, J. Biol. Chem. 274, 23740-23745; Nakanishi et al., 2001, J. Physiol. 532, 297-304; Uchiyama et al., 2008, J. Cell. Physiol. 214, 645-654). According to the HUGO (Human Genome Organisation) nomenclature, ATB$^{0,+}$ is identified as SLC6A14 (solute carrier family 6 member 14; i.e. the 14th member of the solute carrier gene family SLC6). Functional expression in Xenopus laevis oocytes has demonstrated that the transport process mediated by ATB$^{0,+}$ is electrogenic, associated with the transfer of net positive charge into the oocytes (Sloan and Mager, 1999, J. Biol. Chem. 274, 23740-23745; Nakanishi et al., 2001, J. Physiol. 532, 297-304).

Recent studies have demonstrated the therapeutic potential of this transporter capitalizing on its ability to transport a variety of pharmacological agents into cells, including NOS (nitric oxide synthase) inhibitors (Hatanaka et al., 2001, J. Clin. Invest. 107, 1035-1043) and amino acid-based prodrugs of the antiviral agents acyclovir and ganciclovir (Hatanaka et al., 2004, J. Pharmacol. Exp. Ther. 308, 1138-1147; Umapathy et al., 2004, Pharm. Res. 21, 1303-1310). See also, U.S. patent application Ser. Nos. 10/467,893 and 11/813,343.

There is emerging evidence for tumor-associated up-regulation of ATB$^{0,+}$ (Gupta et al., 2005, Biochim. Biophys. Acta 1741, 215-223; Gupta et al., 2006, Gynecol. Oncol. 100, 8-13). The expression of this transporter is markedly induced in colorectal cancer (Gupta et al., 2005, Biochim. Biophys. Acta 1741, 215-223) and cervical cancer (Gupta et al., 2006, Gynecol. Oncol. 100, 8-13), and the up-regulation is demonstrable at the mRNA level as well as at the protein level. The ability of the transporter to recognize structurally diverse pharmacological agents lends credence to its therapeutic potential in cancer treatment. None of the other known amino acid transporters in mammalian cells shares these features.

Tumor cells have a unique metabolic need for amino acids to support rapid growth. This is achieved by facilitation of cell cycle and resistance to apoptosis. Enhanced cell proliferation places increased demand for nutrients to serve as the building blocks for the synthesis of macromolecules (DNA, RNA, proteins, and lipids) and as the carbon source for generation of metabolic energy in tumor cells. These nutrients include glucose, amino acids, fatty acids, vitamins, and micronutrients such as trace elements. Most of these nutrients are hydrophilic and do not permeate easily across the plasma membrane in mammalian cells. Uptake of hydrophilic nutrients into cells requires specific transporters in the plasma membrane. Even fatty acids, which are hydrophobic, are taken up into cells via specific transporters. Tumor cells employ various mechanisms to satisfy their increased demand for nutrients. Vascularization in solid tumors enhances the blood flow, thus increasing the availability of blood-borne nutrients to tumor cells.

The present invention demonstrates that the entry of nutrients into tumor cells is enhanced by upregulation of specific transporters in the plasma membrane. In some instances, the same signaling events that promote vascularization participate also in the upregulation of nutrient transporters, thus coordinating the availability of nutrients with their entry into tumor cells. Since the ability of tumor cells to support their increased demand for nutrients is obligatory for their growth, the pathways involved in this process have potential as drug targets for the treatment of cancer.

With the present invention, inhibitors of the ATB$^{0,+}$ transporter are used in methods of treating cancer, inflammatory diseases, and other conditions, including, but not limited to, ulcerative colitis and inflammatory bowel disease. With the inhibition of amino acid transport, cells cannot obtain essential nutrients and cannot proliferate fast enough to sustain their growth. Thus, with the present invention it will be possible to starve tumor cells to death by interfering with the availability of essential nutrients and their entry into cells. Such nutrient deprivation presents a new strategy to kill cells, including, but not limited to cancer cells, inflamed cells, and cells of the immune system.

The present invention demonstrates that the expression of the ATB$^{0,+}$ transporter is induced and increased compared to normal cells in a variety of cancers. This observation increases the potential of inhibitors as chemotherapeutic agents. Since tumor cells induce these transporters specifically for their unique metabolic needs, normal cells are expected to be relatively resistant to the therapeutic actions of such compounds, thus reducing undesirable side effects.

As used herein, an inhibitor (also referred to herein as a "blocker") is an agent capable of preventing or decreasing amino acid transport by the $ATB^{0,+}$ transporter. Inhibition of ATB0,+ may occur at any time during protein production and function. For example, inhibition may occur at the transcriptional, translational, and post-translational level. Means of inhibiting uptake may include, without limitation, blocking the interaction between the amino acid and the transporter by competitive binding for the substrate binding site or by binding to the transporter and providing a physical barrier for the amino acid. In another embodiment, the inhibitor may block amino transport by allowing uptake but preventing, for example, electrical current induction.

An inhibitor may be a competitive, noncompetitive, or irreversible inhibitor. A competitive inhibitor is a compound that reversibly inhibits transport activity at the catalytic site, a noncompetitive inhibitor is a compound that reversibly inhibits transport activity at a non-catalytic site, and an irreversible inhibitor is a compound that irreversibly destroys transport activity by forming a covalent bond with the transporter.

Inhibitors of the $ATB^{0,+}$ transporter include, but are not limited to, small molecules, antibodies, peptides, nucleic acid molecules (including, for example, an antisense molecule, a PNA, or an RNAi), and peptidomimetics. An inhibitor of the $ATB^{0,+}$ transporter may be identified and characterized using a variety of methods, including, but not limited to any of those described herein.

An inhibitor of the $ATB^{0,+}$ transporter may be a small molecule. In some embodiments of the present invention, an inhibitor of the $ATB^{0,+}$ transporter is an amino acid or a derivative of an amino acid. For example, an inhibitor may be a tryptophan derivative.

In some embodiments, the inhibitor is methyltryptophan or a derivative thereof In a preferred embodiment the inhibitor is an alpha-methyltryptophan (also referred to herein as alpha-MT, a-MT, a-methyltryptophan, α-methyltryptophan, α-MT, or αMT) or a derivative thereof. Typically, the indole side chain unique to tryptophan is present on the α-carbon (i.e. the chiral carbon) and may be referred to as an α-amino acid. The inhibitor of the present invention may exist as either the D-isomer, the L-isomer, or a combination thereof. Derivations of α-methyltryptophan may occur independently or in combination. Examples of derivations include, without limitation, substitution of the methyl group on the α-carbon with an ethyl, propyl, butyl, pentyl, or longer carbon chain. The carbon chain may be straight or it may be branched. Optionally, the methyl group or the substituted carbon chain may be present on the β-carbon. Another example of a derivation of the inhibitor may include, without limitation, the addition of groups on the aromatic carbons. For example, a methyl or a longer carbon chain may be present on one or more of the C1, C2, C3, C4, C5, C6, or C7 carbon(s) of the indole ring. Alternatively, a hydroxyl (—OH) or a halogen (such as bromine, fluorine, chlorine, or iodine) may be present on one or more of the C1, C2, C3, C4, C5, C6, or C7 carbon(s) of the indole ring.

In some embodiments, an inhibitor of the $ATB^{0,+}$ transporter, including, but not limited to alpha methyltryptophan and derivatives thereof, may be a racemic mixture of an inhibitor, an isolated D isomer of an inhibitor, or an isolated L isomer of an inhibitor. For example, inhibition of the $ATB^{0,+}$ transporter may be accomplished by contacting the transporter with a composition that includes a mixture of the D and L isomers of the inhibitor, including, for example, a racemic mixture. Inhibition of the $ATB^{0,+}$ transporter may be accomplished by contacting the transporter with a composition that includes one enantiomer of an inhibitor, but does not include the other enantiomer. For example, inhibition of the $ATB^{0,+}$ transporter may be accomplished by contacting the transporter with a composition that includes the D isomer, but does not include the L isomer of the inhibitor. Such a composition consists essentially of the D isomer of the inhibitor. Inhibition of the $ATB^{0,+}$ transporter may be accomplished by contacting the transporter with a composition that includes the L isomer, but does not include the D isomer of the inhibitor. Such a composition consists essentially of the L isomer. The purification of D and L isomers can be carried out, for example, as described herein Example 5.

An inhibitor of the $ATB^{0,+}$ transporter may be a nucleic acid molecule. As used herein a nucleic acid molecule may be, for example, deoxyribonucleotides and ribonucleotides. The nucleotides of the nucleic acid molecule may be naturally occurring, synthetic, or modified nucleotides. A nucleic acid molecule may be modified or tagged.

A nucleic acid molecule may be designed to inhibit $ATB^{0,+}$ mediated amino acid transport function by binding to the SLC6A14 gene in a manner that prevents transcription or prevents production of a functional transcript. For example, the nucleic acid molecule may target the start codon or region upstream of the start codon such that transcription does not occur. Alternatively, the nucleic acid molecule may target any portion of SLC6A14 that results in a transcript fragment which cannot be translated. The process of nucleic acid transcription and the cellular machinery necessary for nucleic acid transcription are well-known in the art. The nucleic acid molecule of the invention may prevent transcription of SLC6A14 at any point in the transcription process.

A nucleic acid molecule may also be designed to inhibit $ATB^{0,+}$ by binding to the SLC6A14 transcript in a manner that prevents translation or prevents production of a functional protein. For example, DNA, RNA, or hybrid molecules (i.e., consisting of both DNA and RNA) may be complementary to any portion of the SLC6A14 transcript including, without limitation, the 3' untranslated region (UTR), the 5' UTR, any exon, or any intron. Hybridization of the nucleic acid molecule of the invention to any portion of the SLC6A14 transcript prevents translation or results in the translation of a non-functional protein. The process of protein translation and the cellular machinery necessary for translation are well-known in the art. The nucleic acid molecule of the invention may prevent translation of ATB 0,+ at any point in the translation process.

Nucleic acid molecules may be delivered as either single-stranded or double-stranded molecules. The nucleic acid molecules may be delivered as hybrids. Alternatively, the nucleic acid molecules may be incorporated into an expression vector. Expression vectors are well-known in the art. Typical expression vectors are DNA-based and produce an RNA transcript. However, vectors may also be RNA-based and may produce either an RNA transcript or a cDNA fragment.

An inhibitor of the $ATB^{0,+}$ transporter may be an antibody. Such an antibody may, for example, bind specifically to $ATB^{0,+}$ with a binding affinity that reduces or prevents the transporter function of $ATB^{0,+}$. Such an antibody may, for example, bind specifically to $ATB^{0,+}$ with a binding affinity that prevents or inhibits the binding of a substrate to the transporter. An antibody of the present invention may bind to $ATB^{0,+}$ transporter and not bind to other transporter polypeptides.

An antibody of the present invention may bind to the C-terminal tail of the transporter and not bind to the N-terminal portion of the transporter. For example, an antibody may bind to the C-terminal half of the transporter and not bind to the N-terminal half of the transporter. An antibody of the present invention may bind to the N-terminal tail of the transporter and not bind to the C-terminal portion of the transporter. For example, an antibody may bind to the N-terminal half of the transporter and not bind to the C-terminal half of the transporter As used herein, specific binding means binding that is measurably different from a non-specific interaction. Specific binding can be measured, for example, by determining binding of a molecule compared to binding of a control molecule, which generally is a molecule of similar structure that does not have binding activity, for example, an antibody that binds a distinct epitope or antigen. Specificity of binding also can be determined, for example, by competition with a control molecule, for example, competition with an excess of the same molecule. In this case, specific binding is indicated if the binding of a molecule is competitively inhibited by itself. Thus, specific binding between an antibody and antigen is measurably different from a non-specific interaction and occurs via the antigen binding site of the antibody.

As used herein, selective binding refers to a binding interaction that is both specific and discriminating between molecules, for example, an antibody that binds to a single molecule or closely related molecules. For example, an antibody can exhibit specificity for an antigen that can be both specific and selective for the antigen if the epitope is unique to a molecule. Thus, a molecule having selective binding can differentiate between molecules, as exemplified by an antibody having specificity for an epitope unique to one molecule or closely related molecules.

As used herein the term "binding affinity" is intended to mean the strength of a binding interaction and includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction. For example, a bivalent heteromeric variable region binding fragment can exhibit altered or optimized. As used herein, the term "substantially the same" when used in reference to binding affinity is intended to mean similar or identical binding affinities where one molecule has a binding affinity that is similar to another molecule within the experimental variability of the affinity measurement. The experimental variability of the binding affinity measurement is dependent upon the specific assay used and is known to those skilled in the art.

An antibody may be an intact antibody, an antibody binding fragment, or a chimeric antibody. A chimeric antibody may include both human and non-human portions. An antibody may be a polyclonal or a moncoclonal antibody. An antibody may be a derived from a wide variety of species, including, but not limited to mouse and human. An antibody may be a humanized antibody. An antibody may be linked to another functional molecule, for example, another peptide or protein, a toxin, a radioisotope, a cytotoxic agent, cytostatic agent, a polymer, such as, for example, polyethylene glycol, polypropylene glycol or polyoxyalkenes.

The antibodies of the present invention include various antibody fragments, also referred to as antigen binding fragments, which include only a portion of an intact antibody, generally including an antigen binding site of the intact antibody and thus retaining the ability to bind antigen. Examples of antibody fragments include, for example, Fab, Fab', Fd, Fd', Fv, dAB, and F(ab')2 fragments produced by proteolytic digestion and/or reducing disulfide bridges and fragments produced from an Fab expression library. Such antibody fragments can be generated by techniques well known in the art. Antibodies of the present invention can include the variable region(s) alone or in combination with the entirety or a portion of the hinge region, CH1 domain, CH2 domain, CH3 domain and/or Fc domain(s).

Antibodies include, but are not limited to, polyclonal antibodies, affinity-purified polyclonal antibodies, monoclonal antibodies, human antibodies, humanized antibodies, chimeric antibodies, anti-idiotypic antibodies, multispecific antibodies, single chain antibodies, single-chain Fvs (scFv), disulfide-linked Fvs (sdFv), Fab fragments, F(ab') fragments, F(ab')2 fragments, Fv fragments, diabodies, linear antibodies fragments produced by a Fab expression library, fragments comprising either a VL or VH domain, intracellularly-made antibodies (i.e., intrabodies), and antigen-binding antibody fragments thereof.

An antibody of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins can have both heavy and light chains. An array of IgG, IgE, IgM, IgD, IgA, and IgY heavy chains can be paired with a light chain of the kappa or lambda form.

An antibody of the invention can be from any animal origin, including birds and mammals. In some embodiments, the antibodies are human, murine, rat, donkey, sheep, rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins.

The term "polyclonal antibody" refers to an antibody produced from more than a single clone of plasma cells. In contrast "monoclonal antibody" refers to an antibody produced from a single clone of plasma cells. The preparation of polyclonal antibodies is well known. Polyclonal antibodies may be obtained by immunizing a variety of warm-blooded animals such as horses, cows, goats, sheep, dogs, chickens, rabbits, mice, hamsters, guinea pigs and rats as well as transgenic animals such as transgenic sheep, cows, goats or pigs, with an immunogen. The resulting antibodies may be isolated from other proteins by using an affinity column having an Fc binding moiety, such as protein A, or the like.

Monoclonal antibodies can be obtained by various techniques familiar to those skilled in the art. For example, spleen cells from an animal immunized with a desired antigen are immortalized, commonly by fusion with a myeloma cell. Monoclonal antibodies can be isolated and purified from hybridoma cultures by techniques well known in the art. Other known methods of producing transformed B cell lines that produce monoclonal antibodies may also be used. In some embodiments, the antibody can be recombinantly produced, for example, produced by phage display or by combinatorial methods. Such methods can be used to generate human monoclonal antibodies.

A therapeutically useful antibody may be derived from a "humanized" monoclonal antibody. Humanized monoclonal antibodies are produced by transferring one or more CDRs from the heavy and light variable chains of a mouse (or other species) immunoglobulin into a human variable domain, then substituting human residues into the framework regions of the murine counterparts. The use of antibody components derived from humanized monoclonal antibodies obviates potential problems associated with immunogenicity of murine constant regions. The constant region of a humanized monoclonal antibody of the present invention can be that from human immunoglobulin belonging to any isotype. It may be, for example, the constant region of human IgG.

The present invention includes antibody constructs with all of the CDR regions of an anti-transporter antibody, or a subset thereof. For example, the present invention also includes antibody constructs with one, two, or three of the heavy chain CDRs of an anti-transporter antibody, and/or one, two, or three of the CDR regions of the light chain of an anti-transporter antibody, wherein such an antibody retains an anti-transporter binding specificity.

The present invention includes also antibodies that compete with a monoclonal antibody for binding to a transporter, or compete with a monoclonal antibody in the inhibition of transporter function.

Antibodies of the present invention include chimeric antibodies. A chimeric antibody is one in which different portions are derived from different animal species. For example, chimeric antibodies can be obtained by splicing the genes from a mouse antibody molecule with appropriate antigen specificity together with genes from a human antibody molecule of appropriate biological specificity.

Antibodies of the present invention can be produced by an animal, chemically synthesized, or recombinantly expressed. Antibodies of the present invention can be purified by any method known in the art for purification of an immunoglobulin molecule, for example, by chromatography (e.g., ion exchange, affinity, and sizing column chromatography), centrifugation, differential solubility, or by any other standard technique for the purification of proteins.

Antibodies of the present invention can be assayed for immunospecific binding by the methods described herein and by any suitable method known in the art. The immunoassays that can be used include but are not limited to competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art.

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells.

The present invention further provides an isolated polynucleotide molecule having a nucleotide sequence encoding a monoclonal antibody of the invention. The present invention is further directed to an isolated polynucleotide molecule having a nucleotide sequence that has at least 75%, at least 80%, at least 85%, at least 90%, at least 95%, at least 96%, at least 97%, at least 98%, or at least 99% sequence identity to nucleotide sequence encoding a monoclonal antibody of the invention. The invention also encompasses polynucleotides that hybridize under high stringency to a nucleotide sequence encoding an antibody of the invention, or a complement thereof. As used herein "stringent conditions" refer to the ability of a first polynucleotide molecule to hybridize, and remain bound to, a second, filter-bound polynucleotide molecule in 0.5 M NaHPO4, 7% sodium dodecyl sulfate (SDS), and 1 mM EDTA at 65° C., followed by washing in 0.2×SSC/ 0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). Also included in the present invention are polynucleotides that encode one or more of the CDR regions or the heavy and/or light chains of a monoclonal antibody of the present invention, and polynucleotides having a sequence that has at least 90%, at least 95%, at least 96%, at least 97%, at least 98%, or at least 99% sequence identity to a nucleotide sequence including one or more CDRs. General techniques for cloning and sequencing immunoglobulin variable domains and constant regions are well known.

The monoclonal antibodies of the present invention may be coupled directly or indirectly to a therapeutic moiety or a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to agents may be used for diagnostic or therapeutic purposes. Examples of such agents include various enzymes, prosthetic groups, fluorescent materials, luminescent materials, bioluminescent materials, radioactive materials, positron emitting metals using various positron emission tomographies, and nonradioactive paramagnetic metal ions. The agent can be coupled or conjugated either directly to the antibody or indirectly, through an intermediate such as, for example, a linker known in the art, using techniques known in the art. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine (121I, 123I, 125I, 131I), carbon (14C), sulfur (35S), tritium (3H), indium (111In, 112In, 113mIn, 115mIn), technetium (99Tc, 99mTc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, and 97Ru. Techniques for conjugating such therapeutic moieties to antibodies are well-known. Included in the present invention are compositions of one or more of the antibodies of the present invention.

An inhibitor of the present invention may be coupled directly or indirectly to a detectable marker or a therapeutic moiety by techniques well known in the art. A detectable marker is an agent detectable, for example, by spectroscopic, photochemical, biochemical, immunochemical, or chemical means. Useful agents include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate such as, for example, a linker known in the art, using techniques known in the art. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine (121I, 123I, 125I, 131I), carbon (14C), sulfur (35S), tritium (3H), indium (111In, 112In, 113mIn, 115mIn), technetium (99Tc, 99mTc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, and 97Ru. Techniques for conjugating such therapeutic moieties to antibodies are well-known. Included in the present invention are compositions of one or more of the antibodies of the present invention.

The present invention includes compositions of the inhibitors. A composition may also include, for example, buffering agents to help to maintain the pH in an acceptable range or preservatives to retard microbial growth. Such compositions may also include a pharmaceutically acceptable carrier. As used herein, the term "pharmaceutically acceptable carrier" refers to one or more compatible solid or liquid filler, diluents or encapsulating substances which are suitable for administration to a human or other vertebrate animal. The compositions of the present invention are formulated in pharmaceutical preparations in a variety of forms adapted to the chosen route of administration The present invention also includes pharmaceutically acceptable salts of inhibitors. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods.

The methods of the present invention may also be administered to a patient for the treatment of cancer. Cancers to be treated by the present invention include, but are not limited to, melanoma, basal cell carcinoma, colorectal cancer, pancreatic cancer, breast cancer, prostate cancer, lung cancer (including small-cell lung carcinoma and non-small-cell carcinoma, leukemia, lymphoma, sarcoma, ovarian cancer, Kaposi's sarcoma, Hodgkin's Disease, Non-Hodgkin's Lymphoma, multiple myeloma, neuroblastoma, rhabdomyosarcoma, primary thrombocytosis, primary macroglobulinemia, small-cell lung tumors, primary brain tumors, stomach cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, glioblastoma, and adrenal cortical cancer.

The efficacy of treatment of a cancer may be assessed by any of various parameters well known in the art. This includes, but is not limited to, determinations of a reduction in tumor size, determinations of the inhibition of the growth, spread, invasiveness, vascularization, angiogenesis, and/or metastasis of a tumor, determinations of the inhibition of the growth, spread, invasiveness and/or vascularization of any metastatic lesions, determinations of tumor infiltrations by immune system cells, and/or determinations of an increased delayed type hypersensitivity reaction to tumor antigen. The efficacy of treatment may also be assessed by the determination of a delay in relapse or a delay in tumor progression in the subject or by a determination of survival rate of the subject, for example, an increased survival rate at one or five years post treatment. As used herein, a relapse is the return of a tumor or neoplasm after its apparent cessation, for example, such as the return of leukemia.

Cancers to be treated by the methods of the present invention include cancers that express the $ATB^{0,+}$ transporter. Such expression may be at a level that is increased or enhanced when compared to the level expressed on normal, non-cancerous cells.

The present invention also includes a method for treating an inflammatory bowel disease that express $ATB^{0,+}$ in the inflamed tissue. The method may include administering the $ATB^{0,+}$ inhibitor to a patient in need thereof. Importantly, $ATB^{0,+}$ is not expressed or is expressed at low levels in adjacent non-diseased tissue. Inflammatory bowel disease include, without limitation, irritable bowel syndrome, Crohn's disease, and ulcerative colitis.

Also included in the present invention is a method for treating a proliferative disease that expresses $ATB^{0,+}$ in the proliferating tissue. The method may include administering the $ATB^{0,+}$ inhibitor of the invention to a patient in need thereof Importantly, $ATB^{0,+}$ is not expressed or is expressed at low levels in adjacent non-diseased tissue. Proliferative diseases include hyperplasias (including, without limitation, hyperplastic polyps, adenometous polyps, hamartomatous polyps, and inflammatory polyps), benign cancers, and malignant cancers. Preferably the method of the invention is used to treat cancer in the digestive system. Preferably the cancer is a colon cancer. Optionally, the method of the invention is used to treat a metastasis derived from a primary colon cancer.

The methods of the present invention may include a step of determining the level or amount of the $ATB^{0,+}$ transporters expressed on cells in a sample and the comparison to expression levels of the transporter on normal or control cells. The methods of the present invention may include deciding to clinically treat a subject with the administration of an inhibitor the $ATB^{0,+}$ transporter if the cells in the sample express an increased level of the $ATB^{0,+}$ transporter.

The present invention includes methods of detecting diseases associated with the increased expression of the $ATB^{0,+}$ transporter in cells by determining the increased expression of the $ATB^{0,+}$ transporter in a cell sample. Such diseases include, for example, cancer and inflammatory diseases. Such identification allows $ATB^{0,+}$ to be used as a biomarker in the diagnosis of such diseases and allows for the early identification of such diseases. The present invention includes methods of detecting the metastases of an the ATB$^{0,+}$ transporter positive cancer.

As used herein "treating" or "treatment" may include therapeutic and prophylactic treatments. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. The findings of the present invention can be used in methods that include, but are not limited to, methods for treating cancer, methods to treat an infections, methods to increase an immune responses, methods to reduce immunosuppression mediated by regulatory T cells, and methods to increase or stimulate T cell mediated immune responses.

In some embodiments of the methods of the present invention, more than one inhibitors of the ATB$^{0,+}$ transporter may be administered. The compositions of the present invention include a mixture or cocktail of two, three, four, five, or more inhibitors.

With the methods of the present invention, one or more additional therapeutic agents may be administered, in addition to the administration of an inhibitor of the ATB$^{0,+}$ transporter. An inhibitor of the ATB$^{0,+}$ transporter may be administered before, after, and/or coincident to the administration of one or more additional therapeutic agents. An inhibitor of the ATB$^{0,+}$ transporter and one or more additional therapeutic agents may be administered separately or as a part of a mixture or cocktail.

As used herein, an additional therapeutic agent is not an inhibitor of the ATB$^{0,+}$ transporter. As used herein, an additional therapeutic agent is an agent whose use for the treatment of cancer, an infection, or an immune disorder is known the skilled artisan. Additional therapeutic treatments include, but are not limited to, surgical resection, radiation therapy, hormone therapy, vaccines, antibody based therapies, whole body irradiation, bone marrow transplantation, peripheral blood stem cell transplantation, the administration of chemotherapeutic agents (also referred to herein as "antineoplastic chemotherapy agent," "antineoplastic agents," or "antineoplastic chemotherapeutic agents"), cytokines, antiviral agents, immune enhancers, tyrosine kinase inhibitors, signal transduction inhibitors, antibiotic, antimicrobial agents, a TLR agonists, such as for example, bacterial lipopolysaccharides (LPS), one or more CpG oligonucleotides (ODN), metabolic breakdown products of tryptophan, inhibitors of a GCN2 kinase, and adjuvants.

In some aspects of the present invention, the administration of one or more inhibitors of the ATB$^{0,+}$ transporter may allow for the effectiveness of a lower dosage of other therapeutic modalities when compared to the administration of the other therapeutic modalities alone, providing relief from the toxicity observed with the administration of higher doses of the other modalities.

The agents of the present invention can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical, or injection into or around the tumor.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intraperitoneal, and intratumoral administration. In this connection, sterile aqueous media that can be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

For enteral administration, the inhibitor may be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants. Such an implant may be implanted within the tumor.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

An agent of the present invention may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

With the methods of the present invention, the efficacy of the administration of one or more agents may be assessed by any of a variety of parameters well known in the art.

As used herein, the term "subject" includes, but is not limited to, humans and non-human vertebrates. In preferred embodiments, a subject is a mammal, particularly a human. A subject may be an individual. A subject may be a patient. Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

The methods of the present invention include in vivo and in vitro methods. As used herein "in vitro" is in cell culture and "in vivo" is within the body of a subject.

As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

In some therapeutic embodiments, an "effective amount" of an agent is an amount that results in a reduction of at least one pathological parameter. Thus, for example, in some aspects of the present invention, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

For any method disclosed herein that includes discrete steps, the steps may be conducted in any feasible order. And, as appropriate, any combination of two or more steps may be conducted simultaneously.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The present invention also includes genetically engineered animals that do not express the $ATB^{0,+}$ transporter, animals that over express the $ATB^{0,+}$ transporter, animals that express an altered form of the $ATB^{0,+}$ transporter, and animals that demonstrate an altered pattern of tissue expression of the $ATB^{0,+}$ transporter. Also included in the invention are offspring animals and cells derived from such genetically engineered animals and methods of using the animals and cells.

The present invention also includes genetically engineered animals that evade intestinal/colon phenotypes, genetically engineered animals that are predisposed to intestinal/colon phenotypes, and methods of using the animals. Also included in the invention are cells derived from such genetically engineered animals.

As used herein, the term "genetically engineered" refers to an animal that has induced mutations, including, but not limited to, transgenes, targeted mutations (knockouts and/or knockins), and retroviral, proviral, or chemically-induced mutations. A number of animals are commonly used in genetically engineering animals including, but not limited to, mammals, fruit flies, nematodes, and fish. Preferably, the animal is a non-human mammal. Even more preferably, the animal is a mouse.

A preferred genetically engineered animal of the present invention is a targeted animal. Targeted animals may be engineered by first producing the targeting vector. The targeting vector is typically engineered to contain a desired coding region disruption, replacement, or duplication. For instance, a preferred genetically engineered animal on the present invention may target the SLC6A14 gene for disruption. The targeting vector may contain a modification to the SLC6A14 gene that deletes all or a portion of the gene. SCL6A14 contains 14 exons. The targeting vector may contain any deletion of SCL6A14 that results in the absence of the $ATB^{0,+}$ transporter or a deletion that encodes a non-functional $ATB^{0,+}$ transporter. A particularly preferred targeting vector contains a deletion of a ~2.6 kb region (containing exons 1 and 2 and about ~1 kb of sequence upstream of exon 1) of SLC6A14.

The targeting vector may further include "homology arms" present at the 5' and 3' ends of the DNA. The homology arms are used to direct the location of homologous recombination and thereby control the site of genomic insertion, also referred to as the target site. The exogenous DNA may be introduced into the genome of an embryonic stem (ES) cell via homologous recombination between the introduced exogenous DNA and the endogenous target site. In a mouse, for example, the genetically-modified ES cells are then microinjected into host embryos at the eight-cell blastocyst stage. These embryos are transferred to pseudopregnant host females, which then bear chimeric progeny. The chimeric progeny carrying the targeted mutation in their germ line are then bred to establish a line. If the newly established line has a disrupted or deleted gene, it is called a knock-out; if it has a new, replaced, or duplicated gene, it is called a knock-in. The presence of the exogenous DNA can be detected through methods for detecting DNA that are well known in the art such as PCR and Southern blotting. For targeting constructs engineered to express a coding sequence, expression of the coding sequence can be detected at either the transcriptional (RNA) or translational (protein) level. Methods of detecting RNA are well known in the art and include, for example, in situ hybridization, reverse-transcription PCR, and Northern blotting. Methods of detecting protein are well known in the art and include, for example, immunohistochemistry, immunocytochemistry, ELISAs, and immunoblotting (i.e. Western blotting).

In another embodiment, a genetically engineered animal of the invention may carry an exogenous DNA which has been incorporated into their genome, for example, via pronuclear microinjection and non-homologous recombination, via homologous recombination in stem cells, or via infection with a retroviral vector. "Exogenous" refers to foreign DNA (i.e., DNA that is not normally present in that animal) or DNA that is normally present in that animal but is operably linked to a regulatory sequence to which it is not normally operably linked. Preferably, the exogenous DNA includes at least a coding sequence. As used herein the terms "coding sequence" and "coding region" refers to a polynucleotide that encodes an RNA, and under the proper regulatory components expresses the encoded RNA. A coding sequence may be a genomic sequence, inclusive of non-coding regions (introns) as well as coding regions (exons), or a sequence in which the non-coding portions have been removed, for example a complementary DNA (cDNA). The boundaries of a coding sequence are generally determined by a translation start codon at its 5' end and a translation stop codon at its 3' end. Optionally the exogenous DNA further comprises a regulatory sequence. A "regulatory sequence" is a nucleotide sequence that regulates expression of a coding sequence to which it is operably linked. Non-limiting examples of regulatory sequences include, for example, promoters, enhancers, transcription initiation sites, translation start sites, translation stop sites, transcription terminators, splice signals, introns, and poly(A) signals. Types of promoters may include, without intending to be limiting, constitutive promoters, tissue-specific promoters, inducible promoters, repressible promoters, or leaky promoters. The term "operably linked" refers to a juxtaposition of components such that they are in a relationship permitting them to function in their intended manner. Exogenous DNAs described herein may be prepared using standard recombinant DNA technology and cloning techniques which are well known in the art. Preferably the exogenous DNA encodes the ATB$^{0,+}$ transporter.

Genetically engineered animals carrying the exogenous DNA on a single allele may be referred to herein as "hemizygous" animals while genetically engineered animals carrying the exogenous DNA on both alleles may be referred to herein as "homozygous" animals. For genes present on the X chromosome, male animals may exist as "hemizygous" when having one Y chromosome and one engineered chromosome. Animals that do not carry the exogenous DNA may be referred to herein as "wildtype" animals.

The present invention also includes methods of using the genetically engineered animals, such as for example, methods using an ATB$^{0,+}$ knock-out mouse to determine the efficacy of blocking ATB$^{0,+}$ function.

Genetically engineered animals and cells derived form such animals of the present invention may be used for testing the carcinogenicity of candidate compounds. The development of tumors upon exposure to a candidate compound is indicative of the candidate compound being carcinogenic.

The methods for testing the carcinogenicity of candidate compounds using transgenic mice as predictive models are known to the skilled person (see, for instance, Tennant et al., *Toxicol. Pathol.*, 2001, 29(Suppl.):51-59; Humble et al., *Oncogene*, 2005, 24:8217-8228, Eastin, *Environ. Health Perspect.*, 1998, 106(Suppl. 1):81-84; Tennant et al., *Environ. Health Perspect.*, 1995, 103:942-950). The use of genetically engineered animals of the present invention in such known methods addresses the continuing need for models to aid in the identification of carcinogenic compounds.

A control genetically engineered animal is an animal treated identically to a genetically engineered animal receiving the candidate compound, but the control only receives the solvent, or "vehicle," in which the candidate compound has been delivered. The solvents used for dissolving, suspending, and/or delivering the candidate compound are known to one of skill in the art and may include, among other solutions, water, acetone, ethanol, and dimethyl sulfoxide (DMSO). In some embodiments, the control animals are littermates of the experimental animals.

In another embodiment, the candidate compound may be administered to a cell isolated from genetically engineered animal of the present invention.

In vitro assays that are indicative of carcinogenicity are well known in the art and are herein referred to as transformation assays. Transformation assays include, but are not limited to, assays that determine cellular changes associated with tumor formation (such as increase proliferation, resistance to apoptosis, lack of cellular adhesion, increases in cellular migration) and assays that determine biochemical changes associated with tumor formation (such as increases hormone or growth factor production). In addition, the cells may be further tested for transformation in vivo through assays such as grafting experiments. In this instance, a reduction in transformation of the cell when compared to the control cell indicates that the candidate compound is an anti-carcinogen. A control cell is a cell that includes an exogenous DNA as described herein that has been treated identically to the cell receiving the carcinogen and the candidate anti-carcinogen compound, but the control receives only the vehicle.

Anti-proliferative compounds can be distinguished from anti-carcinogenic compounds easily and readily using molecular techniques known in the art. For example, both an anti-proliferative compound and an anti-carcinogenic compound would prevent cellular proliferation. However, it is likely that only the anti-carcinogenic compound would prevent transformation assays not directed to proliferation, such as colony formation in soft agar assays.

Genetically engineered animals and cells derived from such animals may be used for identifying and testing agents that modify ATB$^{0,+}$ transporter function. Modification can include inhibiting transporter function and enhancing. Transporter function. Such agents may be used as therapeutic agents in the treatment of cancer and other disease associated with altered ATB$^{0,+}$ transporter expression or function. The methods for screening for such candidate compounds using transgenic mice as predictive models are known to the skilled person, and include, but are not limited to, any of the methods described herein. In another embodiment, the candidate compound may be administered to a cell isolated from genetically engineered animal of the present invention.

The present invention is illustrated by the following examples. It is to be understood that the particular examples, materials, amounts, and procedures are to be interpreted broadly in accordance with the scope and spirit of the invention as set forth herein.

EXAMPLES

Example 1

ATB$^{0,+}$ as a Drug Target for Treatment of Cancer, Inflammation, and Ulcerative Colitis ATB$^{0,+}$ is an amino acid transporter. The basal expression of this transporter in normal tissues is low. But, the expression of the transporter is up-regulated several-fold in cancer, inflammation, and ulcerative colitis. The upregulation of the transporter in humans in colorectal cancer and cervical cancer (Gupta et al., 2005 Biochim. Biophys. Acta 1741:215-223; Gupta et al., 2006 Gynelcol. Oncol. 100:8-13). The present invention demonstrates the upregulation of the transporter in a mouse model of ulcerative colitis. This transporter transports 18 of the 20 amino acids in an energy-coupled manner. We postulate that tumors upregulate this transporter to get essential amino acids to support their growth. Even though there are several amino acid transporters, most of them have restricted substrate selectivity. In contrast, ATB$^{0,+}$ has broad substrate selectivity. Therefore, tumors can achieve their goal of getting all necessary amino acids by turning on one single gene, namely the gene (SLC6A14) which codes for this transporter. Specific high-affinity blockers of this transport system will be effective to prevent access of the tumor cells to essential amino acids and such high-affinity blockers will have therapeutic potential in cancer treatment. Since the transporter is expressed at low levels under normal conditions and in normal tissues, such blockers would have minimal or no effect on adjacent normal tissues, making the effect specific for tumor cells. The transporter also has another special feature. It transports arginine with high affinity. It is the only amino acid transporter which can transport arginine in an energy-dependent manner. Further, the upregulation of the transporter in inflammation and in ulcerative colitis likely serves as the basis for the enhanced production of nitric oxide under these conditions. These conditions are also associated with upregulation of iNOS. Increased activity of iNOS needs increased supply of arginine for NO production. The simultaneous and coordinated upregulation of the transporter and iNOS under inflammatory conditions likely leads to enhanced production of NO and the suppression of this process would have beneficial effects under these conditions. Effective blockade of the transporter function with specific high-affinity blockers would prevent arginine entry into inflamed tissues and thus prevent NO production via iNOS. The present invention includes a mouse model in which the gene coding for the transporter has been deleted. These he knockout mice are significantly resistant to chemically induced colitis (administration of dextran sulfate sodium in water). Studies are underway to evaluate whether the knockout mice are also resistant to genetically induced ulcerative colitis (1L-2 knockout), chemically induced inflammation (LPS injection), and genetically induced cancer ($APC^{min}$ mutation). We expect that mice which cannot upregulate the transporter due to ablation of the gene will be more resistant to cancer, inflammation, and ulcerative colitis. Small molecule inhibitors of this transporter will be therapeutically useful in the treatment of cancer, inflammation, and ulcerative colitis.

Example 2

Alpha-Methyl-L-Tryptophan and its Derivatives as Anti-Cancer Drugs

The amino acid transporter $ATB^{0,+}$ (SLC6A14) is upregulated in breast cancer, colon cancer, and cervical cancer. This has been shown this in primary tumors as well as in cancer cell lines. The transporter has very unique functional features which makes it ideal for tumor cells to depend on for satisfying their amino acid needs. Since tumor cells depend on this transporter to support their amino acid nutrition, blocking the function of this transporter has potential for cancer treatment. This example identifies a tryptophan derivative, known as alpha-methyl-tryptophan as a blocker of this transporter. The L-isomer of this compound is several-fold more potent as a blocker compared to the D-isomer. In vitro experiments demonstrate that treatment of transporter-positive cancer cell lines with this compound causes amino acid deprivation, and as a consequence, induces autophagy, cell cycle arrest, and apoptosis. Normal cells and transporter-negative cancer cells are not affected by the treatment under identical conditions, suggesting that the compound has no general toxic effects on cells. Since normal cells express little or no activity of this particular amino acid transporter, blocking the transporter offers a targeted therapy for killing tumor cells with no ill effects on adjacent normal cells. This example also shows that this tryptophan derivative is a competitive inhibitor of another amino acid transporter, known as LAT1, which is also overexpressed at least in certain types of cancer (e.g., glioblastoma), inhibition of this transporter by alpha-methyl-L-tryptophan is expected to cause amino acid starvation and hence to induce autophagy and apoptosis in LAT1-overexpressing cancers. Thus, this example shows that alpha-methyl-L-tryptophan by itself may serve as a potential anti-cancer drug. Further, this compound may also serve as a lead compound for chemical modification to enhance its therapeutic potency. Therefore, other chemical derivatives of alpha-methyl-L-tryptophan may have potential as anti-cancer drugs. In addition, if alpha-methyl-L-tryptophan is a transportable substrate for LAT1, $C^{11}$-labeled or derivatives of this compound with F18 could serve as a PET probe for detection of cancers which overexpress LAT1. Thus, alpha-methyl-L-tryptophan has great potential in cancer chemotherapeutics.

Example 3

Interaction of Tryptophan Derivatives with SLC6A14 ($ATB^{0,+}$) Reveals the Potential of the Transporter as a Drug Target for Cancer Chemotherapy $ATB^{0,+}$ [SLC6A14 (solute carrier family 6 member 14)] is an $Na^+/Cl^-$-coupled amino acid transporter whose expression is upregulated in cancer. 1-Methyltryptophan is an inducer of immune surveillance against tumour cells through its ability to inhibit indoleamine dioxygenase. In this example, we investigated the role of $ATB^{0,+}$ in the uptake of 1-methyltryptophan as a potential mechanism for entry of this putative anticancer drug into tumour cells. We show that 1-methyltryptophan is a transportable substrate for $ATB^{0,+}$. The transport process is $Na^+/Cl^-$-dependent with an $Na^+/Cl^-$/1-methyltryptophan stoichiometry of 2:1:1. Evaluation of other derivatives of tryptophan has led to identification of α-methyltryptophan as a blocker, not a transportable substrate, for $ATB^{0,+}$. $ATB^{0,+}$ can transport 18 of the 20 proteinogenic amino acids. α-Methyltryptophan blocks the transport function of $ATB^{0,+}$ with an $IC_{50}$ value of ~250 μM under conditions simulating normal plasma concentrations of all these 18 amino acids. These results suggest that α-methyltryptophan may induce amino acid deprivation in cells which depend on the transporter for their amino acid nutrition. Screening of several mammary epithelial cell lines shows that $ATB^{0,+}$ is expressed robustly in some cancer cell lines, but not in all; in contrast, non-malignant cell lines do not express the transporter. Treatment of $ATB^{0,+}$-positive tumour cells with α-methyltryptophan leads to suppression of their colony-forming ability, whereas $ATB^{0,+}$-negative cell lines are not affected. The blockade of $ATB^{0,+}$ in these cells with α-methyltryptophan is associated with cell cycle arrest. These studies reveal the potential of $ATB^{0,+}$ as a drug target for cancer chemotherapy.

$ATB^{0,+}$ is an amino acid transporter with special functional features (Ganapathy and Ganapathy, 2005, Curr. Drug Targets Immune Endocr. Metab. Disord. 5, 357-364). It transports 18 of the 20 proteinogenic amino acids, and its transport process is energized by three different driving forces, namely an $Na^+$ gradient, a $Cl^-$ gradient and membrane potential. Theoretically, this transporter has the ability to concentrate its substrates inside the cells more than 1000-fold. $ATB^{0,+}$ has been cloned from human and rodent tissues, and the function of the cloned transporter has been characterized in heterologous expression systems (Sloan and Mager, 1999, J. Biol. Chem. 274, 23740-23745; Nakanishi et al., 2001, J. Physiol. 532, 297-304; Uchiyama et al., 2008, J. Cell. Physiol. 214, 645-654). According to the HUGO (Human Genome Organisation) nomenclature, $ATB^{0,+}$ is identified as SLC6A14 (solute carrier family 6 member 14; i.e. the 14th member of the solute carrier gene family SLC6). Functional expression in *Xenopus laevis* oocytes has demonstrated that the transport process mediated by $ATB^{0,+}$ is electrogenic, associated with the transfer of net positive charge into the oocytes (Sloan and Mager, 1999, J. Biol. Chem. 274, 23740-23745; Nakanishi et al., 2001, J. Physiol. 532, 297-304). This transporter has therapeutic potential owing to its ability to transport a variety of pharmacological agents, including NOS (nitric oxide synthase) inhibitors (Hatanaka et al., 2001, J. Clin. Invest. 107, 1035-1043) and amino acid-based prodrugs of the antiviral agents acyclovir and ganciclovir (Hatanaka et al., 2004, J. Pharmacol. Exp. Ther. 308, 1138-1147; Umapathy et al., 2004, Pharm. Res. 21, 1303-1310). There is emerging evidence for tumour-associated up-regulation of $ATB^{0,+}$. The expression of this transporter is markedly induced in colorectal cancer (Gupta et al., 2005, Biochim. Biophys. Acta 1741, 215-223) and cervical cancer (Gupta et al., 2006, Gynecol. Oncol. 100, 8-13), and the up-regulation is demonstrable at the mRNA level as well as at the protein level. Since $ATB^{0,+}$ can transport almost all amino acids, the only exceptions being glutamate and aspartate, tumour cells can meet their increasing demand for amino acids simply by turning on a single gene (SLC6A14) coding for the transporter. It is therefore likely that the up-regulation of $ATB^{0,+}$ is not restricted to colorectal and cervical cancers. Since the basal expression of the transporter in different tissues is low under normal conditions, the tumour-associated up-regulation of the transporter can be exploited for tumour-specific delivery of anti-cancer drugs, leaving the adjacent natural cells unaffected by the effects of such drugs. The ability of the transporter to recognize structurally diverse pharmacological agents lends credence to its therapeutic potential in cancer treatment.

$ATB^{0,+}$ accepts tryptophan as a substrate with high affinity (Sloan and Mager, 1999, J. Biol. Chem. 274, 23740-23745; Nakanishi et al., 2001, J. Physiol. 532, 297-304). Since the transporter is up-regulated markedly in cancer, active cellular uptake of 1-methyltryptophan via the transporter may facilitate the inhibition of tumour-associated IDO in a specific manner. Thus, the present investigation was initiated to study the transport of 1-methyltryptophan and other tryptophan derivatives via $ATB^{0,+}$. These studies have not only shown that the IDO inhibitor 1-methyltryptophan is indeed a transportable substrate for $ATB^{0,+}$, but also identified α-methyltryptophan as a blocker of the transporter. Since the transporter is up-regulated in tumour cells, blocking of the transporter can be expected, in theory, to starve the tumour cells of amino acids, thus causing growth arrest. This was tested in breast cancer cell lines. These studies have shown that treatment of cancer cell lines overexpressing $ATB^{0,+}$ with α-methyltryptophan does induce growth arrest, suggesting that the transporter can be exploited as a potential drug target for cancer chemotherapy with identification of high-affinity blockers of the transporter.

Materials and Methods

Materials.

[$^3$H]Glycine (specific radioactivity=30 Ci/mmol), D-[$^3$H]serine (specific radioactivity=20 Ci/mmol) and L-[$^{14}$C]valine (specific radioactivity=260 mCi/mmol) were purchased from Moravek Biochemicals (Brea, Calif., U.S.A.). Tryptophan and its derivatives, including 1-methyl-DL-tryptophan, 1-methyl-L-tryptophan, 1-methyl-D-tryptophan and α-methyl-DL-tryptophan, were from Sigma. The numbers in tryptophan derivatives refer to the position of the substitutions (methyl or hydroxy group) in the indole ring, with nitrogen in the ring being position 1 and the carbon atoms in the ring being counted counter-clockwise. α-Methyltryptophan has the methyl group substitution at the α-carbon of the aliphatic side chain. N-Acetyltryptophan has the acetyl group substitution at the α-amino group in the side chain. The mouse $ATB^{0,+}$ cDNA was cloned from a colon cDNA library and its transport function has been established in previous studies (Nakanishi et al., 2001, J. Physiol. 532, 297-304). The human $ATB^{0,+}$ cDNA was cloned from an MCF7 cell (a human mammary epithelial cancer cell line) cDNA library and the functional identity of the clone has been established by its ability to mediate $Na^+$- and $Cl^-$-coupled transport of glycine and D-serine in a heterologous expression system using mammalian cells. Human LAT1 cDNA was cloned from a human placental cell line and its functional identity has been established previously in a mammalian cell heterologous expression system with co-expression of 4F2hc (Prasad et al., 1999, Biochem. Biophys. Res. Commun. 255, 283-288).

Functional Expression of Cloned $ATB^{0,+}$ and LAT1/4F2Hc in HRPE Cells (Human Retinal Pigment Epithelial Cells).

Mouse and human $ATB^{0,+}$ and human LAT1/4F2hc cDNAs were expressed functionally in an HRPE cell line using the vaccinia virus expression technique as described previously (Nakanishi et al., 2001, J. Physiol. 532, 297-304). This procedure involves infection of the cells with a recombinant vaccinia virus carrying the gene for T7 RNA polymerase, followed by Lipofectin®-mediated transfection of the cells with plasmid DNA in which the cDNA insert is under the control of T7 promoter. Glycine was used as the substrate for $ATB^{0,+}$. Transport of 10 µM glycine (radiolabelled glycine, 0.05 µM; unlabelled glycine, 9.95 µM) in cDNA-transfected cells was measured at 37° C. for 30 min, representing linear uptake rates. The transport buffer was 25 mM Hepes/Tris (pH 7.5) containing 140 mM NaCl, 5.4 mM KCl, 1.8 mM $CaCl_2$, 0.8 mM $MgSO_4$ and 5 mM glucose. Transport was terminated by aspiration of the transport buffer followed by three washes with 2 ml of ice-cold transport buffer. The cells were lysed with 0.5 ml of 1% SDS in 0.2 M NaOH and the lysate was used for determination of radioactivity. Interaction of tryptophan and its derivatives with the transporter was assessed by monitoring the ability of these compounds to inhibit $ATB^{0,+}$-mediated glycine transport. In initial experiments, we compared glycine uptake between cells transfected with vector alone and cells transfected with $ATB^{0,+}$ cDNA to assess the relative levels of constitutive glycine uptake rate. These experiments revealed that glycine uptake in vector-transfected cells was less than 3% of glycine uptake in cDNA-transfected cells. Therefore all subsequent studies were done only with cDNA-transfected cells, considering the constitutively expressed glycine uptake as negligible.

L-Valine was used as the substrate for LAT1/4F2hc. Transport of L-[$^{14}$C]valine (0.75 µM) was measured in vector-transfected cells and in cDNA-transfected cells in parallel in the same buffer described above, but with a 5 min. incubation instead of a 30 min incubation. Parallel uptake measurements in vector-transfected cells and cDNA-transfected cells were necessary because of a significant constitutive expression of system L activity in these cells (Prasad et al., 1999, Biochem. Biophys. Res. Commun. 255, 283-288). Co-expression of human LAT1 cDNA and human 4F2hc cDNA in these cells increased the activity for valine transport by 3-fold, showing that the transport activity in vector-transfected cells was ~30% of the transport activity in cDNA-transfected cells. The interaction of tryptophan derivatives with LAT1/4F2hc was evaluated by assessing the effects of these compounds (1 mM) on the transport of valine in vector-transfected cells and in cDNA-transfected cells and then calculating the cDNA-specific transport activity in the presence and absence of these derivatives.

Functional Expression of $ATB^{0,+}$ in *X. Laevis* oocytes.

Capped cRNA from the cloned mouse or human $ATB^{0,+}$ cDNA was synthesized using the mMESSAGE mMACHTNE kit (Ambion, Austin, Tex., U.S.A.). Mature oocytes (stage IV or V) from *X. laevis* were injected with 50 ng of cRNA. Uninjected oocytes served as controls. The oocytes were used for electrophysiological studies 3-6 days after cRNA injection. Electrophysiological studies were performed by the two-microelectrode voltage-clamp method (Nakanishi et al., 2001, J. Physiol. 532, 297-304). Oocytes were superfused with an NaCl-containing buffer (100 mM NaCl, 2 mM KCl, 1 mM $MgCl_2$, 1 mM $CaCl_2$, 3 mM Hepes, 3 mM Mes and 3 mM Tris, pH 7.5), followed by the same buffer containing tryptophan derivatives. The membrane potential was clamped at −50 mV. The differences between the steady-state currents measured in the presence and absence of substrates were considered as the substrate-induced currents. In the analysis of the saturation kinetics of substrate-induced currents, the kinetic parameter $K_{0.5}$ (i.e. substrate concentration necessary for induction of half-maximal current) was calculated by fitting the values of the substrate-induced currents to the Michaelis-Menten equation. The $Na^+$ and $Cl^-$ activation kinetics of substrate-induced currents were analysed by measuring the substrate-specific currents in the presence of increasing concentrations of $Na^+$ (concentration of $Cl^-$ kept constant at 100 mM) or in the presence of increasing concentrations of $Cl^-$ (concentration of $Na^+$ kept constant at 100 mM). In these experiments, the composition of the superfusion buffer was modified to contain 2 mM potassium gluconate, 1 mM $MgSO_4$ and 1 mM calcium gluconate in place of KCl, $MgCl_2$ and $CaCl_2$ respectively. The data from these experiments were analysed by the Hill equation to determine the Hill coefficient (h; number of $Na^+$ and $Cl^-$ ions involved in the activation process). The kinetic parameters were determined by using the commercially available computer program Sigma Plot, version 6.0 (SPSS, Chicago, Ill., U.S.A.). Uninjected oocytes were used to determine the currents induced by tryptophan derivatives due to entry via transporters that may be constitutively expressed in the oocytes. At a concentration of 2.5 mM, the currents induced by these compounds were in the range of 0-3 nA in uninjected oocytes. These currents were less than 2% of the corresponding currents induced in $ATB^{0,+}$ cRNA-injected oocytes. Therefore the endogenous currents associated with the constitutively expressed transporters were not considered in the analysis of kinetic parameters of $ATB^{0,+}$ transport activity.

Mammary Epithelial Cell Lines and their Culture.

MCF7, T-47D, ZR-75.1, MB-231, MB-361 and MB-453 cell lines were purchased from the American Tissue Culture Collection (ATCC), (Manassas, Va., USA) and cultured in DMEM (Dulbecco's modified Eagle's medium) containing 10% (v/v) fetal bovine serum, 100 units/ml penicillin, 100 μg/ml streptomycin, 2 mM glutamine and 1 mM pyruvate. HMEC (human mammary epithelial cell) (Clonetics, Walkersville, Md., U.S.A.) and MCF10A (A.T.C.C.) cell lines were cultured in Complete Mammary Epithelial Growth medium (Cambrex, Walkersville, Md., U.S.A.) containing 100 ng/ml cholera toxin and 2 mM pyruvate. HBL100 cell line (originally obtained from Dr. Sukumar, Johns Hopkins University, Baltimore, Md., U.S.A.) was cultured in DMEM/F12 medium containing 10% fetal bovine serum, 100 units/ml penicillin, 100 μg/ml streptomycin, 2 mM glutamine and 1 mM pyruvate. Among the nine cell lines examined in the present study, HMEC, HBL100 and MCF10A are non-malignant because these cell lines do not form a tumour when xenografted into nude mice. In contrast, the other remaining six cell lines (MCF7, T-47D, ZR-75.1, MDA-MB231, MDA-MB361 and MDA-MB453) are malignant based on their ability to form tumour when xenografted in nude mice.

Uptake Measurements in Cell Lines.

Cells were seeded and grown in 24-well culture plates to confluency and used for uptake measurements. Radiolabelled glycine or D-serine was used as the substrate to determine the transport function of $ATB^{0,+}$. Uptake measurements were routinely made in an NaCl-containing buffer (25 mM Hepes/Tris buffer, pH 7.4, 140 mM NaCl, 5.4 mM KCl, 1.8 mM $CaCl_2$, 0.8 mM $MgSO_4$ and 5 mM glucose). Ion dependence of the transport process was evaluated by studying the uptake activity in buffers of varying compositions. NaCl in the uptake buffer was replaced iso-osmotically with NMDG (N-methyl-D-glucamine) chloride to prepare an $Na^+$-free buffer, and with sodium gluconate to prepare a $Cl^-$-free buffer. Linear uptake rates were determined by employing a 10 min incubation period, based on time course experiments. $Na^+$-activation kinetics was analysed by studying the uptake rates in the presence of varying concentrations of $Na^+$ (2.5-140 mM) in the uptake buffer with $Cl^-$ concentration kept constant at 140 mM. This was done by replacing NaCl with appropriate concentrations of NMDG. $Cl^-$-activation kinetics was analysed by studying the uptake rates in the presence of varying concentrations of $Cl^-$ (2.5-100 mM) in the uptake buffer with $Na^+$ concentration kept constant at 140 mM. This was done by replacing NaCl with appropriate concentrations of sodium gluconate. Uptake data for $Na^+$- and $Cl^-$-activation kinetics were analysed using the Hill equation, and values for $K_{0.5}$ for $Na^+$ and $Cl^-$ and for the Hill coefficient (h) were determined by linear and non-linear regression methods. A commercially available software program (Sigma Plot, version 6.0; SPSS) was used for this purpose. Substrate specificity of the uptake process was evaluated by monitoring the effects of unlabelled amino acids (5 mM) on the uptake of radiolabelled glycine or D-serine (5 μM: radiolabelled substrate, 0.05 μM; unlabelled substrate, 4.95 μM).

The kinetic nature of inhibition of D-serine uptake by α-methyl-DL-tryptophan was investigated in MCF7 cells by monitoring the uptake at increasing concentrations of D-serine (range, 50-2000 μM) in the absence and presence of 100 μM α-methyl-DL-tryptophan. The kinetic parameters were calculated by linear regression (Eadie-Hofstee plots) and the values were confirmed by non-linear regression.

Analysis of $ATB^{0,+}$ Expression.

For the analysis of the expression of $ATB^{0,+}$ mRNA, RNA prepared from the cell lines was used. RNA (2 μg) was reverse-transcribed using the GeneAmp® PCR system (Roche). HPRT1 (hypoxanthine-guanine phosphoribosyltransferase 1) mRNA was used as an internal control. Human $ATB^{0,+}$-specific PCR primers were designed based on the nucleotide sequences available in GenBank® Nucleotide Sequence Database (upstream primer: 5'-GAAG-GAGAAAGTGTCGGCTTCA-3'; SEQ ID NO:1; downstream primer: 5'-TACCACCTTGCCAGACGATTTG-3'; SEQ ID NO:2). For the analysis of $ATB^{0,+}$ protein, Western blot was used. Cell lysates were prepared by sonication in 10 mM Tris/HCl buffer (pH 7.6) containing protease inhibitors (50 mM NaF, 0.2 mM vanadate, 1 mM PMSF, 5 μg/ml aprotinin, 1 μg/ml pepstatin A and 2 μg/ml leupeptin) and 1% Triton X-100. Protein (50 μg) was fractionated by SDS/PAGE gels and transferred on to a Protran nitrocellulose membrane (Schleicher and Schull). Membranes were blocked with 5% (w/v) non-fat dried skimmed milk powder, exposed to primary antibody at 4° C. overnight followed by treatment with an appropriate secondary antibody, conjugated to horseradish peroxidase, at room temperature for 1 hour, and developed by SuperSignal Western-blotting system (Pierce). The details of the primary antibody have been published previously (Gupta et al., 2005, Biochim. Biophys. Acta 1741, 215-223; Gupta et al., 2006, Gynecol. Oncol. 100, 8-13).

Expression of IDO, LAT1, GLYT1 and GLYT2.

The expression of IDO, LAT1, GLYT1 and GLYT2 in the breast epithelial cell lines was examined by RT-PCR (reverse transcription-PCR). There are two isoforms of IDO in humans, namely IDO1 and IDO2. In addition, there is another related enzyme, known as TDO (tryptophan-2,3-dioxygenase), which also mediates the breakdown of tryptophan. We investigated the expression of IDO1, IDO2 and TDO by RT-PCR in nine different HMEC cell lines (three non-malignant cell lines and six malignant cell lines). The primer pairs used were as follows: 5'-GCAAATGCAAGAACGGGACAC-3' (upstream; SEQ ID NO:3) and 5'-TCAGGGAGACCA-GAGCTTTCACAC-3' (downstream; SEQ ID NO:4) for IDO1, 5'-ACAGGACCACTTGCTGACAGCTTA-3' (upstream; SEQ ID NO:5) and 5'-ACGTGGGTGAAGGAT-TGACTCCAA-3' (downstream; SEQ ID NO:6) for IDO2, and 5'-AAACCTCCGTGCTTCTCAGACAGT-3' (upstream; SEQ ID NO:7) and 5'-TGAAGTCCAAGGCTGT-CATCGTCT-3' (downstream; SEQ ID NO:8) for TDO. The primer pairs for the various amino acid transporters were as follows: 5'-GTGTGATGACGCTGCTCTACG-3' (upstream; SEQ ID NO:9) and 5'-GATGATGGTGAAGCCGATGC-3' (downstream; SEQ ID NO:10) for human LAT1, 5'-CAACT-GTGCCACCAGCGTCTA-3' (upstream; SEQ ID NO:11) and 5'-ACGCCCAAGGTCACATAGGTCT-3' (downstream; SEQ ID NO:12) for human GLYT1, and 5'-GACGAGTTTC-CCAAGTACCTAC-3' (upstream; SEQ NO:13) and 5'-CAGTTAGGATAGCGGTAAGAGC-3' (downstream; SEQ ID NO:14) for human GLYT2. HPRT was used as the internal control.

Colony Formation Assay.

The colony formation assay was performed as described previously (Thangaraju et al., 2006, Cancer Res. 66, 11560-11564). Mammary epithelial cells were seeded on to 6-well plates (10000 cells per well) in DMEM. After 24 hours, cells were exposed to varying concentrations of α-methyl-DL-tryptophan or 1-methyl-DL-tryptophan for 2 weeks, changing medium every 2 days. Cells were washed with PBS and fixed in 100% (v/v) methanol for 30 min followed by staining with KaryoMAX Giemsa stain for one hour. The wells were washed with water and dried overnight at room temperature. Finally, the dye in the wells was dissolved with 1% SDS in 0.2 M NaOH for one hour, and the attenuance of the released dye was measured at 630 nm.

Cell Cycle Analysis.

MCF10A (an $ATB^{0,+}$-negative non-malignant cell line), MCF7 (an $ATB^{0,+}$-positive malignant cell line) and MDA-MB453 (an $ATB^{0,+}$-negative malignant cell line) cells were cultured in 6-well plates in a regular culture medium in the presence or absence of α-methyl-DL-tryptophan (2.5 mM) for 24, 48 and 72 hours. Cells were fixed in 50% (v/v) ethanol, treated with 0.1% sodium citrate, 1 mg/ml RNase A and 50 μg/ml propidium iodide, and subjected to FACS (Becton Dickinson FACSCalibur™) analysis. The amount of DNA in these cells, detected as chromosome content by propidium iodide binding, was used to identify cells in various stages of cell cycle: G1/G0, 2N; S, 2-4 N; G2/M, 4N (where N is the normal chromosome content).

Results

Interaction of Tryptophan Derivatives with Cloned $ATB^{0,+}$ Expressed Heterologously in HRPE Cells.

We first studied the interaction of 1-methyltryptophan and other derivatives of tryptophan with the cloned mouse $ATB^{0,+}$ by functionally expressing the clone in HRPE cells. HRPE cells exhibit very low basal glycine uptake activity, and the uptake increases more than 30-fold when mouse $ATB^{0,+}$ cDNA is expressed in this cell line. The cDNA-induced glycine uptake has all the characteristic features of $ATB^{0,+}$; it is Na$^+$- and Cl$^-$-dependent and is inhibitable by neutral as well as cationic amino acids. Thus this experimental system is ideal to examine the interaction of 1-methyltryptophan and other tryptophan derivatives with a cloned $ATB^{0,+}$. FIG. 1A describes the effects of tryptophan and its various derivatives on $ATB^{0,+}$-specific glycine uptake. The uptake was inhibited by L-tryptophan, D-tryptophan, 1-methyl-DL-tryptophan, 4-methyl-DL-tryptophan, 5-methyl-DL-tryptophan, 6-methyl-DL-tryptophan, α-methyl-DL-tryptophan, 5-hydroxy-L-tryptophan and L-tryptophan methyl ester (glycine concentration, 10 μM; inhibitor concentration, 1 mM). In contrast, N-acetyl-L-tryptophan and 5-hydroxytryptamine (serotonin) were not able to inhibit the uptake. $ATB^{0,+}$ is known to transport many, but not all, of its substrates in L-form and in D-form (Hatanaka et al., 2002, Biochem. Biophys. Res. Commun. 291, 291-295). We have shown that alanine, serine, methionine, leucine and tryptophan are transported via $ATB^{0,+}$ in both L- and D-form, while the remaining amino acid substrates are recognized by the transporter only in L-form (Hatanaka et al., 2002, Biochem. Biophys. Res. Commun. 291, 291-295). The present studies with L-tryptophan and D-tryptophan corroborate these earlier findings. Since 1-methyl-DL-tryptophan was able to inhibit $ATB^{0,+}$-specific glycine uptake, we compared the inhibitory potencies of the L- and D-isomers of 1-methyltryptophan. Even though both racemic forms were able to inhibit the uptake, there was a marked difference in their potencies. 1-Methyl-L-tryptophan was at least 35-fold more potent than 1-methyl-D-tryptophan as an inhibitor of $ATB^{0,+}$-mediated glycine uptake. The $IC_{50}$ values for the L- and D-isomers were 23±5 and 780±225 μM respectively.

Interaction of Tryptophan Derivatives with Cloned $ATB^{0,+}$ Expressed Heterologously in X. Laevis oocytes.

The above studies with the mammalian cell expression system have focused on the interaction of 1-methyltryptophan and other tryptophan derivatives with $ATB^{0,+}$ by examining the effects of these compounds on the transporter-mediated glycine uptake. These studies have shown convincingly that 1-methyltryptophan interacts with $ATB^{0,+}$, with the L-isomer having much higher affinity for the transporter than the D-isomer. However, these studies have not shown whether or not 1-methyltryptophan is actually a transportable substrate for $ATB^{0,+}$. It is possible that 1-methyltryptophan inhibits $ATB^{0,+}$-mediated glycine uptake simply by blocking the interaction of glycine with the substrate-binding site of the transporter, rather than by actually competing with glycine for the transport process. Competition experiments described above do not have the ability to distinguish between transportable substrates and blockers. We wanted to know whether 1-methyltryptophan can actually be transported by $ATB^{0,+}$. For this, we used the X. laevis oocyte expression system. Since the transport process mediated by $ATB^{0,+}$ is electrogenic, exposure of $ATB^{0,+}$-expressing oocytes to transportable substrates will induce an inward current in an Na$^+$- and Cl$^-$-dependent manner. Exposure of the same oocytes to blockers will interfere with currents induced by transportable substrates, but will not induce currents by themselves. This experimental system thus has the ability to differentiate between a transportable substrate and a blocker. Therefore we expressed the cloned mouse $ATB^{0,+}$ in Xenopus oocytes by injecting the corresponding cRNA, and functional expression of the transporter in the oocytes was confirmed by glycine-induced inward currents. Water-injected oocytes did not show any glycine-inducible currents, indicating that there was no detectable basal electrogenic glycine transport in these oocytes. Once the expression of $ATB^{0,+}$ was confirmed, we investigated the transport of various tryptophan derivatives via the transporter by monitoring inward currents. Most of the derivatives that inhibited $ATB^{0,+}$-mediated glycine uptake in mammalian cells showed inward currents in $ATB^{0,+}$-expressing oocytes (FIG. 1B). The magnitude of the currents varied from compound to compound. Importantly, 1-methyl-DL-tryptophan induced marked currents. 5-Hydroxy-L-tryptamine (serotonin) and N-acetyl-L-tryptophan, which did not inhibit $ATB^{0,+}$-mediated glycine uptake in mammalian cells, did not induce currents in the oocyte expression system.

The only notable exception was α-methyl-DL-tryptophan. This derivative was a potent inhibitor of ATB$^{0,+}$-mediated glycine uptake in mammalian cells, but it failed to induce currents in the oocytes, suggesting that this derivative may be a blocker of ATB$^{0,+}$. These results showed for the first time that 1-methyl-DL-tryptophan is a transportable substrate for ATB$^{0,+}$.

Figure 2:
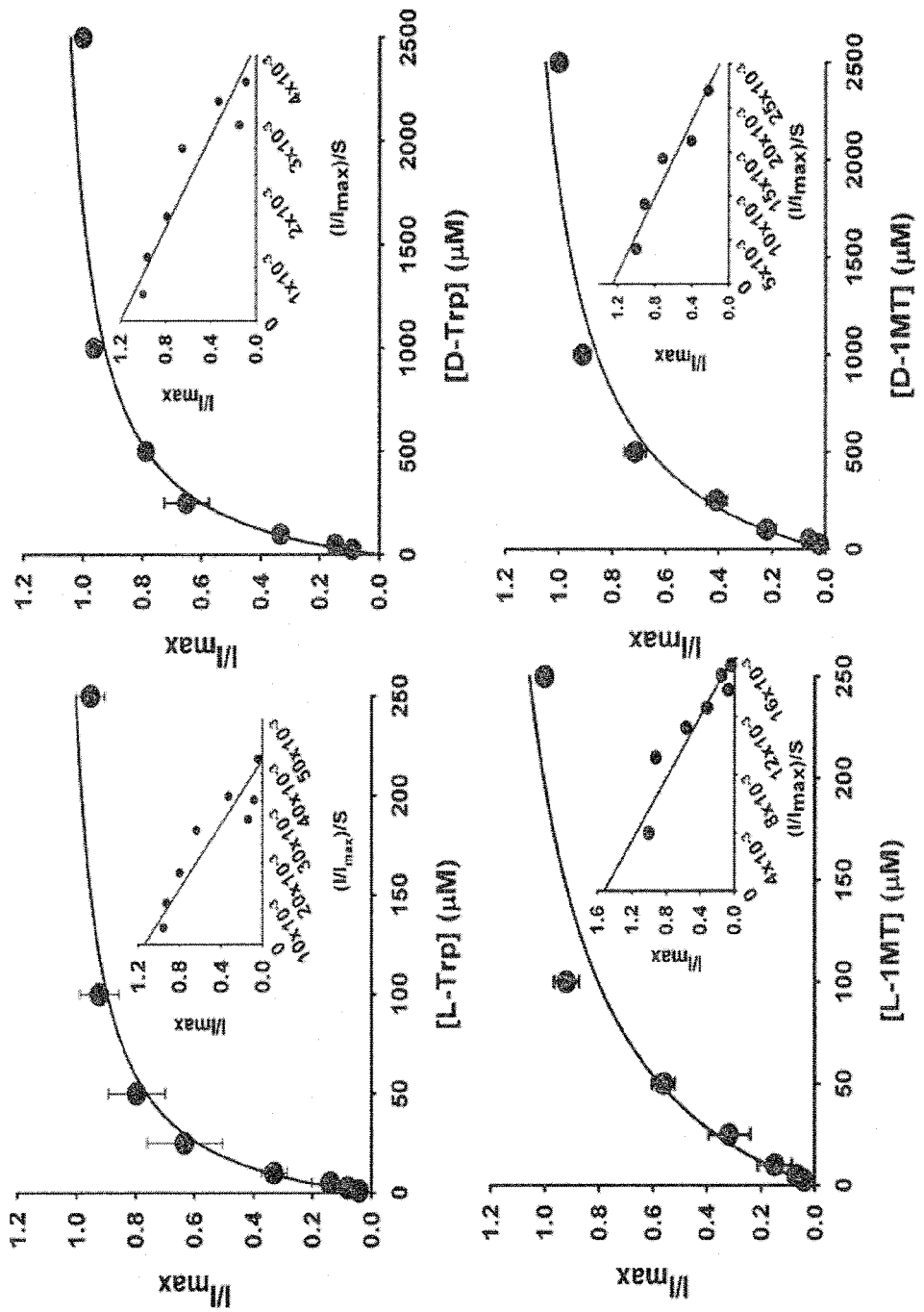
FIG. 2 shows saturation kinetics for $ATB^{0,+}$-mediated transport of L- and D-isomers of tryptophan and 1-methyltryptophan. Mouse $ATB^{0,+}$, expressed heterologously in *X. laevis* oocytes, was used in the present study. Transport function was monitored by measuring inward currents induced by increasing concentrations of L- and D-isomers of tryptophan and 1-methyltryptophan. (1 MT). Measurements were made in the presence of NaCl under voltage-clamp conditions. Since expression levels varied from oocyte to oocyte, data were normalized by taking the current induced by maximal substrate concentration in each oocyte as 1, and then calculating the currents induced at other concentrations as a fraction of this value. Results represent means±S.E.M. for three independent experiments in three different oocytes.
Figure 3:
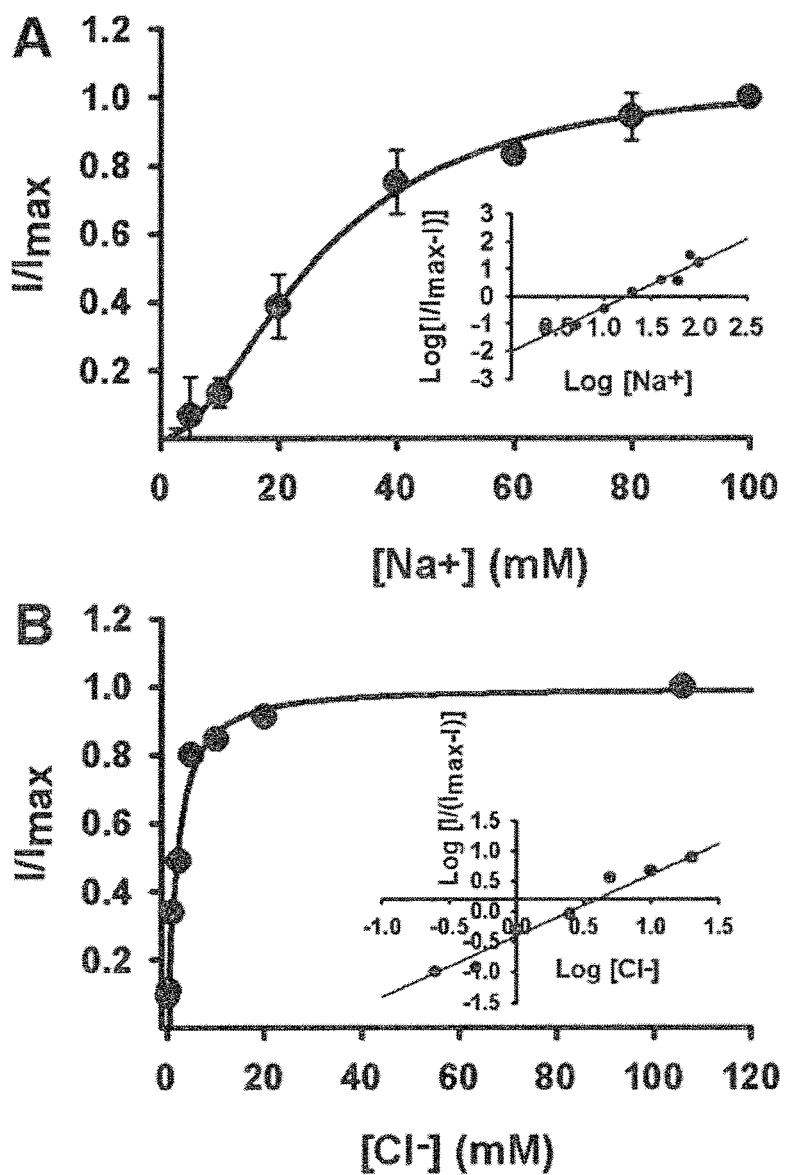
FIG. 3 shows $Na^+$- and $Cl^-$-activation kinetics for $ATB^{0,+}$-mediated transport of 1-methyl-L-tryptophan. Transport of 1-methyl-L-tryptophan (1 mM) via mouse $ATB^{0,+}$ was monitored in X. laevis oocytes following heterologous expression of the transporter.

Since this experimental approach allows us to monitor directly the actual transport of 1-methyltryptophan via ATB$^{0,+}$, we performed saturation kinetics for the L- and D-isomers of this derivative and compared the data with those obtained for the L- and D-isomers of tryptophan (FIG. 2). The currents induced by all four compounds were saturable in ATB$^{0,+}$-expressing oocytes. The Michaelis constants for the L- and D-isomers of tryptophan were 26±3 and 288±48 μM respectively. The corresponding values for the L- and D-isomers of 1-methyltryptophan were 93±16 and 462±78 μM respectively. We then analysed the Na$^+$-activation kinetics and Cl$^-$-activation kinetics for 1-methyl-L-tryptophan. This was done by monitoring the inward currents induced by 1 mM 1-methyl-L-tryptophan in the presence of increasing concentrations of Na$^+$ (with Cl$^-$ concentration fixed at 100 mM) or Cl$^-$ (with Na$^+$ concentration fixed at 100 mM) (FIG. 3). The Na$^+$-activation kinetics showed a sigmoidal relationship between Na$^+$ concentration and inward currents. The Hill coefficient (h) was 1.9±0.2, indicating that two Na$^+$ are involved in the activation process. The Michaelis constant ($K_{0.5}$) for Na$^+$ was 27±2 mM. Similar experiments with Cl$^-$ showed a hyperbolic relationship between Cl$^-$ concentration and inward currents. The Hill coefficient was 1.2±0.2 and the Michaelis constant was 2.1±0.3 mM. These results show that one Cl$^-$ is involved in the activation process. Since 1-methyl-L-tryptophan is zwitterionic under the experimental conditions (pH 7.5), the stoichiometry suggests that the transport process is associated with transfer of one net positive charge into the oocytes per transport cycle. This explains the electrogenic nature of the transport process and the induction of inward currents under voltage-clamp conditions.

α-Methyl-DL-Tryptophan as a Blocker of ATB$^{0,+}$.

Figure 4:
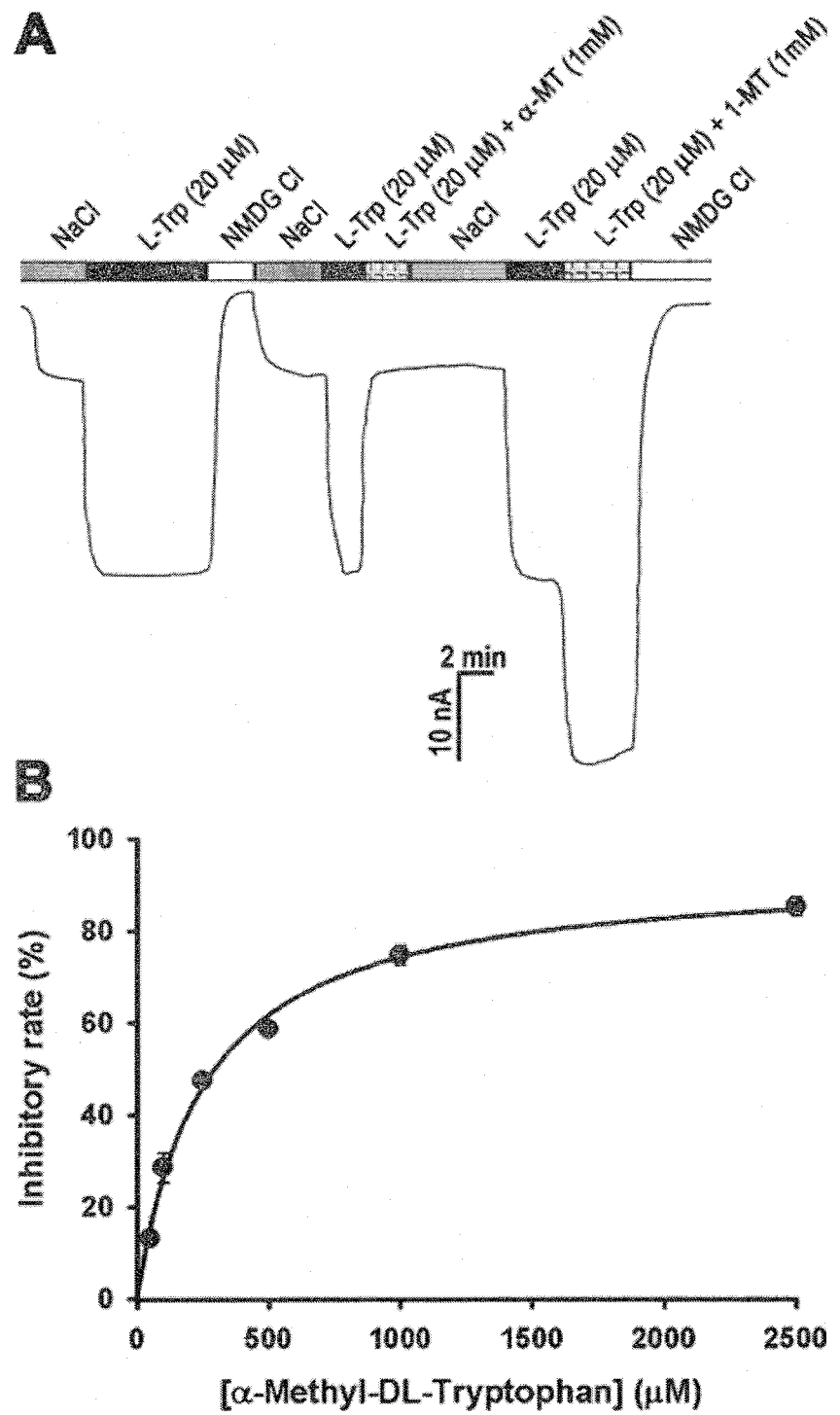
FIG. 4 shows an evaluation of α-methyl-DL-tryptophan as a blocker of $ATB^{0,+}$. These studies were done with human $ATB^{0,+}$. The transporter was expressed in X. laevis oocytes by cRNA injection.

Even though α-methyl-DL-tryptophan was able to inhibit ATB$^{0,+}$-mediated glycine uptake in HRPE cells (FIG. 1A), it failed to induce inward currents in ATB$^{0,+}$-expressing *Xenopus* oocytes (FIG. 1B). This indicates that this tryptophan derivative may function as a blocker of ATB$^{0,+}$. We performed additional studies to confirm whether α-methyl-DL-tryptophan is indeed an ATB$^{0,+}$ blocker. For this, we used the *Xenopus* oocyte expression system in which the transport function of heterologously expressed human ATB$^{0,+}$ was monitored by measuring inward currents induced by L-tryptophan under sub-saturating conditions (L-tryptophan concentration, 20 μM). Simultaneous addition of a transportable substrate along with 20 μM L-tryptophan will increase the magnitude of the inward currents, whereas simultaneous addition of a blocker along with 20 μM L-tryptophan will decrease the magnitude of the inward currents. FIG. 4A describes the results from these experiments. Exposure of ATB$^{0,+}$-expressing oocytes to 20 μM L-tryptophan induced ~30 nA inward currents. But when the same oocytes were exposed to L-tryptophan (20 μM) and α-methyl-DL-tryptophan (1 mM) simultaneously, the L-tryptophan-induced currents were blocked completely. This was in contrast with what happened with simultaneous exposure to L-tryptophan and 1-methyl-DL-tryptophan. When 1-methyl-DL-tryptophan was present at 1 mM along with 20 μM L-tryptophan, the magnitude of inward currents was greater than that with 20 μM L-tryptophan alone. This was expected because 1-methyl-DL-tryptophan is a transportable substrate, and when 1 mM of this compound is added to the medium along with L-tryptophan at a sub-saturating concentration (20 μM), the transporter mediates the influx of L-tryptophan as well as 1-methyl-DL-tryptophan, resulting in an increase in the magnitude of inward currents.

These studies with α-methyl-DL-tryptophan as a blocker of ATB$^{0,+}$ were carried out with L-tryptophan at sub-saturating concentrations. We then wanted to determine the potency of this blocker to interfere with the transporter under conditions that simulate those in vivo, with all naturally occurring amino acids present at normal physiological concentrations. ATB$^{0,+}$ accepts all proteinogenic amino acids except for glutamate and aspartate. Therefore, using the *Xenopus* oocyte heterologous expression system, we monitored the transport activity of human ATB$^{0,+}$ in the presence of an amino acid mixture consisting of 18 different amino acids, each at its respective physiological concentration found in plasma (Glew et al., 2004, Clin. Chim. Acta 342, 179-185) (Table 1). Inward currents were detected under these conditions in oocytes expressing human ATB$^{0,+}$. Under similar conditions, the currents induced in water-injected oocytes were less than 5% of the currents observed in ATB$^{0,+}$-expressing oocytes, demonstrating that the currents observed in ATB$^{0,+}$-expressing oocytes were almost completely due to the transporter. We then monitored the ability of α-methyl-DL-tryptophan to block the inward currents induced by the same mixture of amino acids in oocytes expressing human ATB$^{0,+}$ (FIG. 4B). There was a dose-dependent increase in the magnitude of inhibition, with maximal inhibition (~85%) observable at 2.5 mM α-methyl-DL-tryptophan. The concentration of the blocker necessary to elicit 50% of maximal inhibition was 255±24 μM.

TABLE 1

Concentrations of amino acids used in oocyte superfusion medium to simulate normal plasma

| Amino Acid | Concentration (μM) |
|---|---|
| Alanine | 440 |
| Arginine | 150 |
| Asparagine | 115 |
| Cysteine | 10 |
| Glutamine | 440 |
| Glycine | 280 |
| Histidine | 50 |
| Isoleucine | 55 |
| Leucine | 175 |
| Lysine | 140 |
| Methionine | 25 |
| Phenylalanine | 105 |
| Proline | 215 |
| Serine | 215 |
| Threonine | 90 |
| Tryptophan | 10 |
| Tyrosine | 60 |
| Valine | 175 |

Expression of IDO and ATB$^{0,+}$ in Non-Malignant and Malignant Mammary Epithelial Cell Lines.

Figure 5:
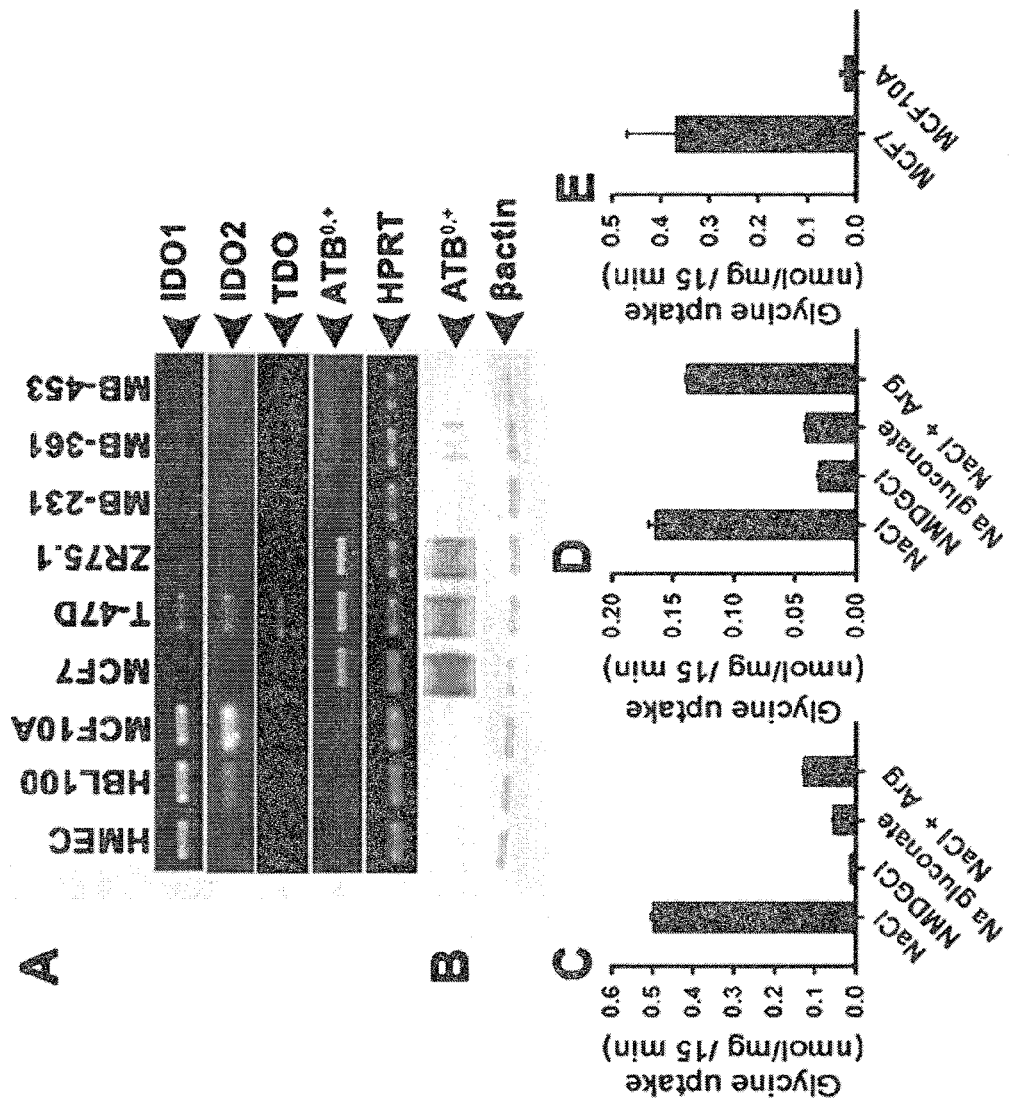
FIG. 5 shows expression of IDO1, IDO2, TDO and $ATB^{0,+}$ in mammary epithelial cell lines.

The studies described so far have shown that 1-methyl-L-tryptophan is a transportable substrate for ATB$^{0,+}$ and that α-methyl-DL-tryptophan is a blocker of ATB$^{0,+}$. 1-Methyl-L-tryptophan is an inhibitor of IDO and has been shown to be effective in animal models as a chemotherapeutic agent for the treatment of certain cancers by activation of immune function against tumour cells (Hou et al., 2007, Cancer Res. 67, 792-801; Sharma et al., 2007, J. Clin. Invest. 117, 2570-2582). This tryptophan derivative is currently in clinical trials for evaluation of its efficacy in cancer treatment in humans. It is already known that the ability of 1-methyl-L-tryptophan to inhibit IDO underlies its therapeutic potential as an anticancer agent, but the mechanism of cellular entry of this compound in tumour cells or in tumour-associated immune cells to gain access to its therapeutic target IDO has not been investigated. Since the present studies have shown that ATB$^{0,+}$ functions as a transporter for 1-methyl-L-tryptophan, we wanted to investigate the relevance of ATB$^{0,+}$ to the cellular entry of 1-methyl-L-tryptophan and consequent inhibition of intracellular IDO. For this, we needed a cell-culture model system in which IDO and the transporter are co-expressed. We screened nine different mammary epithelial cell lines, three of them being normal non-malignant cell lines (HMEC, HBL100 and MCF10A) and the remaining being malignant cell lines (MCF7, T-47D, ZR-75.1, MDA-MB231, MDA-MB361 and MDA-MB453). Surprisingly, the expression of IDO1 and IDO2 was greater in non-malignant cell lines than in malignant cell lines (FIG. 5A). There was little or no expression of these enzymes in malignant cell lines except for the T-47D cell line, which showed appreciable expression of both isoforms of IDO. IDO was expressed at low levels in some cell lines, but there was no malignancy-associated up-regulation of this enzyme. However, ATB$^{0,+}$ was expressed robustly in three malignant cell lines (MCF7, T-47D and ZR-75.1), while the expression of the transporter was either very low or undetectable in non-malignant cell lines and the remaining three malignant cell lines. This was evident at the level of mRNA expression (FIG. 5A) and protein expression (FIG. 5B). We confirmed this differential expression of ATB$^{0,+}$ by monitoring its transport function. The data for glycine uptake in ATB$^{0,+}$-positive MCF7 cell line and ATB$^{0,+}$-negative MCF10A cell line are given in FIGS. 5C-5E. The uptake of glycine was detectable in both cell lines, but only in MCF7 cells the uptake was Na$^+$-dependent, Cl$^-$-dependent and arginine-inhibitable. These are signature characteristics of ATB$^{0,+}$. Even though glycine uptake in MCF10A was Na$^+$/Cl$^-$-dependent, the inability of arginine to compete with glycine uptake excludes ATB$^{0,+}$ as the transporter responsible for the uptake. The arginine-sensitive glycine uptake, which is a measure of ATB$^{0,+}$-specific transport function, is given in FIG. 5E. While the transport function was robust in MCF7 cells, the activity was barely detectable in MCF10A cells, corroborating the data on the differential expression of ATB$^{0,+}$ in these cells. In subsequent studies, we have shown that GLYT1, which is also an Na$^+$/Cl$^-$-dependent transport system for glycine but is insensitive to arginine inhibition, is responsible for glycine uptake observed in MCF10A cells. RT-PCR studies showed that MCF7 cells also express GLYT1 mRNA, but not GLYT2 mRNA. However, glycine uptake via GLYT1 should not be inhibitable by arginine. Since most of the glycine uptake in MCF7 cells is arginine-sensitive, we conclude that contribution of GLYT1 to glycine uptake in this cell line is very low.

Figure 6:
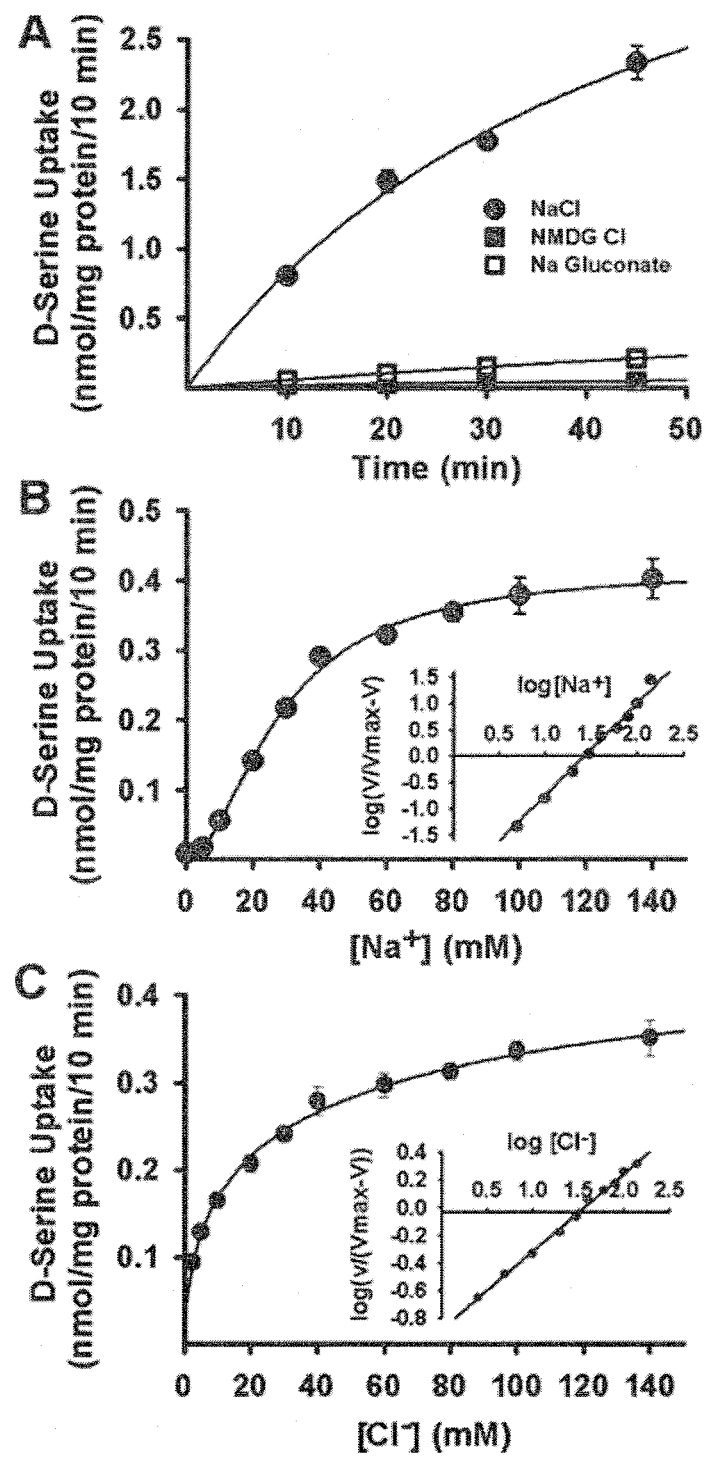
FIG. 6 shows features of D-serine uptake in MCF7 cells.
Figure 7:
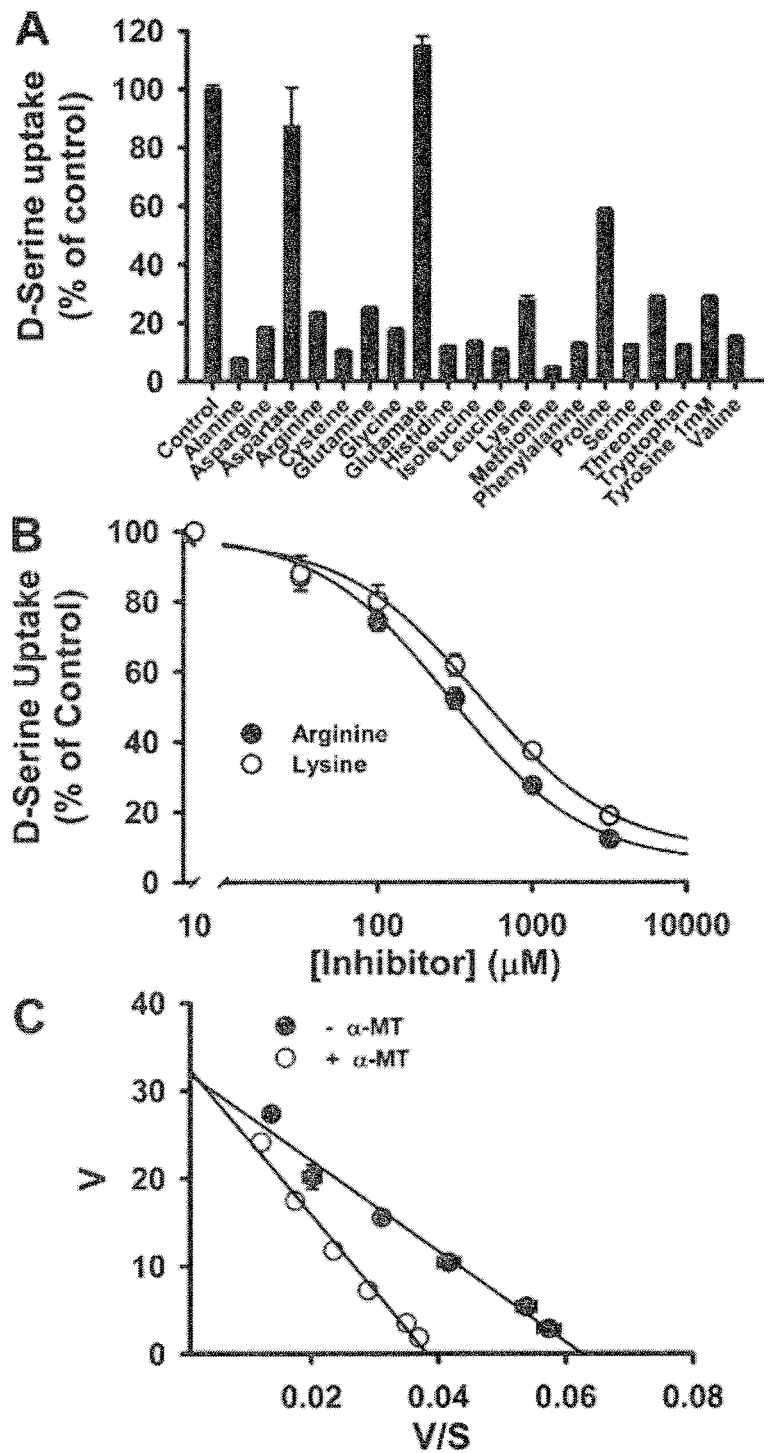
FIG. 7 shows amino acid selectivity and inhibition by α-methyl-DL-tryptophan of D-serine uptake system in MCF7 cells.

Since glycine serves as a substrate for three different Na$^+$/Cl$^-$-coupled transport systems, namely ATB$^{0,+}$, GLYT1 and GLYT2, we studied the transport of D-[$^3$H]serine, a known substrate for ATB$^{0,+}$ with little interaction with the other two transporters (Hatanaka et al., 2002, Biochem. Biophys. Res. Commun. 291, 291-295), in these cell lines (FIG. 6). The uptake of D-serine in MCF7 cells was obligatorily dependent on Na$^+$ and Cl$^-$. The uptake was inhibitable by neutral and cationic amino acids (FIG. 7A). Arginine and lysine inhibited the uptake, with IC50 values in the range of 250-500 µM (FIG. 7B). These results confirm the expression of ATB$^{0,+}$ in MCF7 cells. We employed a similar experimental strategy to detect specifically the transport function of ATB$^{0,+}$ in the remaining seven cell lines. These studies showed that ATB$^{0,+}$ transport function is detectable only in MCF7, T-47D and ZR-75.1 cells and not in others, corroborating the data on mRNA and protein expression. Since MCF7 cells express ATB$^{0,+}$ constitutively, we investigated the inhibition of D-serine uptake by 1-methyl-DL-tryptophan, 1-methyl-L-tryptophan and 1-methyl-D-tryptophan to corroborate our earlier findings on the interaction of these compounds with the transporter in heterologous expression systems. 1-Methyl-DL-tryptophan was able to inhibit D-serine uptake in a dose-dependent manner in this cell line; the IC$_{50}$ value for inhibition by 1-methyl-DL-tryptophan was 221±40 µM. When the L- and D-isomers of 1-methyltryptophan were examined individually, it was found that the L-isomer competed with D-serine much more effectively than the D-isomer. The IC$_{50}$ value for inhibition by the L-isomer was at least 15-fold lower compared with the D-isomer (86±11 µM versus 1580±180 µM). These results show that ATB$^{0,+}$ interacts with 1-methyltryptophan in a cell line that expresses the transporter constitutively. We also investigated the effect of α-methyl-DL-tryptophan on D-serine uptake in MCF7 cells. The uptake was inhibitable by this blocker of ATB$^{0,+}$. The inhibition was competitive (FIG. 7C). In the absence of the blocker, the values for Kt and Vmax for D-serine uptake were 517±38 µM and 32.4±1.5 nmol/mg of protein per 15 min respectively. The corresponding values were 869±52 µM and 33.3±1.4 nmol/mg of protein per 15 min in the presence of α-methyl-DL-tryptophan (100 µM). Thus the inhibition of D-serine uptake by α-methyl-DL-tryptophan was associated with a decrease in substrate affinity without affecting the maximal velocity.

Evidence for the Potential Use of α-Methyl-DL-Tryptophan as a Tumour-Suppressive Agent from its Ability to Block ATB$^{0,+}$.

Figure 8:
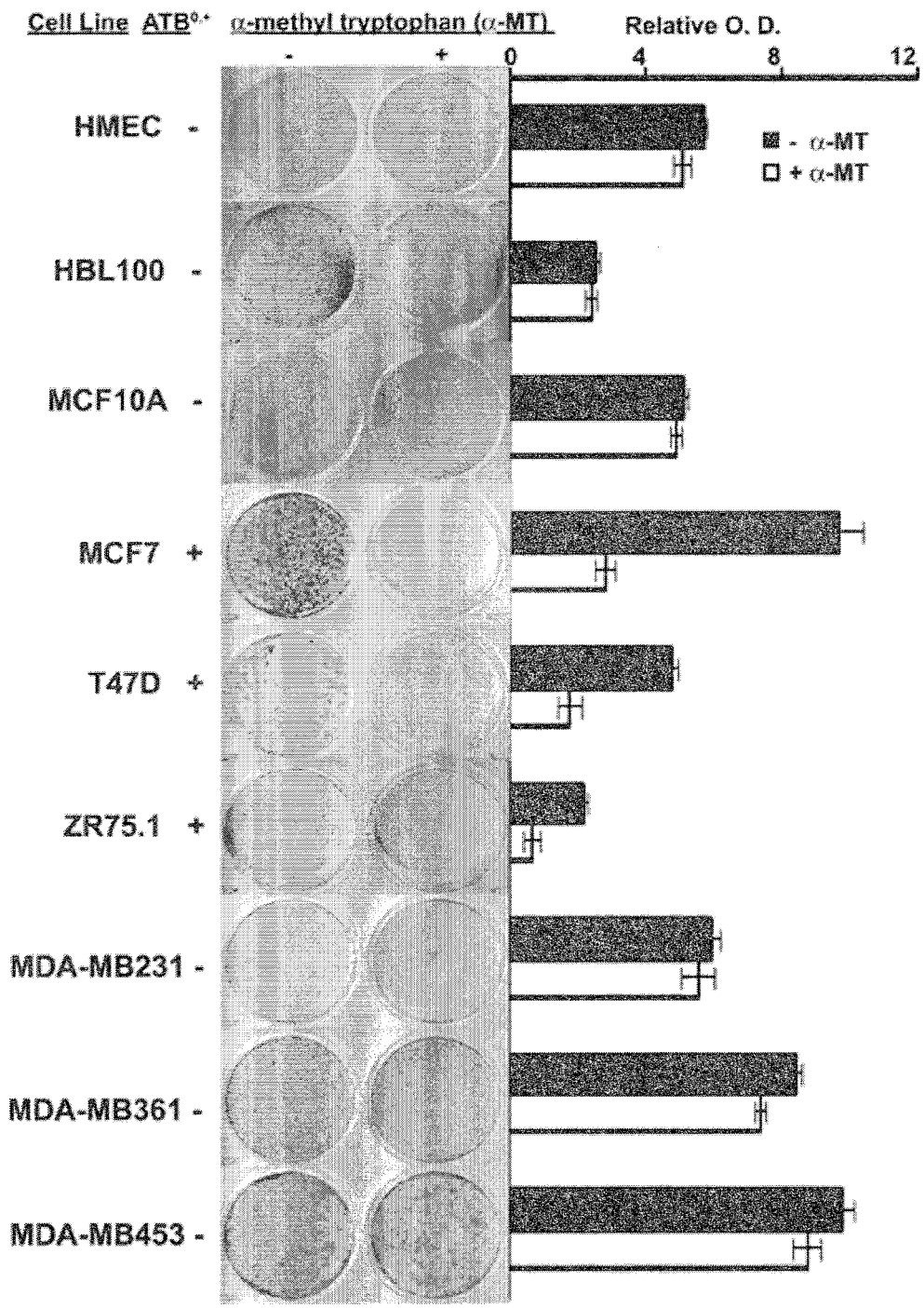
FIG. 8 shows influence of α-methyl-DL-tryptophan on the colony-forming ability of mammary epithelial cell lines. Nine different mammary epithelial cell lines were used in the present study. The cells were treated with 2.5 mM α-methyl-DL-tryptophan for two weeks as described in the Materials and methods section. At the end of the two-week period, the dishes were photographed, and then the intensity of the KaryoMAX Giemsa stain was quantified. The photograph is from a representative experiment; similar results were obtained from two other experiments. Values for attendance were from all three experiments. HMEC, HBL100 and MCF10A are non-malignant and $ATB^{0,+}$-negative cell lines; MCF7, T47D and ZR75.1 are malignant and $ATB^{0,+}$-positive cell lines; MDA-MB231, MDA-MB361 and MDA-MB453 are malignant but $ATB^{0,+}$-negative cell lines.

The present studies have identified α-methyl-DL-tryptophan as a blocker of ATB$^{0,+}$ and also have shown that the compound is able to block the transport of amino acids via ATB$^{0,+}$ under conditions that stimulate those in vivo in terms of amino acid concentrations. We have also shown that the transporter is up-regulated in certain tumour cell lines, but not in all tumour cell lines, and that the expression of the transporter is almost undetectable in non-malignant cell lines. This provides a unique opportunity to examine the potential of α-methyl-DL-tryptophan to deprive ATB$^{0,+}$-positive tumour cells of essential amino acids and evaluate the consequences. For this, we treated the human mammary epithelial cell lines with 2.5 mM α-methyl-DL-tryptophan in the presence of regular culture medium for 12 days in clonogenic assay and quantified the colony formation for each cell line in the presence and absence of α-methyl-DL-tryptophan (FIG. 8). We found no effect of α-methyl-DL-tryptophan on HMEC, HBL100 and MCF10A cells, which are non-malignant and ATB$^{0,+}$-negative in their ability to form colonies. Similarly, the blocker had little or no effect on colony formation in MDA-MB231, MDA-MB361 and MDA-MB453 cell lines, which are malignant but express no or very low levels of ATB$^{0,+}$. In contrast, the three cell lines that are malignant and ATB$^{0,+}$-positive (MCF7, T-47D and ZR-75.1) were affected markedly by α-methyl-DL-tryptophan in the clonogenic assay. At 2.5 mM, the blocker was able to inhibit colony formation by 60-75% in these three cell lines. A dose-response study with MCF7 cells using the same assay conditions gave an IC$_{50}$ value of 160±15 µM for the inhibition.

Figure 9:
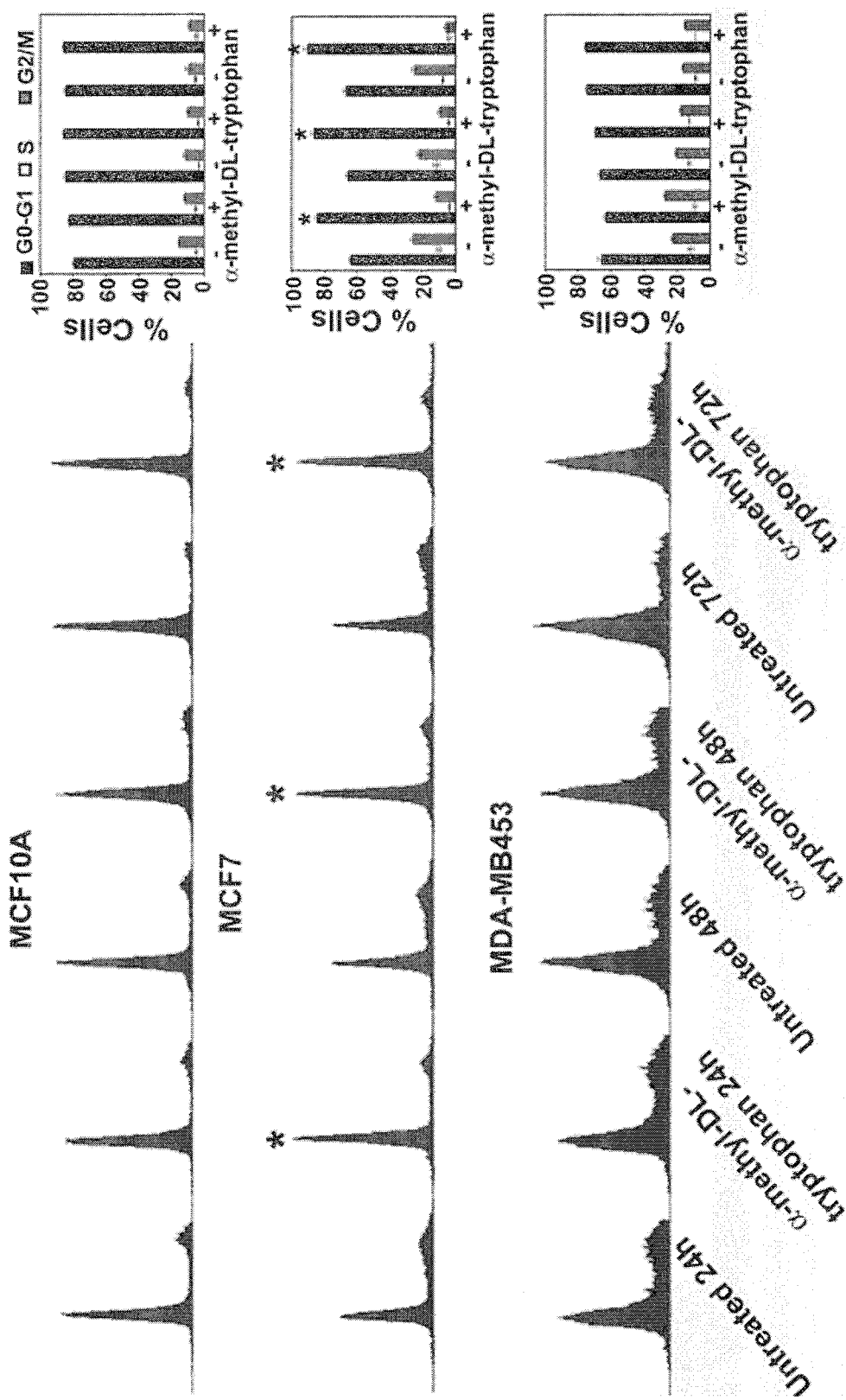
FIG. 9 shows influence of α-methyl-DL-tryptophan on cell-cycle profile of MCF10A, MCF7 and MDA-MB453 cell lines. MCF10A (non-malignant and $ATB^{0,+}$-negative), MCF7 (malignant and $ATB^{0,+}$-positive) and MDA-MB453 (malignant and $ATB^{0,+}$-negative) cells were treated with α-methyl-DL-tryptophan (2.5 mM) for 24, 48 and 72 hours. Cells were then subjected to FACS analysis to determine the percentage of cells in each stage of the cell cycle. Quantitative data are from two independent experiments, each done in triplicate. *$P<0.001$, compared with untreated cells at the corresponding time period.

Since treatment with α-methyl-DL-tryptophan suppressed colony formation in malignant cell lines in an ATB$^{0,+}$-dependent manner, we investigated the influence of this treatment on cell cycle to determine which stage of the cycle is affected. We used three different cell lines in this experiment:

MCF10A (non-malignant and ATB$^{0,+}$-negative), MCF7 (malignant and ATB$^{0,+}$-positive) and MDA-MB453 (malignant and ATB$^{0,+}$-negative) (FIG. 9). Analysis of the progression of cells through cell cycle under control conditions and in the presence of α-methyl-DL-tryptophan showed that the treatment with the blocker had no effect on cell cycle in MCF10A and MDA-MB453 cell lines that do not express ATB$^{0,+}$. In contrast, the treatment affected the cell cycle progression in the ATB$^{0,+}$-positive MCF7 cell line. The cells were arrested at G1/G0 stage to a significant extent when treated with α-methyl-DL-tryptophan. This was evident from the relative percentage of cells that were in G1/G0- and S-phases. In the absence of the blocker, the percentage of MCF7 cells in G1/G0- and S-phases was 63±1 and 10±2 respectively. But when the cells were treated with α-methyl-DL-tryptophan for 24 hours, the corresponding values were 82±1 and 3±1 respectively. The treatment-induced increase in the percentage of the cells in G1/G0-phase and decrease in the percentage of the cells in S-phase were statistically significant ($P<0.001$). Similar results were obtained with treatment for 48 and 72 hours. These results show that α-methyl-DL-tryptophan prevents MCF7 cells from progressing from G1-phase to S-phase. Since this effect is not seen with MCF10A and MDA-MB453 cells, we conclude that the observed effect in MCF7 cells is due to blockade of ATB$^{0,+}$ transport function.

Interaction of Tryptophan Derivatives with Cloned Human LAT1 and Expression of the Transporter in Breast Cancer Cell Lines.

Figure 10:
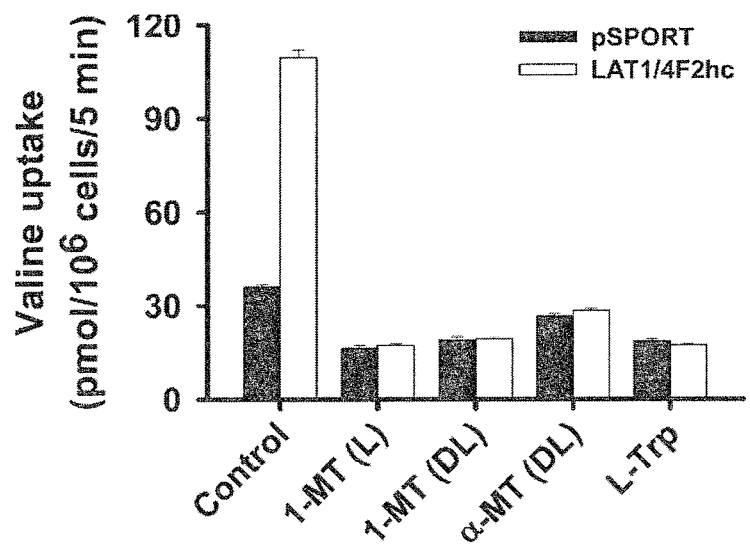
FIG. 10 shows inhibition of LAT1 transport function by tryptophan derivatives. Human LAT1 cDNA was co-expressed with human 4F2hc cDNA in HRPE cells by the vaccinia virus expression system. Vector (pSPORT)-transfected cells served as the control. Activity of LAT1 was monitored by measuring the uptake of L-[$^{14}$C]valine (0.75 μM) with a 5 minute incubation. When present, the concentration of tryptophan derivatives was 1 mM. 1-MT, 1-methyl-L-tryptophan; 1-MT (DL), 1-methyl-DL-tryptophan; α-MT (DL), α-methyl-DL-tryptophan. Results represent means±S.E.M. for six determinations from two independent expression experiments.

LAT1/4F2hc is a heterodimeric amino acid transporter that functions as an obligatory amino acid exchanger (Kanai and Endou, 2001, Curr. Drug Metab. 2, 339-354; Ganapathy et al., "Cellular uptake of amino acids: system and regulation." In Metabolic and Therapeutic Aspects of Amino Acids in Clinical Nutrition (Cynober, L. A., ed.), 2nd edn, 2004, pp. 63-78, CRC Press, Boca Raton, Fla.). LAT1 is the transporter and 4F2hc is necessary for proper targeting of the transporter to the plasma membrane. The activity of LAT1 is not dependent on Na$^+$. Aromatic amino acids such as tryptophan and branched-chain amino acids such as valine are high-affinity substrates for this transporter. The expression of LAT1 is increased in certain tumours, especially in the brain and lung (Kanai and Endou, 2001, Curr. Drug Metab. 2, 339-354; Fuchs and Bode, 2005, Semin. Cancer Biol. 15, 254-266). Therefore we investigated the interaction of tryptophan derivatives with cloned human LAT1. For this, we co-expressed human LAT1 cDNA and human 4F2hc cDNA in HRPE cells using the vaccinia virus expression technique and used L-valine as the substrate to monitor the transporter activity. The uptake of valine increased in cDNA-transfected cells by 3-fold compared with vector-transfected cells (FIG. 10). In the presence of tryptophan, 1-methyl-L-tryptophan, 1-methyl-DL-tryptophan and α-methyl-DL-tryptophan (1 mM), the cDNA-induced valine uptake was abolished completely, demonstrating that these tryptophan derivatives interact with the transporter.

Figure 11:
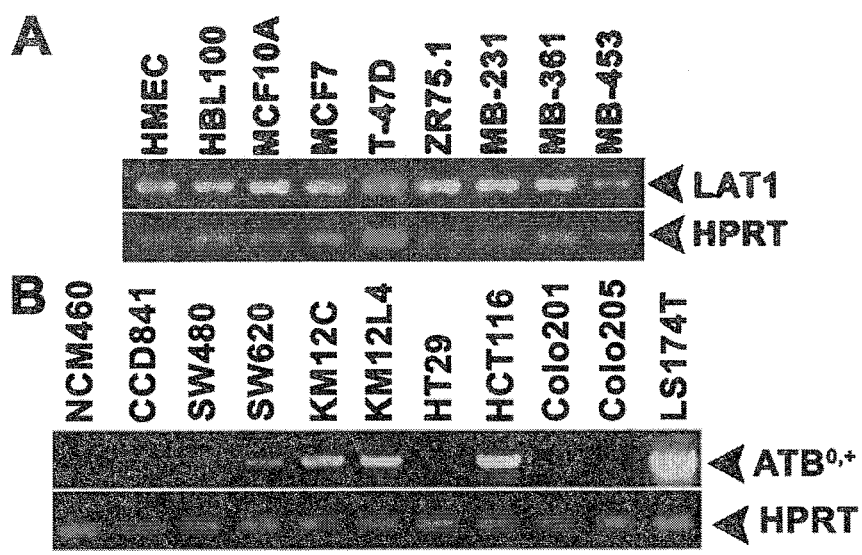
FIG. 11 shows RT-PCR analysis of the expression of LAT1 mRNA in non-malignant and malignant HMEC cell lines (FIG. 11A) and ATB$^{0,+}$ mRNA in non-malignant and malignant human colon epithelial cell lines (FIG. 11B)

Since α-methyl-DL-tryptophan inhibits LAT1 effectively, the question arises as to the role of LAT1 in the ability of this tryptophan derivative to cause growth arrest in certain breast cancer cell lines. Therefore we studied the expression of LAT1 in non-malignant and malignant mammary epithelial cell lines to see if the transporter expression is enhanced in cancer cell lines (FIG. 11A). These studies showed that LAT1 is expressed in these cell lines, but there was no difference in the expression levels between non-malignant and malignant cell lines. This was not surprising because enhanced expression of LAT1 in cancer is tissue-specific (Fuchs and Bode, 2005, Semin. Cancer Biol. 15, 254-266). Previous studies have shown that LAT1 expression is not altered in breast cancer (Fuchs and Bode, 2005, Semin. Cancer Biol. 15, 254-266). Our studies confirm these previous findings. The ability of α-methyl-DL-tryptophan to cause growth arrest is seen only in three malignant mammary epithelial cell lines (MCF7, T-47D and ZR75.1) and not in the non-malignant cell lines (HMEC, HBL100 and MCF10A) and the other three malignant cell lines (MDA-MB231, MDA-MB361 and MDA-MB453). Since the expression of LAT1 is not different among all these nine cell lines, inhibition of LAT1 by α-methyl-DL-tryptophan is not responsible for the observed ability of this tryptophan derivative to block growth arrest in MCF7, T-47D and ZR75.1 cell lines. These findings further support our conclusion that the growth arrest caused by α-methyl-DL-tryptophan in these three cell lines occurs through blockade of ATB$^{0,+}$ function.

Expression of ATB$^{0,+}$ in Colon Cancer Cell Lines.

To determine whether the expression of ATB$^{0,+}$ is induced in other malignant cell lines, we measured the levels of ATB$^{0,+}$ mRNA in two non-malignant human colonic epithelial cell lines (NCM460 and CCD841) and nine malignant human colonic epithelial cell lines (SW480, SW620, KM12C, KM12L4, HT29, HCT116, Colo201, Colo205 and LS174T) (FIG. 11B). We found robust up-regulation of ATB$^{0,+}$ expression in five out of nine malignant cell lines. This suggests that the induction of ATB$^{0,+}$ expression is not unique to certain breast cancer cell lines; the phenomenon is seen also in other malignant cell types.

Discussion

This example shows that 1-methyltryptophan is indeed a transportable substrate for ATB$^{0,+}$. Recently, we reported on the expression of ATB$^{0,+}$ in colon cancer metastasis in the liver (Gupta et al., 2005, Biochim. Biophys. Acta 1741, 215-223). While the expression was robust in metastasized cancer cells, there was a significant up-regulation of the transporter expression in liver cells surrounding the metastasized cancer cells. Based on these findings, we speculated that cancer cells may secrete factors that might act on surrounding non-cancerous cells to induce ATB$^{0,+}$ expression (Gupta et al., 2005, Biochim. Biophys. Acta 1741, 215-223). Therefore it would be interesting to examine the expression of this transporter in tumour-associated immune cells that exhibit up-regulation of IDO. The present findings that ATB$^{0,+}$ transports 1-methyl-DL-tryptophan also suggest that the transporter might play a role in the oral bioavailability of this compound. ATB$^{0,+}$ is expressed in the intestinal tract, especially in the colon (Hatanaka et al., 2002, Biochem. Biophys. Res. Commun. 291, 291-295). The intestinal/colonic absorption of this drug may be facilitated at least partly by this transporter.

The identification of a tryptophan derivative as a blocker of ATB$^{0,+}$ was an unexpected and surprising outcome of the present study. α-Methyl-DL-tryptophan blocks the transport function of ATB$^{0,+}$ without being itself transported. This is the first compound to be identified as a blocker of this transporter and we conclude that α-methyl-DL-tryptophan is not a transportable substrate, based on the findings that the compound did not induce detectable inward currents in ATB$^{0,+}$-expressing oocytes. Comparison of uptake of radiolabelled α-methyl-DL-tryptophan between control oocytes and ATB$^{0,+}$-expressing oocytes will provide data to demonstrate unequivocally whether or not this tryptophan derivative is a transportable substrate. While the present example demonstrates that α-methyl-DL-tryptophan is most likely a blocker of ATB$^{0,+}$, the potency of this compound to block the transport function of ATB$^{0,+}$ is weak. With amino acid concentrations simulating in vivo conditions, the compound was able to cause 50% blockage of $ATB^{0,+}$ transport function only at ~250 μM.

We were intrigued by the finding that one of the tryptophan derivatives may actually be a blocker of $ATB^{0,+}$, because specific blockers of this transporter may have potential in cancer chemotherapy. Since tumour cells up-regulate $ATB^{0,+}$ to meet their increasing demands for amino acids, blockade of the transport function of $ATB^{0,+}$ may offer an effective means to starve the tumour cells of essential amino acids. $ATB^{0,+}$-expressing tumour cells may suffer from amino acid deprivation when treated with α-methyl-DL-tryptophan with consequent cell-cycle arrest. The results of the present studies illustrate two important points. First, α-methyl-DL-tryptophan is not toxic to human mammary epithelial cell lines, whether or not the cells are malignant, as long as there is no $ATB^{0,+}$ contributing to amino acid nutrition. Secondly, α-methyl-DL-tryptophan is able to arrest colony formation in tumour cells in a $ATB^{0,+}$-specific manner. These results demonstrate the potential of $ATB^{0,+}$-specific blockers as anticancer agents in tumours that overexpress $ATB^{0,+}$. Thus the present studies reveal the potential of $ATB^{0,+}$ as a drug target in cancer treatment. High-affinity blockers of this transporter may have therapeutic use in preventing tumour progression. Since the transporter is expressed at very low levels in most cells under normal conditions and marked up-regulation of the transporter is seen in cancer, blockade of the transport function of $ATB^{0,+}$ may have a tumour-specific effect, without affecting the surrounding normal cells. The present studies have shown that α-methyl-DL-tryptophan is an inhibitor of the transport function of not only $ATB^{0,+}$ but also LAT1. Increased expression of LAT1 has been demonstrated in certain cancers but not in all. But there are significant differences between these two transporters which are relevant to their potential as therapeutic targets for cancer treatment. $ATB^{0,+}$ is highly concentrative with a unique ability to mediate uphill transport of amino acids into cells because of the driving forces involved in the transport process. In contrast, LAT1 is not active. Furthermore, the transport function of LAT1 is bidirectional. It functions as an obligatory amino acid exchanger, a characteristic more suitable for equilibration of amino acids inside the cells in relation to the extracellular milieu than for concentrative influx of amino acids into cells. Cancer cells have a unique need for increased influx of amino acids to support their growth. The functional differences between $ATB^{0,+}$ and LAT1 highlight the potential of the former as a promising drug target for cancer treatment.

This example is also as described in Karunakaran et al., "Interaction of tryptophan derivatives with SLC6A14 ($ATB^{0,+}$) reveals the potential of the transporter as a drug target for cancer chemotherapy," *Biochem. J.* (2008) 414:343-355.

Example 4

Up-Regulation of $ATB^{0,+}$ in Cancer

Figure 12:
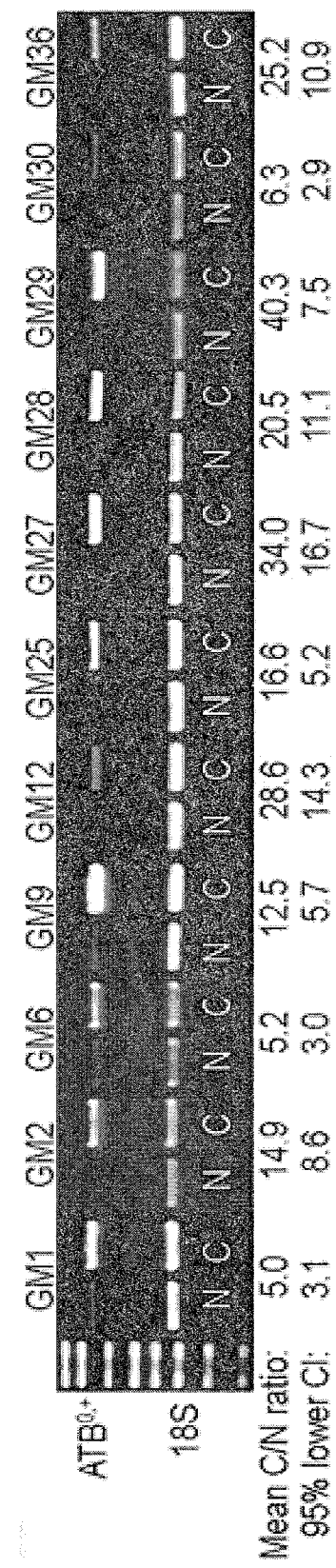
FIG. 12 shows expression of ATB$^{0,+}$ in colorectal cancer. Patients with colorectal cancer showed a 22.9±3.0-fold increase in ATB$^{0,+}$ mRNA levels in tumor tissue over corresponding normal tissue in all patients. N, normal; C, cancer; GM1, GM2, GM6, GM9, GM12, GM25, GM27, GM28, GM29, GM30, GM36, individual patients; 18S RNA as an internal control.
Figure 13:
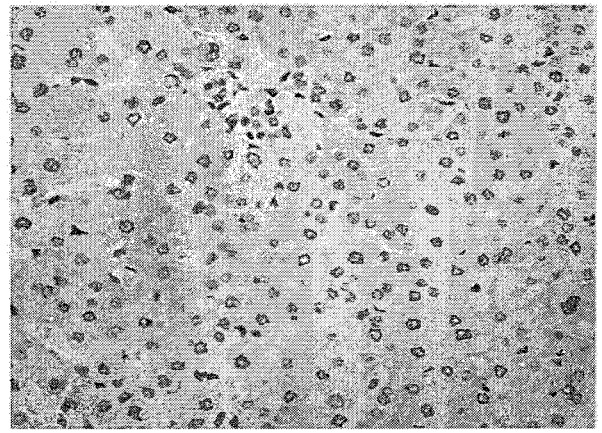
FIG. 13 shows expression of ATB$^{0,+}$ in colon cancer metastasis in liver and lymph node.
Figure 13:
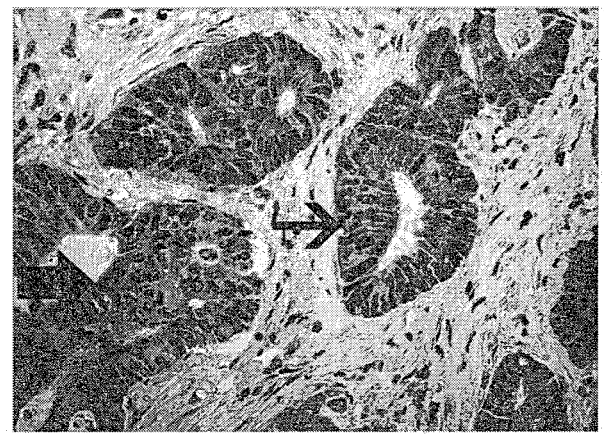
Figure 13:
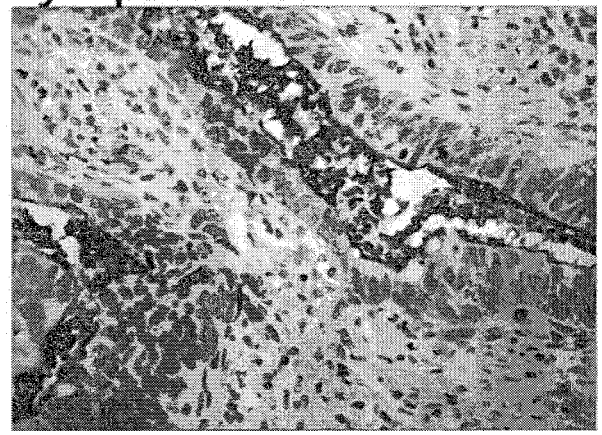

Until recently, only three amino acid transporters have been shown to be up-regulated in cancer. These are ASCT2, LAT1, and xCT. However, the substrate selectivity of all these three transporters is very narrow, supplying only a selective few amino acids to tumor cells. Furthermore, all these transporters function as obligatory exchangers, meaning that influx of certain amino acids into cells via these transporters is obligatorily coupled to efflux of certain other amino acids out of the cells. Earlier studies focused on the utility of the $ATB^{0,+}$ transporter for drug delivery (Ganapathy and Ganapathy, (2005) Curr. Drug Targets Immune Endocr. Metabol. Disord. 5: 357-364; see also U.S. patent application Ser. Nos. 10/467,893 and 11/813,343). Unlike the above-mentioned transporters, $ATB^{0,+}$ is not an amino acid exchanger but an effective influx transporter. It has broad substrate selectivity that includes all essential amino acids, and it possesses exceptional ability to concentrate amino acids inside cells due to the utilization of multiple driving forces. In spite of these special features, it is surprising that the expression of this transporter is very low in normal tissues. Therefore, the transporter might have an essential role in cancer and that highly proliferating tumor cells may up-regulate this transporter to satisfy their increased need for amino acids, especially the essential amino acids and glutamine. We examined the possible relevance of $ATB^{0,+}$ to cancer. First, we investigated the expression of $ATB^{0,+}$ in colorectal cancer using paired normal and cancer tissue specimens from 10 patients (Gupta et al., 2005, Biochim. Biophys. Acta 1741: 215-223). Normal colon expressed minimal $ATB^{0,+}$ mRNA. The expression consistently showed a several-fold increase in cancer over the expression in the corresponding normal tissue in all patients (FIG. 12; N, normal; C, cancer; GM1, GM2, GM6, GM9, GM12, GM25, GM27, GM28, GM29, GM30, GM36, individual patients; 18S RNA as an internal control). Overall, patients with colorectal cancer showed a 22.9±3.0-fold increase in $ATB^{0,+}$ mRNA levels in tumor tissue over normal tissue (P<0.0001). We have confirmed the increased expression of $ATB^{0,+}$ protein in cancer specimens by immunofluorescence methods (Gupta et al., 2005, Biochim. Biophys. Acta 1741: 215-223). We also examined $ATB^{0,+}$ protein expression in hepatic metastasis and lymph node metastasis of colonic primary tumors in two patients. Normal liver tissue far removed from the metastasis expressed very low levels of $ATB^{0,+}$, but the expression was robust in the liver metastasis itself (FIG. 13; small arrow, metastatic tissue; large arrow, brown color indicating $ATB^{0,+}$ protein). Similar results were obtained in lymph node metastases (FIG. 13. Dark staining indicates $ATB^{0,+}$ protein in the metastatic tissue).

Another interesting finding with regard to the relevance of $ATB^{0,+}$ to colorectal cancer is that the transporter is up-regulated markedly in patients with ulcerative colitis (Flach et al., 2006, Inflamm. Bowel Dis. 12:837-842). Since it is well known that chronic inflammation in the colon, as occurs in ulcerative colitis, increases the risk for colorectal cancer, the observed up-regulation of $ATB^{0,+}$ in ulcerative colitis may have pathological significance. Inflammation is associated with increased expression of the inducible isoform of nitric oxide synthase (iNOS) resulting in increased levels of nitric oxide production. Since $ATB^{0,+}$ has the unique ability to mediate the concentrative entry of arginine into cells in a $Na^+/Cl^-$-coupled manner, the coordinated up-regulation of iNOS and $ATB^{0,+}$ may indicate a functional coupling between the two proteins, with the transporter supplying the substrate for the enzyme.

The up-regulation of $ATB^{0,+}$ is not unique to colon cancer. We demonstrated this phenomenon also in several cases of cervical cancer (Gupta et al., 2006, Gynecol. Oncol. 100: 8-13). More recently, we examined the expression of $ATB^{0,+}$ in primary breast cancer. RNA samples isolated from normal mammary tissue (five different individuals) and from breast cancer (five different patients) were evaluated for $ATB^{0,+}$ expression by RTPCR. The expression of the transporter was up-regulated markedly in all five samples of breast cancer compared to normal tissue. We also examined the expression of $ATB^{0,+}$ protein by immunofluorescence methods in normal mammary tissue and in breast cancer. The expression of the transporter was detectable in normal mammary tissue, but the expression levels were markedly higher in breast cancer. These data show that the up-regulation of ATB$^{0,+}$ occurs not only in colon cancer but also in other types of cancer. These data demonstrate that this is likely a general phenomenon in cancer, particularly in cancers of epithelial origin.

Figure 14:
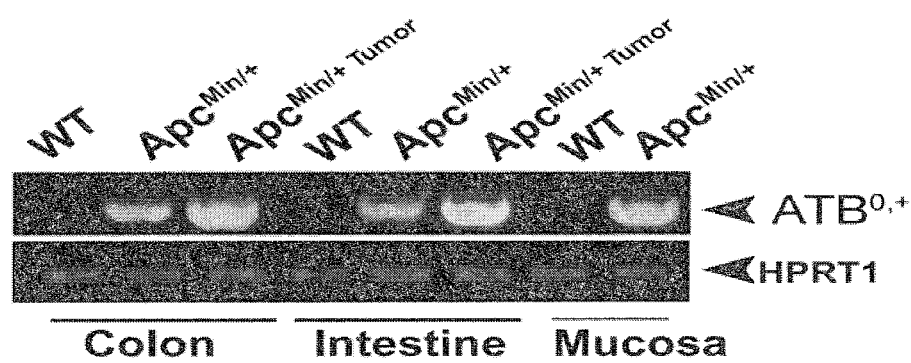
FIG. 14 shows expression of ATB$^{0,+}$ in wild type and Apc$^{Min/+}$ mice.

Expression of ATB$^{0,+}$ in Apc$^{Min/+}$ Mouse and in Human Cancer Cell Lines:

To determine if the up-regulation of ATB$^{0,+}$ observed in colorectal cancer in humans is also true in animal models of colon cancer, we analyzed the expression levels of this transporter in intestinal and colon tissues from wild type mice and Apc$^{Min/+}$ mice. Apc$^{Min/+}$ mice are widely used as an animal model for intestinal/colon cancer. We found marked up-regulation of ATB$^{0,+}$ in tumor tissues collected from Apc$^{Min/+}$ mice compared to corresponding tissues from wild type mice (FIG. 14). Interestingly, even in the intestinal and colon tissues where there were no tumors, the expression of ATB$^{0,+}$ was higher in Apc$^{Min/+}$ mice. Homozygous Apc$^{Min}$ mutation is embryonic lethal in mice, and tumor sites in heterozygous mice (Apc$^{Min/+}$) exhibit loss of heterozygosity. Therefore, our findings indicate a dose-dependent relationship between the Apc$^{Min}$ mutation and up-regulation of ATB$^{0,+}$. Recently we examined the expression of ATB$^{0,+}$ in several cell lines of breast cancer and colon cancer origin (Karunakaran et al., 2008, Biochem. J. 414: 343-355). These studies showed that the transporter is expressed at low or below detectable levels in normal cell lines. This was true in mammary epithelial cell lines (HMEC, MCF10A, and HBL100) and colon epithelial cell lines (NCM460 and CCD841). In contrast, several cancer cell lines expressed the transporter robustly. In cancer cell lines of mammary gland origin, the estrogen receptor-positive cancer cell lines MCF7, T-47D, ZR75.1, and MB-361 expressed the transporter. In cancer cell lines of colonic origin, five out nine cell lines expressed the transporter (FIG. 14). The ATB$^{0,+}$-positive colon cancer cell lines included SW620, KM12C, KM12L4, HCT116, and LS174T.

Methods

Analysis of the Expression of ATB$^{0,+}$ mRNA.

Two μg of RNA was reverse transcribed using the Gene Amp PCR system (Roche). HPRT1 or 18S mRNA was used as an internal control. Human ATB$^{0,+}$-specific PCR primers were designed based on the nucleotide sequences available in GenBank (upstream primer: 5'-GAAGGAGAAAGTGTCG-GCTTCA-3' (SEQ ID NO:1); downstream primer: 5'-TAC-CACCTTGCCAGACGATTTG-3' (SEQ ID NO:2)).

Analysis of ATB$^{0,+}$ Protein by Western Blot.

Cell lysates were prepared by sonication in 10 mM Tris/ HCl buffer (pH 7.6) containing protease inhibitors (50 mM NaF, 0.2 mM vanadate, 1 mM phenylmethylsulfonylfluoride, 5 μg/ml aprotinin, 1 μg/ml pepstatin A, and 2 μg/ml leupeptin) and 1% Triton X-100. 50 μg of protein was fractionated on SDS-PAGE gels and transferred to Protran nitrocellulose membrane (Schleicher & Schull). Membranes were blocked with 5% skim milk, exposed to primary antibody at 4° C. overnight followed by treatment with appropriate secondary antibody, conjugated to horseradish peroxidase, at room temperature for 1 hour, and developed by ECL Super Signal Western System (Pierce).

Immunohistochemistry.

Tissue samples were used to prepare 4 μm sections for immunohistochemistry. These sections were deparaffinized in xylene and rehydrated through graded alcohols. Endogenous peroxidase activity was quenched with methanol/ H$_2$O$_2$. Immunostaining was performed using a polyclonal antibody specific for ATB$^{0,+}$. The experiment was run in parallel in the absence of the primary antibody to serve as a negative control. Immunopositive signals were detected using appropriate secondary antibodies conjugated with fluorescent probes. Slides were visualized by epifluorescence using a fluorescence microscope.

Example 5

Discovery of α-Methyltryptophan as a Blocker of ATB$^{0,+}$

Tryptophan is a substrate for ATB$^{0,+}$. While screening a variety of tryptophan derivatives for interaction with ATB$^{0,+}$, we found that α-methyl-DL-tryptophan (α-MT) inhibited ATB$^{0,+}$-mediated glycine uptake but did not induce inward currents in ATB$^{0,+}$-expressing Xenopus oocytes (Karunakaran et al., 2008, Biochem. J. 414: 343-355). Inhibition of glycine uptake could occur because α-MT is a transportable substrate for ATB$^{0,+}$ thus competing with glycine for the uptake process, or because it blocks the transporter without itself being transported. The Xenopus oocyte expression system can differentiate between these two modes of inhibition because transportable substrates would induce inward currents whereas blockers would not. The inability of α-MT to induce currents indicates that it functions as a blocker of ATB$^{0,+}$. We next wanted to determine the potency of α-MT to block the transporter under conditions that simulate those in vivo, with all naturally occurring amino acids present at physiologic concentrations. ATB$^{0,+}$ accepts all proteinogenic amino acids except glutamate and aspartate. Therefore, using the Xenopus oocyte expression system, we monitored the transport activity of human ATB$^{0,+}$ in the presence of an amino acid mixture consisting of all proteinogenic amino acids, each at its respective physiologic concentration found in plasma. Inward currents were detected under these conditions in oocytes expressing human ATB$^{0,+}$. α-MT blocked the ATB$^{0,+}$-mediated inward currents in the presence of these amino acids. The inhibition was dose-dependent; the concentration of the blocker necessary to elicit 50% maximal inhibition was 255±24 μM (Karunakaran et al., 2008, Biochem. J. 414: 343-355).

α-Methyl-L-Tryptophan (α-MLT) is More Potent than α-Methyl-D-Tryptophan as a Blocker of ATB$^{0,+}$.

Figure 15:
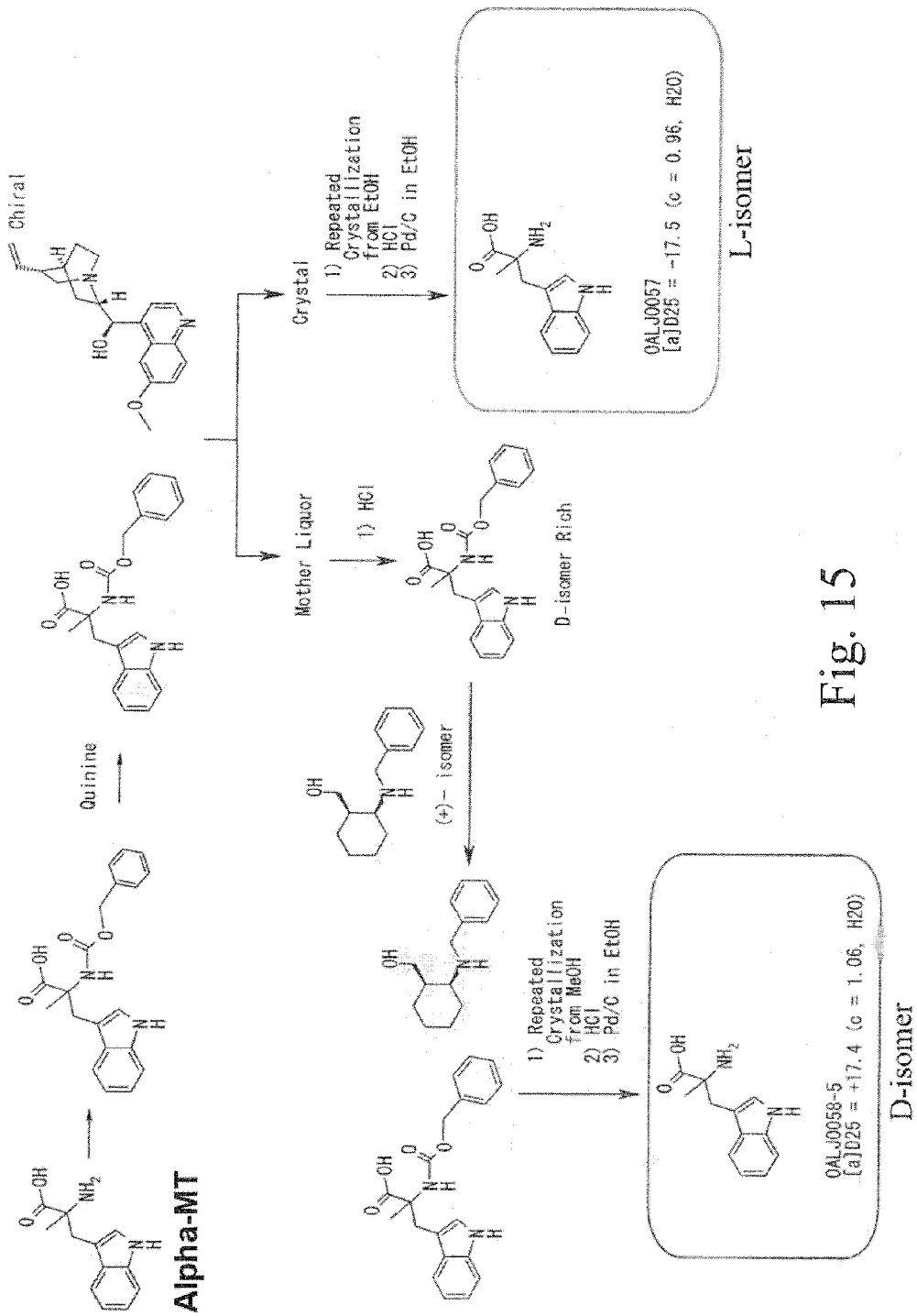
FIG. 15 shows isolation of L- and D-isomers of α-methyl-tryptophan from the DL form.

Although α-methyl-DL-tryptophan is a blocker of ATB$^{0,+}$, its potency is weak. This example demonstrates that the L-isomer of α-methyltryptophan is a more potent blocker than the D-isomer. The only commercially available α-methyltryptophan is the DL-form. Thus, we developed an optical resolution method to separate the L-isomer from the DL-form (FIG. 15). With this method, we purified the L and D-isomers of this compound. We then examined the potencies of the two isomers as a blocker of ATB$^{0,+}$ in Xenopus oocytes using the amino acid mixture simulating the plasma. The concentration of the L-isomer to elicit 50% maximal inhibition was 18±5 μM. This value is 14 times less than the corresponding value for the DL-form. With the D-isomer, the inhibition never increased beyond 40% even at 1 mM.

Example 6

Amino Acid Deprivation in ATB$^{0,+}$-Positive Colon Cancer Cell Lines in the Presence of ATB$^{0,+}$ Blocker The mTOR pathway plays a critical role in nutrient signaling in mammalian cells (Wang and Proud, 2006, Physiology (Bethesda) 21: 362-369). Amino acid starvation leads to specific changes in this pathway. We sought evidence for amino acid starvation in ATB$^{0,+}$-positive colon cancer cell lines when exposed to α-methyl-L-tryptophan (α-MLT) (250 μM).

Figure 16:
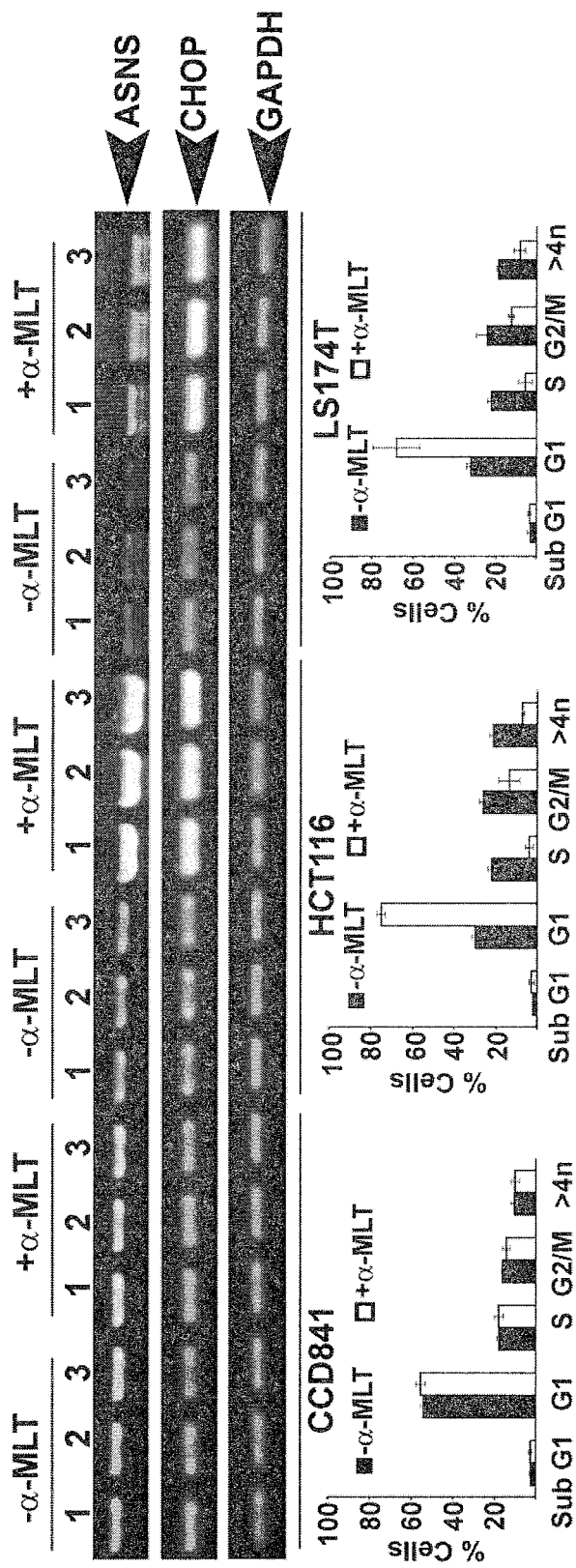
FIG. 16 shows evidence of amino acid starvation and cell cycle arrest in colon cancer cells with 24 hour treatment with α-MT.
Figure 17:
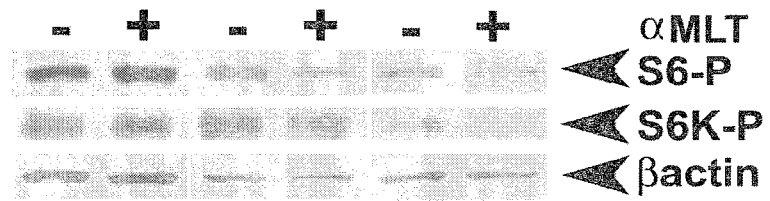
FIG. 17 shows regulation of mTOR signaling by α-MT in cancer cells (HCT116 & LS174T) but not in normal cells (CCD841).
Figure 18:
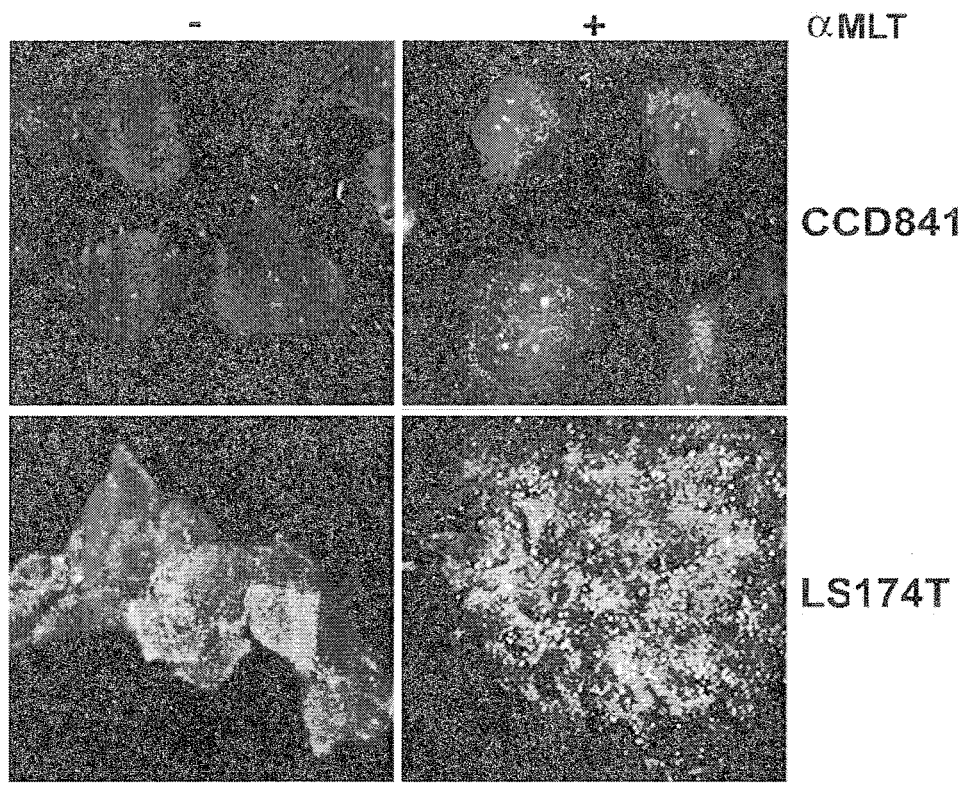
FIG. 18 shows induction of autophagy by α-MT in colon cancer cells (LS174T) but not in normal colon cells (CCD841) as evidenced from immunofluorescent localization of LC-3.
Figure 19:
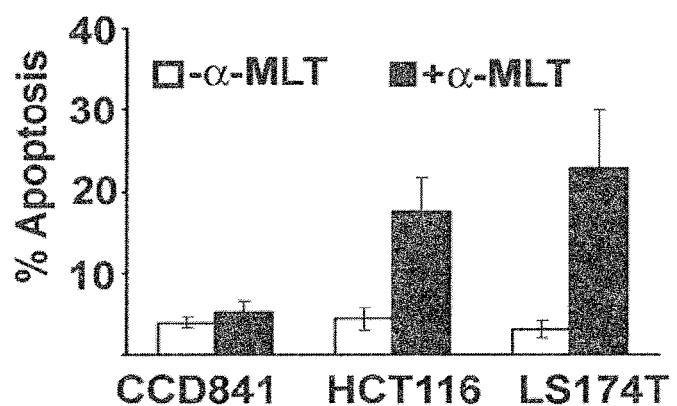
FIG. 19 shows induction of apoptosis in colon cancer cells (HCT116 & LS174T) but not in normal colon cells (CCD841).

With a 24 hour exposure to α-MLT, the genes coding for asparagine synthetase (ASNS) and the endoplasmic reticulum stress signal molecule CHOP were induced in $ATB^{0,+}$-positive HCT116 and LS174T cells (cancer cell lines) but not in $ATB^{0,+}$-negative CCD841 cells (a normal cell line) (FIG. 16; treatment done in triplicate). ASNS and CHOP are important sensors of amino acid nutrition in mammalian cells and their expression is up-regulated during amino acid deprivation. These changes were also accompanied with cell cycle arrest in cancer cell lines (FIG. 16). In the normal cell line CCD841, there was no difference between control and α-MLT-treated cells in terms of percent of cells in difference cell cycle stages. In contrast, treatment with α-MLT increased significantly the percent of HCT116 and LS174T cells in G1 phase and decreased the percent of cells in S and G2/M phases. These data show that α-MLT induces amino acid starvation and cell cycle arrest specifically in $ATB^{0,+}$-positive cancer cells but has no effect on normal cells. We also found decreased phosphorylation of S6 protein and S6 kinase in the mTOR pathway in HCT116 and LS174T cells but not in CCD841 cells when exposed to α-MLT for 24 h (FIG. 17; S6-P, phosphorylated form of S6 protein; S6K-P, phosphorylated form of S6 kinase). The phosphorylation pattern observed in the two cancer cell lines is a hallmark of changes in mTOR pathway in response to amino acid deprivation. Autophagy (self-cannabilism) is another cellular process that is induced when cells undergo amino acid deprivation (Eisenberg-Lerner and Kimchi, 2009, Apoptosis 14: 376-391). To survive in the absence of exogenous essential amino acids during amino acid deprivation, cells engage in autophagic degradation of intracellular macromolecules and organelles as a source of these amino acids. Therefore, we investigated the process of autophagy in LS174T cells with and without exposure to α-MLT for 24 hours. For this, we analyzed the distribution of LC-3 protein. During autophagy, LC-3 gets concentrated in autophagosomes; thus cells undergoing autophagy exhibit punctuate fluorescent signals for LC-3 near the nucleus when detected by immunofluorescence. Confocal analysis of LS174T cells, when not exposed to α-MLT, did not show punctate fluorescent signals for LC-3 whereas the same cells when exposed to α-MLT showed clear evidence of such signals (FIG. 18). CCD841 cells did not undergo autophagy in the absence or presence of α-MLT. When amino acid starvation continues for a long time, pro-survival autophagy turns into pro-death autophagy because cells cannot survive with continued autophagosomal degradation of cellular proteins and organelles. We tested this by monitoring apoptosis in CCD841, HCT116, and LS174T cells with or without α-MLT treatment for 72 hours (FIG. 19). Apoptosis was quantified by FACS analysis. Treatment with α-MLT increased the percent of apoptotic cells (cells in sub-G1 phase) in HCT116 and LS174T cells but not in CCD841 cells, showing that α-MLT induces apoptosis specifically in $ATB^{0,+}$-positive cancer cell lines without having any detrimental effect in normal cells.

Methods

Cell Cycle Analysis.

MCF10A (an $ATB^{0,+}$-negative non-malignant cell line), MCF7 (an $ATB^{0,+}$-positive malignant cell line), and MDA-MB453 (an $ATB^{0,+}$-negative malignant cell line) cells were cultured in 6-well plates in a regular culture medium in the presence or absence of α-methyl-DL-tryptophan (2.5 mM) for 24, 48, and 72 hours. Cells were fixed in 50% ethanol, treated with 0.1% sodium citrate, 1 mg/ml RNase A, and 50 µg/ml propidium iodide, and subjected to FACS (Becton Dickinson FacsCaliber) analysis. The amount of DNA in these cells, detected as chromosome content by propidium iodide binding, was used to identify cells in various stages of cell cycle: $G_1/G_0$, 2N; S, 2-4 N; $G_2/M$, 4N).

Example 7

Figure 20:
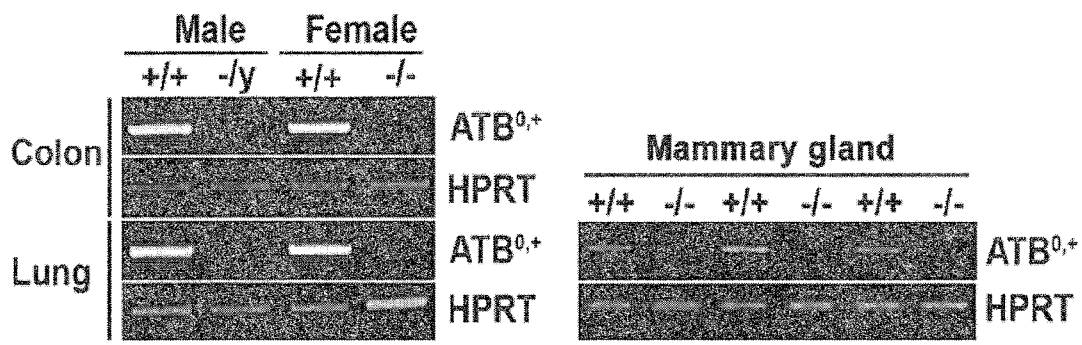
FIG. 20 shows RT-PCR analysis of ATB$^{0,+}$ mRNA expression in colon, lung, and mammary gland in wild type mice compared with hemizygous males (−/y) and homozygous females (−/−).

Generation of Slc6a14$^{-/-}$ Mouse $ATB^{0,+}$ is markedly up-regulated in colon cancer, likely to enable the tumor cells get not only the essential amino acids but also glutamine necessary for their growth. Since colon cancer cells up-regulate this transporter while normal colon cells express only low levels, $ATB^{0,+}$ is an ideal drug target for colon cancer chemotherapy with specific high-affinity blockers of the transporter such as α-MLT. To examine the validity of our hypothesis that up-regulation of $ATB^{0,+}$ is essential for tumor growth, we generated a $ATB^{0,+}$-knockout mouse. The Slc6a14 gene (~27 kb) coding for the transporter is located on X chromosome. The gene consists of 14 exons. We constructed a targeting vector for homologous recombination by deleting a ~2.6 kb region containing exons 1 and 2 and about ~1 kb of the sequence upstream of exon 1 and used the vector to generate the knockout mouse. The knockout of the gene is not lethal and there is no overt phenotype either in hemizygous males (−/y) or in homozygous females (−/−). This is not totally unexpected because $ATB^{0,+}$ is expressed in normal mice only in a limited number of tissues and, that too, only at low levels. We examined the expression of $ATB^{0,+}$ mRNA in three tissues (colon, lung, and mammary gland) where the transporter was expressed in wild type mice at detectable levels. As expected, there was no expression of mRNA in colon and lung in hemizygous males and homozygous females, and in mammary gland in homozygous females (FIG. 20; HPRT, internal control).

Protection from Intestinal Cancer in Apc$^{Min/+}$ Mouse on $ATB^{0,+}$-Null Background.

Apc$^{Min/+}$ mouse is a widely used genetic model of intestinal cancer. Homozygous Apc$^{Min}$ mutation is embryonic lethal while heterozygous mutation leads to intestinal/colon cancer. To determine if deletion of $ATB^{0,+}$ protects against intestinal/colon cancer in this mouse model, we crossbred Apc$^{Min/+}$ mouse with $ATB^{0,+}$-null mouse to generate Apc$^{Min/+}$ on a $ATB^{0,+}$-null background. To date we have had only two animals in control (Apc$^{Min/+}$/Slc6a14$^{+/+}$) and experimental (Apc$^{Min/+}$/Slc6a14$^{-/-}$) group. We compared the incidence of intestinal/colon cancer between the two groups. We found a ~50% decrease in the number of polyps in the intestine and colon in Apc$^{Min/+}$ mouse on $ATB^{0,+}$-null background compared to Apc$^{Min/+}$ mouse on normal $ATB^{0,+}$ background, demonstrating that deletion of $ATB^{0,+}$ does provide significant protection against cancer.

Example 8

Effects of shRNA-Based Silencing of $ATB^{0,+}$ on the Growth and Progression of Tumor $ATB^{0,+}$ is up-regulated in colon cancer cell lines, in primary colon cancer in humans, and in the Apc$^{Min/+}$ mouse model of intestinal/colon cancer. In vitro studies have shown that blockade of $ATB^{0,+}$ transport function with α-MLT in human colon cancer cell lines leads to cell cycle arrest, autophagy, and decreased cell proliferation. If the treatment with α-MLT is extended for longer periods, colon cancer cells undergo apoptosis. This is a pharmacological approach to demonstrate in vitro the potential of $ATB^{0,+}$ as a therapeutic target for treatment of colon cancer. As a complementation to this approach, we will use a molecular biological approach to silence ATB$^{0,+}$ with gene-specific shRNA in human colon cancer cell lines and then examine the effects of the gene silencing on the growth and progression of tumor in vivo in the nude mouse xenograft model using these cell lines.

Generation of Stable Cell Lines with ATB$^{0,+}$-Specific shRNA.

We will use HCT116 and LS174T cells to develop stable cell lines with conditional expression of ATB$^{0,+}$-specific shRNA. Both cell lines express robust ATB$^{0,+}$ transport activity and form tumor in the nude mouse xenograft model system. We expect that if the expression of ATB$^{0,+}$ is silenced, the tumor-forming potential of these cell lines will be compromised. First, we will select the most effective siRNA for maximal silencing of the transporter. We will use the commercial company Dharmacon siDESIGN Center to design and synthesize ATB$^{0,+}$-specific siRNAs. siRNA-mediated silencing of ATB$^{0,+}$ will be evaluated by transient transfection assays followed by quantitative RT-PCR, Western blot, and transport assays. The transport function of ATB$^{0,+}$ is routinely monitored in our laboratory as the Na$^+$/Cl$^-$-dependent D-serine uptake. We will test at least three to five ATB$^{0,+}$-specific siRNAs and will select the best one for further studies. Generation of stable cell lines will be done using a vector-based short hairpin RNA (shRNA) technology. We will generate stable cell lines with HCT116-TetOn and LS174T-TetOn cells, which will express ATB$^{0,+}$-specific shRNA only upon exposure to doxycyclin. This conditional silencing is essential for our studies because we believe that the conventional silencing of the transporter in colon cancer cell lines will lead to growth arrest and apoptosis when the cell lines are kept in culture for extended periods of time. Therefore, we may not be able to generate stable clones. Even if we get stable cell lines, we predict that these cell lines must have adapted to amino acid deprivation induced by the silencing of ATB$^{0,+}$ by up-regulating other amino acid transport systems. Such cell lines may not be appropriate to determine the specific role of ATB$^{0,+}$ in cancer cell growth. To generate the stable cell lines for conditional silencing of ATB$^{0,+}$, first we will clone the ATB$^{0,+}$-specific shRNA in pSUPERIOR.puro vector (from Oligoengine), a TetOn-inducible vector with puromycin resistance, to construct the pSUPERIOR.puro-ATB$^{0,+}$ shRNA plasmid. Second, we will generate HCT116-TetOn and LS174T-TetOn stable cell lines by using the TetOn vector (from Clontech) with G418 selection. Third, we will introduce the ATB$^{0,+}$-specific shRNA into HCT116-TetOn and LS174T-TetOn cells by using the pSUPERIOR.puro-ATB$^{0,+}$ shRNA plasmid with puromycin and G418 selection. After four weeks of antibiotics selection (100 µg/ml G418 and 2 µg/ml puromycin), single colonies will be picked up and expanded. As a control, the pSUPERIOR.puro-Scramble plasmid containing a non-specific scrambled shRNA will be used. The conditional knockdown will be examined by exposing the cells to doxycyclin (2 µg/ml) and then by assessing the expression levels of the transporter. The silencing of ATB$^{0,+}$ will be confirmed by quantitative RT-PCR, Western blot, and transport assays. Once the conditional knockdown is confirmed, the stable cell lines will be used for xenograft in nude mice as described below.

Nude Mouse Xenograft Model.

Xenografts will be established in nude (nu/nu) female Balb/c mice by inoculation of control and shRNA-cell lines ($10^7$ cells in 100 µl of phosphate-buffered saline) into the right flank as described previously (Kwon et al., 2008, Cancer 112: 1462-1470). Expression of ATB$^{0,+}$-specific shRNA will be induced in vivo in the xenografted cell lines by administration of doxycyclin (2 µg/ml) to mice in drinking water. Tumor volume will be measured using calipers every three days and the volume will be calculated using the formula $V = L \times W^2/2$, where L represents the largest tumor diameter and W represents the smallest tumor diameter. Volume will be expressed in mm3 and the relative tumor volume (V/V$_0$) will be determined by dividing the measured tumor volume (V) by the initial tumor volume at day 0 of treatment (V$_0$). Tumors will be harvested from untreated and treated animals at different periods and will be processed for histology (to examine the pathological differences between treated and untreated), RNA extraction (for analysis of ASNS and CHOP mRNA levels, which are markers for amino acid deprivation), and protein extraction (for analysis of the phosphorylation status of S6 and S6 kinase that are markers for changes in mTOR pathway induced by amino acid deprivation due to the silencing of ATB$^{0,+}$ and also for analysis of PARP cleavage and caspase activation as markers for apoptosis).

Inhibition of ATB$^{0,+}$ Transport Function with α-MLT in HCT116 and LS174T Cells Leads to Growth Arrest.

Extended periods of treatment with α-MLT lead to apoptosis in these cells. Therefore, we anticipate that the stable cell lines expressing ATB$^{0,+}$-specific shRNA will exhibit a slow-growing phenotype compared to the corresponding parent cell lines when exposed to doxycyclin in vitro. When xenografted in nude mice, we expect the ATB$^{0,+}$-silenced cell lines to have a markedly reduced tumor-forming potential in the presence of doxycyclin. Additional conditional knockdown systems may also be used. Four different monoclonal antibodies specific for human ATB$^{0,+}$ have already been generated using a recombinant C-terminal tail of the transporter as the antigen. Two of these antibodies work very well in Western blot and one antibody is excellent for immunofluorescence analysis of the transporter protein. These antibodies will be used in monitoring the silencing of ATB$^{0,+}$ in these studies.

Example 9

Effects of Slc6a14 Deletion on Intestinal/Colon Cancer

If Slc6a14 coding for ATB$^{0,+}$ is obligatory for proliferation and growth of colon cancer cells, deletion of the gene should decrease the initiation and progression of colon cancer in chemically induced and in genetically engineered colon cancer animal models. We propose to use Slc6a14$^{-/-}$ mice to test this prediction.

Animals.

Slc6a14$^{-/-}$ mice are viable and fertile. We will intercross this mouse line with the Apc$^{Min/+}$ mouse line to generate the Apc$^{Min/+}$ mouse with the Slc6a14$^{-/-}$ background. We already have a colony of Apc$^{Min/+}$ mice (Thangaraju et al., 2008, J. Gastrointest. Surg. 12: 1773-1782). Homozygous mice with Apc$^{Min}$ mutation are embryonic lethal; however, heterozygous mice with Apc$^{Min}$ mutation (Apc$^{Min/+}$) develop intestinal cancer and, at later stages, colon cancer. Thus, this example will use only the mice with heterozygous mutation for Apc$^{Min}$.

Carcinogen Treatment.

Age-matched (5-month-old) wild type and Slc6a14$^{-/-}$ mice will be injected i.p. with 10 mg/kg body weight of azoxymethane once a week for eight weeks (Frank et al., 2008, J. Biol. Chem. 283: 24729-24737). Azoxymethane (Sigma) will be suspended in 0.9% saline at a concentration of 1 mg/ml prior to injection. At three different periods (1, 2, and 3 months) following the day of the last i.p. injection, mice will be killed, and the small intestine and colon will be removed. After flushing with ice-cold phosphate-buffered saline to remove the luminal contents, the intestine and colon will be cut and opened longitudinally and all visible tumors will be scored and counted in a blinded fashion under a microscope. The small intestine will be divided visually into three segments of approximately equal length (proximal, middle, and distal segments). Multiplicity, location, and size of adenomas will be recorded within these segments and the colon. Adenomas will be differentiated by size (diameter) into <1 mm, 1-3 mm, and >3 mm. Histological assessment of progression in the largest tumors isolated from the intestinal tract will be carried out. In addition, the small intestine and colon will be made into Swiss rolls and the histology of the entire intestinal tract will be evaluated. For this, the specimens will be fixed in 10% formalin, paraffin-embedded, sectioned, and stained with hematoxylin and eosin. Morphological assessment will be made by light microscopy. Differences in survival age, morphological score, tumor size, and tumor number between groups will be evaluated statistically by either one-way analysis of variance with subsequent Tukey's pairwise comparison or a two-sample Student's t test.

Intestinal/Colon Cancer in Wild Type and $Apc^{Min/+}$ Mice on Control and $Slc6a14^{-/-}$ Genetic Background.

These studies will involve three groups of animals: wild type mice, $Apc^{Min/+}$ mice on control genetic background with functional $ATB^{0,+}$ ($Slc6a14^{+/+}$), and $Apc^{Min/+}$ mice on $ATB^{0,+}$-null genetic background ($Slc6a14^{-/-}$). These mice will be monitored for the tumor-free survival or tumor burden for their lifetime. $Apc^{Min/+}$ mice develop intestinal tumors within 2 months and survive for about 9-12 months. Therefore, it will be of significance to record the tumor-free survival of each mouse line used in the study to see if deletion of Slc6a14 in $Apc^{Min/+}$ mice influences the survival. If the survival period is increased with deletion of Slc6a14, it might indicate a decrease in tumor burden or an absence of tumor formation and growth in these mice. Adenomas in the small intestine and colon will be assessed and statistical analysis performed as described above. These studies will unequivocally test the hypothesis that deletion of Slc6a14 prevents or decreases the initiation and progression of adenomas in intestine/colon in $Apc^{Min/+}$ mice.

We expect that $Slc6a14^{-/-}$ mice will have decreased tumor burden in intestine and colon when bred on $Apc^{Min/+}$ genetic background or upon treatment with carcinogen. We will analyze the tumor load in the $Apc^{Min/+}$ colon cancer mouse model by preparing Swiss rolls of the mouse intestine and assessing tumor size and tumor number (Thangaraju et al., 2008, J. Gastrointest. Surg. 12: 1773-1782).

Example 10

Effects of Pharmacological Blockade of $ATB^{0,+}$ with α-MLT on Tumor Growth in Two Different Models of Colon Cancer Azoxymethane is a carcinogen that induces colon cancer in mice. $Apc^{Min}$ mutation in mice also causes intestinal/colon cancer. We propose to use these two models of colon cancer to evaluate the therapeutic potential of α-MLT, a blocker of $ATB^{0,+}$ transport function, in the treatment of colon cancer.

For this example, five-month-old mice will be injected i.p. with 10 mg/kg body weight of azoxymethane once a week for 8 weeks (Frank et al., 2008, J. Biol. Chem. 283: 24729-24737). On the day of the first injection, mice will be divided into two groups, one without treatment with α-MLT and the other with treatment with α-MLT. Azoxymethane (Sigma) will be suspended in 0.9% saline at a concentration of 1 mg/ml prior to injection. The treatment groups will receive α-MLT in drinking water. Based on the $IC_{50}$ value of α-MLT as a blocker of $ATB^{0,+}$ (18±5 μM), we predict that maintenance of 150-200 μM concentration of the blocker in the plasma would be sufficient to block $ATB^{0,+}$ in xenografted colon cancer cells. We estimate that this would require α-MLT at the concentration of 2 mg/ml in drinking water based on published data on the structurally related compound 1-methyl-D-tryptophan (Hou et al., 2007, Cancer Res. 67: 792-801). Hou et al. (Hou et al., 2007, Cancer Res. 67: 792-801) have shown that 1-methyl-D-tryptophan, when administered in drinking water to mice at a concentration of 2 mg/ml, the plasma levels were 35-40 μM. Since the L-isomers of amino acids are much more orally bioavailable than the D-isomers, we predict that the oral absorption of α-MLT will be more efficient than that of 1-methyl-D-tryptophan. This will be confirmed by measurement of plasma levels of α-MLT by HPLC. If the concentrations are lower than the desired 150-200 μM, the concentration of α-MLT in drinking water will be increased appropriately. At three different periods (1, 2, and 3 months) following the day of the last i.p. injection, mice will be killed, and the small intestine and colon will be removed. After flushing with ice-cold phosphate-buffered saline to remove the luminal contents, the intestine and colon will be cut open longitudinally and all visible tumors will be scored and counted in a blinded fashion under a microscope. The small intestine will be divided visually into three segments of approximately equal length (proximal, middle, and distal segments). Multiplicity, location, and size of adenomas will be recorded within these segments and the colon. Adenomas will be differentiated by size (diameter) into <1 mm, 1-3 mm, and >3 mm. Histological assessment of progression in the largest tumors isolated from the intestinal tract will be carried out at the Histology Core in our institution. In addition, the small intestine and colon will be made into Swiss rolls and the histology of the entire intestinal tract will be evaluated. For this, the specimens will be fixed in 10% founalin, paraffin-embedded, sectioned, and stained with hematoxylin and eosin. Morphological assessment will be made by light microscopy. Differences in survival age, morphological score, tumor size, and tumor number between groups will be evaluated statistically by either one-way analysis of variance with subsequent Tukey's pairwise comparison or a two-sample Student's t test.

Similar studies will also be done using $Apc^{Min/+}$ mice. We already have a colony of $Apc^{Min/+}$ mice (Thangaraju et al., 2008, J. Gastrointest. Surg. 12: 1773-1782). Homozygous mice with $Apc^{Min}$ mutation die in embryo; heterozygous mice with $Apc^{Min}$ mutation ($Apc^{Min/+}$) develop intestinal cancer and, at later stages, colon cancer. That is the reason why our mouse lines will have only the heterozygous mutation for $Apc^{Min}$. $Apc^{Min/+}$ mice develop intestinal tumors within 2 months and survive for about 9-12 months. At the time of weaning (3-4 weeks of age), $Apc^{Min/+}$ mice will be divided into two groups: control group and treatment group. Each group will have 8 mice. The treatment group will receive α-MLT in drinking water as described above. Adenomas in the small intestine and colon will be assessed and statistical analysis performed as described above.

We expect that treatment with α-MLT will decrease the growth of tumor in the azoxymethane-induced mouse model of colon cancer as well as in the $Apc^{Min/+}$ transgenic mouse model of intestinal/colon cancer. With this example, alternative methods of drug administration (e.g., implantable subcutaneous pellets) may also be employed. Hou et al. (Hou et al., 2007, Cancer Res. 67: 792-801) have used the drinking water approach as well as subcutaneous pellets as a mode of 1-methyl-D-tryptophan delivery in mice; both methods were effective.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of treating cancer in a subject, the method comprising administering to the subject in need thereof a composition comprising an inhibitor of the $ATB^{0,+}$ amino acid transporter, wherein the cancer expresses the $ATB^{0,+}$ amino acid transporter; and wherein the inhibitor of the $ATB^{0,+}$ amino acid transporter comprises alpha methyl tryptophan.

2. A method of killing a cancer cell, the method comprising contacting the cancer cell with an inhibitor of the $ATB^{0,+}$ amino acid transporter; wherein the cancer cells demonstrate increased expression of the $ATB^{0,+}$ amino acid transporter compared to normal, noncancerous cells; and wherein the inhibitor of the $ATB^{0,+}$ amino acid transporter comprises alpha methyl tryptophan.

3. The method of claim 1, wherein the composition comprises the L isomer of alpha methyl tryptophan and does not comprise the D isomer of alpha methyl tryptophan.

4. The method of claim 3, wherein the composition comprises the L isomer of alpha methyl tryptophan and does not comprise the D isomer of alpha methyl tryptophan.

5. A method of treating cancer in a subject, the method comprising:
determining that the cancer cells demonstrate expression of the $ATB^{0,+}$ amino acid transporter; and
administering to the subject in need thereof a composition comprising an inhibitor of the $ATB^{0,+}$ amino acid transporter;
wherein the inhibitor of the $ATB^{0,+}$ amino acid transporter comprises alpha methyl tryptophan.

6. The method of claim 5, wherein the composition comprises the L isomer of alpha methyl tryptophan and does not comprise the D isomer of alpha methyl tryptophan.

7. The method of claim 5, wherein the cancer is selected from the group consisting of colon cancer, cervical cancer, breast cancer and pancreatic cancer.

8. The method of claim 1, wherein the cancer is selected from the group consisting of colon cancer, cervical cancer, breast cancer and pancreatic cancer.

9. The method of claim 8, wherein the cancer is metastatic.

10. The method of claim 1, wherein the composition is formulated for parenteral delivery.

11. The method of claim 1, wherein the composition is formulated for enteral delivery.

12. The method of claim 1, wherein the inhibitor of the $ATB^{0,+}$ amino acid transporter inhibits transport of D-serine but the inhibitor of the $ATB^{0,+}$ amino acid transporter itself is not transported.

13. The method of claim 1, further comprising the administration of one or more additional therapeutic agents.

14. The method of claim 5, further comprising the administration of one or more additional therapeutic agents.

15. The method of claim 1, wherein the alpha methyl tryptophan comprises a racemic mixture of alpha methyl tryptophan, comprises the L isomer of alpha methyl tryptophan and does not comprise the D isomer of alpha methyl tryptophan, or comprises the D isomer of alpha methyl tryptophan and does not comprise the L isomer of alpha methyl tryptophan.

16. The method of claim 2, wherein the alpha methyl tryptophan comprises a racemic mixture of alpha methyl tryptophan, comprises the L isomer of alpha methyl tryptophan and does not comprise the D isomer of alpha methyl tryptophan, or comprises the D isomer of alpha methyl tryptophan and does not comprise the L isomer of alpha methyl tryptophan.

17. The method of claim 5, wherein the alpha methyl tryptophan comprises a racemic mixture of alpha methyl tryptophan, comprises the L isomer of alpha methyl tryptophan and does not comprise the D isomer of alpha methyl tryptophan, or comprises the D isomer of alpha methyl tryptophan and does not comprise the L isomer of alpha methyl tryptophan.

18. The method of claim 7, wherein the cancer is metastatic.

19. The method of claim 5, wherein the cancer is selected from the group consisting of colon cancer, cervical cancer, breast cancer and pancreatic cancer.

20. The method of claim 19, wherein the cancer is metastatic.

21. The method of claim 5, wherein the composition is formulated for parenteral delivery.

22. The method of claim 5, wherein the composition is formulated for enteral delivery.

* * * * *